(12) United States Patent
Ly

(10) Patent No.: US 9,730,914 B2
(45) Date of Patent: Aug. 15, 2017

(54) 3,5-DIAMINOPYRAZOLE KINASE INHIBITORS

(71) Applicant: Axikin Pharmaceuticals, Inc., San Diego, CA (US)

(72) Inventor: Tai Wei Ly, San Diego, CA (US)

(73) Assignee: Axikin Pharmaceuticals, San Mateo, CA (US)

( * ) Notice: Subject to any disclaimer, the term of this patent is extended or adjusted under 35 U.S.C. 154(b) by 0 days.

(21) Appl. No.: 15/364,099

(22) Filed: Nov. 29, 2016

(65) Prior Publication Data

US 2017/0087131 A1    Mar. 30, 2017

Related U.S. Application Data

(62) Division of application No. 14/979,294, filed on Dec. 22, 2015, now Pat. No. 9,546,163.

(60) Provisional application No. 62/096,308, filed on Dec. 23, 2014.

(51) Int. Cl.
| | | |
|---|---|---|
| A61K 31/415 | (2006.01) |
| A61K 31/635 | (2006.01) |
| A61K 31/496 | (2006.01) |
| A61K 31/5377 | (2006.01) |
| A61K 31/4155 | (2006.01) |
| A61K 31/4439 | (2006.01) |
| A61K 31/4178 | (2006.01) |
| A61K 31/416 | (2006.01) |
| A61K 31/454 | (2006.01) |
| A61K 31/541 | (2006.01) |
| A61K 31/422 | (2006.01) |
| A61K 31/506 | (2006.01) |
| A61K 31/4545 | (2006.01) |

(52) U.S. Cl.
CPC .......... *A61K 31/415* (2013.01); *A61K 31/416* (2013.01); *A61K 31/4155* (2013.01); *A61K 31/4178* (2013.01); *A61K 31/422* (2013.01); *A61K 31/4439* (2013.01); *A61K 31/454* (2013.01); *A61K 31/4545* (2013.01); *A61K 31/496* (2013.01); *A61K 31/506* (2013.01); *A61K 31/5377* (2013.01); *A61K 31/541* (2013.01); *A61K 31/635* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,110,941 A | 5/1992 | Taniguchi et al. |
| 5,120,548 A | 6/1992 | McClelland et al. |
| 5,294,612 A | 3/1994 | Bacon et al. |
| 5,323,907 A | 6/1994 | Kalvelage |
| 5,354,556 A | 10/1994 | Sparks et al. |
| 5,498,630 A | 3/1996 | Phillion et al. |
| 5,541,187 A | 7/1996 | Bacon et al. |
| 5,591,767 A | 1/1997 | Mohr et al. |
| 5,597,826 A | 1/1997 | Howard et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,693,667 A | 12/1997 | Phillion et al. |
| 5,698,220 A | 12/1997 | Cardinal et al. |

(Continued)

FOREIGN PATENT DOCUMENTS

| | | |
|---|---|---|
| EP | 0 885 890 A1 | 12/1998 |
| WO | 93/07751 A1 | 4/1993 |

(Continued)

OTHER PUBLICATIONS

Serafin et al., "Different concepts of drug delivery in disease entities," Mini Rev. Med. Chem. 9:481-497 (2009).

(Continued)

*Primary Examiner* — Karl J Puttlitz

(57) ABSTRACT

Provided herein are 3,5-diaminopyrazoles, for example, compounds of Formula I, that are useful for modulating regulated-in-COPD kinase activity, and pharmaceutical compositions thereof. Also provided herein are methods of their use for treating, preventing, or ameliorating one or more symptoms of a RC kinase-mediated disorder, disease, or condition.

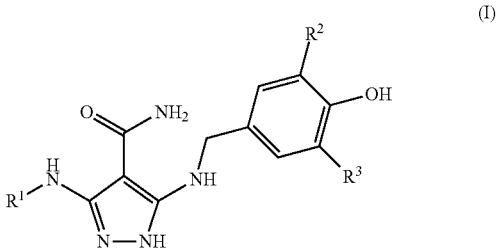

(I)

37 Claims, No Drawings

(56) References Cited

U.S. PATENT DOCUMENTS

| | | |
|---|---|---|
| 5,705,513 A | 1/1998 | Phillion et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,811,411 A | 9/1998 | Phillion et al. |
| 5,834,447 A | 11/1998 | Phillion et al. |
| 5,840,674 A | 11/1998 | Yatvin et al. |
| 5,849,723 A | 12/1998 | Phillion et al. |
| 5,849,778 A | 12/1998 | Heil et al. |
| 5,891,474 A | 4/1999 | Busetti et al. |
| 5,900,252 A | 5/1999 | Calanchi et al. |
| 5,922,356 A | 7/1999 | Koseki et al. |
| 5,922,751 A | 7/1999 | Cavalla et al. |
| 5,958,458 A | 9/1999 | Norling et al. |
| 5,959,109 A | 9/1999 | Whitten et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 5,998,466 A | 12/1999 | Phillion et al. |
| 6,004,534 A | 12/1999 | Langer et al. |
| RE36,562 E | 2/2000 | Phillion et al. |
| 6,028,101 A | 2/2000 | Phillion et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,103,749 A | 8/2000 | Cavalla et al. |
| 6,113,943 A | 9/2000 | Okada et al. |
| 6,120,751 A | 9/2000 | Unger |
| 6,131,570 A | 10/2000 | Schuster et al. |
| 6,133,252 A | 10/2000 | Phillion et al. |
| 6,133,276 A | 10/2000 | Whitten et al. |
| 6,139,865 A | 10/2000 | Friend et al. |
| 6,166,057 A | 12/2000 | Phillion et al. |
| 6,197,350 B1 | 3/2001 | Yamagata et al. |
| 6,248,363 B1 | 6/2001 | Patel et al. |
| 6,248,769 B1 | 6/2001 | Cavalla et al. |
| 6,248,894 B1 | 6/2001 | Phillion et al. |
| 6,252,078 B1 | 6/2001 | Phillion et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,270,798 B2 | 8/2001 | Cremer |
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,375,987 B1 | 4/2002 | Farah et al. |
| 6,376,461 B1 | 4/2002 | Igari et al. |
| 6,380,214 B1 | 4/2002 | Gant et al. |
| 6,410,558 B1 | 6/2002 | Phillion et al. |
| 6,419,961 B1 | 7/2002 | Igari et al. |
| 6,464,767 B1 | 10/2002 | Evans et al. |
| 6,468,338 B1 | 10/2002 | Evans et al. |
| 6,472,416 B1 | 10/2002 | Kolasa et al. |
| 6,521,603 B2 | 2/2003 | Phillion et al. |
| 6,589,548 B1 | 7/2003 | Oh et al. |
| 6,593,349 B2 | 7/2003 | McNaughton-Smith et al. |
| 6,613,358 B2 | 9/2003 | Randolph et al. |
| 6,623,756 B1 | 9/2003 | Wilber et al. |
| 6,699,500 B2 | 3/2004 | Okada et al. |
| 6,770,645 B2 | 8/2004 | Denton et al. |
| 6,793,936 B2 | 9/2004 | Devane et al. |
| 6,827,771 B2 | 12/2004 | Omatsu et al. |
| 6,827,947 B2 | 12/2004 | Lofroth et al. |
| 6,838,458 B2 | 1/2005 | Sakya |
| 6,878,726 B2 | 4/2005 | Cheng et al. |
| 6,894,067 B2 | 5/2005 | Minich et al. |
| 6,902,742 B2 | 6/2005 | Devane et al. |
| 6,903,131 B2 | 6/2005 | Taveras et al. |
| 6,958,161 B2 | 10/2005 | Hayes et al. |
| 6,989,451 B2 | 1/2006 | Zhang et al. |
| 7,033,425 B2 | 4/2006 | Blease et al. |
| 7,087,616 B2 | 8/2006 | Fischer et al. |
| 7,119,108 B1 | 10/2006 | Makriyannis et al. |
| 7,132,445 B2 | 11/2006 | Taveras et al. |
| 7,169,410 B1 | 1/2007 | Lau et al. |
| 7,223,782 B2 | 5/2007 | Atkinson et al. |
| 7,253,204 B2 | 8/2007 | Delorme et al. |
| 7,255,876 B2 | 8/2007 | Shinoda et al. |
| 7,393,842 B2 | 7/2008 | Makriyannis et al. |
| 7,402,585 B2 | 7/2008 | Jung et al. |
| 7,416,738 B2 | 8/2008 | Sowden et al. |
| 7,427,414 B2 | 9/2008 | Patel et al. |
| 7,435,731 B2 | 10/2008 | Arora et al. |
| 7,452,880 B2 | 11/2008 | Arora et al. |
| 7,485,322 B2 | 2/2009 | Kerc |
| 7,488,727 B2 | 2/2009 | Cochran et al. |
| 7,514,567 B2 | 4/2009 | Change et al. |
| 7,528,134 B2 | 5/2009 | Bhatia et al. |
| 7,528,142 B2 | 5/2009 | Binch et al. |
| 7,531,560 B2 | 5/2009 | Cogan et al. |
| 7,662,482 B2 | 2/2010 | Wang et al. |
| 7,718,678 B2 | 5/2010 | Biju |
| 7,728,017 B2 | 6/2010 | Lauffer et al. |
| 7,737,151 B2 | 6/2010 | Mortimore et al. |
| 7,745,440 B2 | 6/2010 | Makriyannis et al. |
| 7,767,672 B2 | 8/2010 | Binch et al. |
| 7,820,685 B2 | 10/2010 | Binch et al. |
| 7,829,685 B2 | 11/2010 | Watanabe et al. |
| 7,868,177 B2 | 1/2011 | Cee et al. |
| 7,872,052 B2 | 1/2011 | Linschoten |
| 7,897,607 B2 | 3/2011 | Gyorkos et al. |
| 7,947,698 B2 | 5/2011 | Atuegbu et al. |
| 7,947,720 B2 | 5/2011 | Taveras et al. |
| 7,964,646 B2 | 6/2011 | Taveras et al. |
| 7,989,456 B2 | 8/2011 | Mortimore et al. |
| 7,998,987 B2 | 8/2011 | Lauffer et al. |
| 8,084,467 B2 | 12/2011 | Makriyannis et al. |
| 8,916,555 B2 * | 12/2014 | Raaum ............... C07D 403/12 514/236.5 |
| 2002/0156073 A1 | 10/2002 | Wagle et al. |
| 2003/0004164 A1 | 1/2003 | Bebbington et al. |
| 2003/0064990 A1 | 4/2003 | Denton et al. |
| 2003/0232836 A1 | 12/2003 | Stewart et al. |
| 2004/0023901 A1 | 2/2004 | Cook et al. |
| 2004/0024085 A1 | 2/2004 | Ishizuka et al. |
| 2004/0029887 A1 | 2/2004 | Bhatia et al. |
| 2004/0097547 A1 | 5/2004 | Taveras et al. |
| 2004/0106794 A1 | 6/2004 | Taveras et al. |
| 2004/0157893 A1 | 8/2004 | Bebbington et al. |
| 2004/0235831 A1 | 11/2004 | Rozot |
| 2004/0259879 A1 | 12/2004 | Cheng et al. |
| 2005/0004135 A1 | 1/2005 | Cheng et al. |
| 2005/0113283 A1 | 5/2005 | Solow-Cordero et al. |
| 2006/0009461 A1 | 1/2006 | Bhatia et al. |
| 2006/0128724 A1 | 6/2006 | Cui et al. |
| 2006/0270628 A1 | 11/2006 | Das et al. |
| 2006/0281749 A1 | 12/2006 | Wagle et al. |
| 2007/0142413 A1 | 6/2007 | Block et al. |
| 2007/0179125 A1 | 8/2007 | Fraysse et al. |
| 2007/0213330 A1 | 9/2007 | Delorme et al. |
| 2008/0064690 A1 | 3/2008 | Atkinson et al. |
| 2008/0064729 A1 | 3/2008 | Gould et al. |
| 2008/0139561 A1 | 6/2008 | Davies et al. |
| 2008/0194606 A1 | 8/2008 | Scott et al. |
| 2008/0200485 A1 | 8/2008 | Xiao et al. |
| 2008/0213165 A1 | 9/2008 | Lieu et al. |
| 2008/0280925 A1 | 11/2008 | Wahhab et al. |
| 2009/0005396 A1 | 1/2009 | Claesson |
| 2009/0029992 A1 | 1/2009 | Agoston et al. |
| 2009/0053455 A1 | 2/2009 | Miyazawa et al. |
| 2009/0062301 A1 | 3/2009 | Maibucher |
| 2009/0081120 A1 | 3/2009 | Lieu et al. |
| 2009/0105266 A1 | 4/2009 | Glatthar et al. |
| 2009/0118146 A1 | 5/2009 | Negoro et al. |
| 2009/0143451 A1 | 6/2009 | Andrews et al. |
| 2009/0181938 A1 | 7/2009 | Binch et al. |

(56) References Cited

U.S. PATENT DOCUMENTS

| | | |
|---|---|---|
| 2009/0215770 A1 | 8/2009 | Jung et al. |
| 2009/0218039 A1 | 9/2009 | Fujie et al. |
| 2009/0227648 A1 | 9/2009 | Lyne et al. |
| 2009/0246378 A1 | 10/2009 | Saito et al. |
| 2009/0326020 A1 | 12/2009 | Miller et al. |
| 2010/0152219 A1 | 6/2010 | Block et al. |
| 2010/0216794 A1 | 8/2010 | Burgdorf et al. |
| 2010/0216827 A1 | 8/2010 | Ma et al. |
| 2010/0240720 A1 | 9/2010 | Pellecchia |
| 2010/0292447 A1 | 11/2010 | Pitner et al. |
| 2010/0310675 A1 | 12/2010 | Binch et al. |
| 2010/0331338 A1 | 12/2010 | Burgdorf et al. |
| 2011/0003691 A1 | 1/2011 | Dietz et al. |
| 2011/0020469 A1 | 1/2011 | Binch et al. |
| 2011/0021541 A1 | 1/2011 | White et al. |
| 2011/0039695 A1 | 2/2011 | Glattli et al. |
| 2011/0053941 A1 | 3/2011 | Mautino et al. |
| 2011/0082146 A1 | 4/2011 | Atuegbu et al. |
| 2011/0092539 A1 | 4/2011 | Gillespie et al. |
| 2011/0144110 A1 | 6/2011 | Wasley et al. |
| 2011/0166139 A1 | 7/2011 | Barlaam et al. |
| 2011/0213029 A1 | 9/2011 | Taveras et al. |
| 2011/0230536 A1 | 9/2011 | Whitten et al. |
| 2011/0253929 A1 | 10/2011 | Stock et al. |
| 2011/0257196 A1 | 10/2011 | Lu et al. |
| 2013/0274227 A1 | 10/2013 | Raaum et al. |
| 2013/0303492 A1* | 11/2013 | Raaum ............... C07D 403/12 514/158 |
| 2015/0080397 A1 | 3/2015 | Ly et al. |
| 2015/0080398 A1* | 3/2015 | Raaum ............... C07D 403/12 514/236.5 |
| 2015/0105389 A1* | 4/2015 | Raaum ............... C07D 403/12 514/236.5 |

FOREIGN PATENT DOCUMENTS

| | | |
|---|---|---|
| WO | 95/22530 A1 | 8/1995 |
| WO | 96/00218 A1 | 1/1996 |
| WO | 97/30978 A1 | 8/1997 |
| WO | 97/45421 A1 | 12/1997 |
| WO | 00/71532 A1 | 11/2000 |
| WO | 01/16138 A1 | 3/2001 |
| WO | 01/29007 A1 | 4/2001 |
| WO | 02/17918 A2 | 3/2002 |
| WO | 02/053160 A1 | 7/2002 |
| WO | 02/059112 A2 | 8/2002 |
| WO | 02/068413 A1 | 9/2002 |
| WO | 02/074388 A1 | 9/2002 |
| WO | 02/074774 A1 | 9/2002 |
| WO | 02/083624 A1 | 10/2002 |
| WO | 03/020217 A2 | 3/2003 |
| WO | 03/031440 A1 | 4/2003 |
| WO | 03/037274 A2 | 5/2003 |
| WO | 03/037335 A1 | 5/2003 |
| WO | 03/037336 A1 | 5/2003 |
| WO | 03/055491 A1 | 7/2003 |
| WO | 03/073989 A2 | 9/2003 |
| WO | 2004/011418 A1 | 2/2004 |
| WO | 2004/047776 A1 | 6/2004 |
| WO | 2004/101531 A1 | 11/2004 |
| WO | 2004/108139 A2 | 12/2004 |
| WO | 2005/000309 A2 | 1/2005 |
| WO | 2005/005435 A1 | 1/2005 |
| WO | 2005/049033 A1 | 6/2005 |
| WO | 2005/085248 A1 | 9/2005 |
| WO | 2005/092896 A1 | 10/2005 |
| WO | 2005/092899 A1 | 10/2005 |
| WO | 2005/099688 A2 | 10/2005 |
| WO | 2005/103010 A2 | 11/2005 |
| WO | 2005/105935 A1 | 11/2005 |
| WO | 2006/021881 A2 | 3/2006 |
| WO | 2006/026488 A1 | 3/2006 |
| WO | 2006/055831 A2 | 5/2006 |
| WO | 2006/082392 A1 | 8/2006 |
| WO | 2006/087530 A1 | 8/2006 |
| WO | 2006/087538 A1 | 8/2006 |
| WO | 2006/104196 A1 | 10/2006 |
| WO | 2006/115452 A1 | 11/2006 |
| WO | 2006/117560 A1 | 11/2006 |
| WO | 2007/002764 A2 | 1/2007 |
| WO | 2007/022384 A2 | 2/2007 |
| WO | 2007/023382 A2 | 3/2007 |
| WO | 2007/024021 A1 | 3/2007 |
| WO | 2007/056221 A2 | 5/2007 |
| WO | 2007/059299 A1 | 5/2007 |
| WO | 2007/064797 A2 | 6/2007 |
| WO | 2007/084868 A2 | 7/2007 |
| WO | 2007/100646 A1 | 9/2007 |
| WO | 2007/107318 A1 | 9/2007 |
| WO | 2008/028140 A1 | 3/2008 |
| WO | 2008/030448 A1 | 3/2008 |
| WO | 2008/071456 A2 | 6/2008 |
| WO | 2008/104077 A1 | 9/2008 |
| WO | 2008/118822 A1 | 10/2008 |
| WO | 2008/154026 A1 | 12/2008 |
| WO | 2009/032694 A1 | 3/2009 |
| WO | 2009/046784 A1 | 4/2009 |
| WO | 2009/046840 A1 | 4/2009 |
| WO | 2009/064802 A2 | 5/2009 |
| WO | 2009/073620 A2 | 6/2009 |
| WO | 2009/106203 A1 | 9/2009 |
| WO | 2009/112523 A1 | 9/2009 |
| WO | 2009/124903 A1 | 10/2009 |
| WO | 2009/147167 A1 | 12/2009 |
| WO | 2009/153589 A1 | 12/2009 |
| WO | 2010/019903 A1 | 2/2010 |
| WO | 2010/048207 A2 | 4/2010 |
| WO | 2010/048559 A2 | 4/2010 |
| WO | 2010/072696 A2 | 7/2010 |
| WO | 2010/096314 A1 | 8/2010 |
| WO | 2010/101964 A2 | 9/2010 |
| WO | 2010/103240 A1 | 9/2010 |
| WO | 2010/107765 A1 | 9/2010 |
| WO | 2010/107768 A1 | 9/2010 |
| WO | 2010/108115 A1 | 9/2010 |
| WO | 2010/142801 A1 | 12/2010 |
| WO | 2011/050245 A1 | 4/2011 |
| WO | 2011/056895 A1 | 9/2011 |
| WO | 2011/109059 A1 | 9/2011 |
| WO | 2011/158042 A2 | 12/2011 |
| WO | 2012/154880 A1 | 11/2012 |
| WO | 2013/138613 A1 | 9/2013 |

OTHER PUBLICATIONS

Shalaby et al., "Synthesis of new 5-N-pyrazolyl amino acids, pyrazolopyrimidines and pyrazolopyridines derivatives," Acta Chim. Slovenica 47(2):187-203 (2000).

Shi et al., "Current advances in sustained-release systems for parenteral drug delivery," Expert Opin. Drug Deliv. 2 (6):1039-1058 (2005).

Singh et al., "Recent trends in targeted anticancer prodrug and conjugate design," Curr. Med. Chem. 15 (18):1802-1826 (2008).

Sinha et al., "Colonic drug delivery: prodrug approach," Pharm. Res. 18(5):557-564 (2001).

Sinhababu and Thakker, "Prodrugs of anticancer agents," Adv. Drug Delievery Rev. 19:241-273 (1996).

Sloan et al., "Design for optimized topical delivery: Prodrugs and a paradigm change," Pharm. Res. 23 (12):2729-2747 (2006).

Sloan et al., "Designing for topical delivery: prodrugs can make the difference," Med. Res. Rev. 23(6):763-793 (2003).

Stańczak et al., "Prodrugs and soft drugs," Pharmacol. Rep. 58(5):599-613 (2006).

Stella et al., "Prodrug strategies to overcome poor water solubility," Adv. Drug Deliv. Rev. 59:677-694 (2007).

Stella et al., "Prodrugs. Do they have advantages in clinical practice?," Drugs 29(5):455-473 (1985).

Tan et al., "Development and optimization of anti-HIV nucleoside analogs and prodrugs: A review of their cellular pharmacology,

(56) References Cited

OTHER PUBLICATIONS structure-activity relationships and pharmacokinetics," Adv. Drug Delivery Rev. 39:117-151 (1999).
Taylor, "Improved passive oral drug delivery via prodrugs," Adv. Drug Delivery Rev. 19:131-148 (1996).
Verma et al., "Formulation aspects in the development of osmotically controlled oral drug delivery systems," J. Controlled Release 79:7-27 (2002).
Verma et al., "Osmotically controlled oral drug delivery," Drug Development and Industrial Pharmacy 26(7):695-708 (2000).
Waller et al., "Prodrugs," Br. J. Clin. Pharmac. 28:497-507 (1989).
Wang et al,. "Prodrug approaches to the improved delivery of peptide drugs," Curr. Pharm. Design 5(4):265-287 (1999).
Wermuth et al., "Designing prodrugs and bioprecursors I: carrier prodrugs," Pract. Med. Chem., Academic Press, San Diego, CA 671-696 (1996).
Wiebe and Knaus, "Concepts for the design of anti-HIV nucleoside prodrugs for treating cephalic HIV infection," Adv. Drug Delivery Rev. 39(1-3):63-80 (1999).
Zhao et al., "Synthesis and biological activity of 1-sulfonyl-3,5-diamino-1H-pyrazole-4-nitrile derivatives," [Online] Database Chemical Abstracts Service, Columbus, Ohio, Accession No. 2001:475123.
Asgharnejad in "Transport Processes in Pharmaceutical Systems," Amidon et al., Ed., Marcell Dekker, 185-218, 2000.
Bondock et al., "Synthesis and antimicrobial activity of some new thiazole, thiophene and pyrazole derivatives containing benzothiazole moiety," Eur. J. Med. Chem. 45(9):3692-3701 (2010).
Bundgaard, H, "Bioreversible derivatization of drugs—principle and applicability to improve the therapeutic effects of drugs," Arch. Pharm. Chemi 86(1):1-39 (1979). (English translation not available).
Han et al., "Targeted Prodrug Design to Optimize Drug Delivery," AAPS Pharmsci 2(1):1-11 (2000).
Wermuth, C.G. (1984) Designing prodrugs and bioprecursors. Drug Design: Fact or Fantasy?, pp. 47-72. Academic Press, London.
Sreenivasa et al., "Synthesis of bioactive molecule fluoro benzothiazole comprising potent heterocyclic moieties for anthelmentic activity." Arch. Pharm. Sci. & Res. 1(2):150-157 (2009).
Zhao et al., "Synthesis and biological activity of 1-sulfonyl-3,5-diamino-1H-pyrazole-4-nitrile derivatives," Chinese Journal of Applied Chemistry 18(6):423-427 (2001). (English Abstract attached).
Ahmed et al., "Synthesis of some pyrazolopyrimidines as purine analogues," J. Heterocycl. Chem. 44(4):803-810 (2007).
Ammar et al., "Cyanoacetanilides intermediates in heterocyclic synthesis. Part 5: preparation of hitherto unknown 5-aminopyrazole and pyrazolo[1,5-a]pyrimidine derivatives containing sulfamoyl moiety," J. Chin. Chem. Soc. 56 (5):1064-1071 (2009).
Anand et al., "Current prodrug strategies via membrane transporters/receptors," Expert Opin. Biol. Ther. 2(6):607-620 (2002).
Badawy et al., "Microenvironmental pH modulation in solid dosage forms," J. Pharm. Sci. 96(5):948-959 (2007).
Balant et al., "Prodrugs for the improvement of drug absorption via different routes of administration," Eur. J. Metab. Pharmacokinet 15(2):143-153 (1990).
Balimane and Sinko, "Involvement of multiple transporters in the oral absorption of nucleoside analogues," Adv. Drug Delivery Rev. 39(1):183-209 (1999).
Berge et al., "Pharmaceuticals salts," J. Pharm. Sci. 66: 1-19 (1977).
Bondock et al, "Synthesis and antimicrobial activity of some new thiazole, thiophene and pyrazole derivatives containing benzothiazole moiety," Eur. J. Med. Chem. 45(9):3694 (2010).
Browne, "Fosphenytoin (Cerebyx)," Clin. Neuropharmacol. 20(1):1-12 (1997).
Bundgaard, "Controlled Drug Delivery," International Symposium of the Association for Pharmaceutical Technology 17:179-196 (1984).
Bundgaard, "Means to enhance penetration, prodrugs as a a means to improve the delivery of peptide drugs," Adv. Drug Delivery Rev. 8:1-38 (1992).
Bussemer et al., "Pulsatile drug-delivery systems," Crit. Rev. Ther. Drug Carrier System 18(5):433-458 (2001).
Chrzanowski, "Preformulation considerations for controlled release dosage forms. Part I. Selecting candidates," AAPS PharmSciTech. 9(2):635-638 (2008).
Chrzanowski, "Preformulation considerations for controlled release dosage forms: Part II—Selecting Candidate Support," AAPS PharmSciTech. 9(2):639-645 (2008).
Conway, "Recent patents on ocular drug delivery systems," Recent Pat. Drug Deliv. Formul. 2:1-8 (2008).
Erion et al., "Liver-targeted drug delivery using HepDirect prodrugs," J. Pharmacal. Exp. Ther. 312(2):554-560 (2005).
Fang et al., "Prodrug strategy for enhancing drug delivery via skin," Curr. Drug Discov. Technol. 3:211-224 (2006).
Farquhar et al., "Biologically reversible phosphate-protective groups," J. Pharm. Sci. 72(3):324-325 (1983).
Fleisher et al., "Design of prodrugs for improved gastrointestinal absorption by intestinal enzyme targeting," Methods Enzymol. 112:360-381 (1985).
Fleisher et al., "Improved oral drug delivery: solubility limitations overcome by the use of prodrugs," Adv. Drug Delivery Rev. 19:115-130 (1996).
Freeman et al., "Bioreversible protection for the phospho group: chemical stability and bioactivation of di(4-acetoxybenzyl) methylphosphonate with carboxyesterase," J. Chem. Soc. Chem. Commun. 875-877 (1991).
Friis and Bundgaard, "Prodrugs of phosphates and phosphonates: Novel lipophilic α-acyloxyalkyl ester derivatives of phosphate- or phosphonate containing drugs masking the negative charges of these groups," Eur. J. Pharm. Sci. 4 (1):49-59 (1996).
Gallardo and Skalsky, "Controlled release solid dosage forms using combinations of (meth)acrylate copolymers," Pharm. Dev. Technol. 13(5):413-423 (2008).
Gangwar et al., "Prodrug strategies to enhance the intestinal absorption of peptides," Drug Discovery Today 2 (4):148-155 (1997).
Gazzaniga et al., "Oral pulsatile delivery systems based on swellable hydrophilic polymers," Eur. J. Pharm. Biopharm. 68(1):11-18 (2008).
Gomes et al., "Cyclization-activated prodrugs," Molecules 12(11):2484-2506 (2007).
Hafez et al., "Synthesis, structural elucidation, and in vitro antitumor activities of some pyrazolopyrimidines and schiff bases derived from 5-amino-3-(arylaminio)-1H-pyrazole-4-carboxamides," Sci. Pharm. 81:339-357 (2013).
Han et al., "Targeted prodrug design to optimize drug delivery," AAPS Pharmsci. 2(1):45-58 (2000).
Harper, "Drug Latentiation," Progress in Drug Research, Birkäuser Verlag Basel, Switzerland 4:221-294 (1962).
Higuchi, "Pro-drug, molecular structure and percutaneous delivery,", Des. Biopharm. Prop. Prodrugs Analogs, Am. Pharm. Assoc. Acad. Pharm. Sci., Washington DC 409-421 (1976).
Hu, "Prodrugs: effective solutions for solubility, permeability and targeting challenges," IDrugs 7(8):736-742 (2004).
Huttunen et al., "Cytochrome P450-activated prodrugs: targeted drug delivery," Curr. Med. Chem. 15 (23):2346-2365 (2008).
Kalantzi et al., "Recent advances in oral pulsatile drug delivery," Recent Pat. Drug Deliv. Formul. 3(1):49-63 (2009).
Kratz et al., "Prodrug strategies in anticancer chemotherapy," Chem. Med. Chem. 3(1):20-53 (2008).
Maroni et al., "Oral pulsatile drug delivery systems,"Expert Opin. Drug Deliv. 2(5):855-871 (2005).
Mizen et al., "The use of esters as prodrugs for oral delivery of beta-lactam antibiotics," Pharm. Biotech. 11:345-365 (1998).
Nagarwal et al., "Phase transition system: novel oral in-situ gel," Curr. Drug Deliv. 5:282-289 (2008).
Nathwani and Wood, "Penicillins. A current review of their clinical pharmacology and therapeutic use," Drugs 45 (6):866-894 (1993).
Onishi et al., "In vitro and in vivo evaluation of microparticulate drug delivery systems composed of macromolecular prodrugs," Molecules 13(9):2136-2155 (2008).

(56) References Cited

OTHER PUBLICATIONS

Patterson et al., "Prodrugs in genetic chemoradiotherapy," Curr. Pharm. Des. 9(26):2131-2154 (2003).
Pauletti et al. "Improvement of oral peptide bioavailability: peptidomimetics and prodrug strategies," Adv. Drug Delivery Rev. 27(2-3):235-256 (1997).
Pavan et al., "Progress in drug delivery to the central nervous system by the prodrug approach," Molecules 13 (5):1035-I 065 (2008).
Rao, "Capping drugs: development of prodrugs," Resonace 19-27 (2003).
Rautio et al., "Prodrug approaches for CNS delivery," AAPS J. 10(1):92-102 (2008).
Rautio et al., "Prodrugs: design and clinical applications," Nat. Rev. Drug Discov. 7(3): 255-270 (2008).
Robinson et al., "LEAPT: lectin-directed enzyme-activated prodrug therapy," Proc. Natl. Acad. Sci. U.S.A. 101 (40):14527-14532 (2004).
Roy et al., "Multiparticulate formulation approach to pulsatile drug delivery: current perspectives," J. Controlled Release 134(2):74-80 (2009).
Saigal et al., "Site specific chronotherapeutic drug delivery systems: a patent review," Recent Pat. Drug Deliv. Formul. 3(1):64-70 (2009).
Sandros et al., "Prodrugs in cardiovascular therapy," Molecules 13(5): 1156-1178 (2008).
Santus and Baker, "Osmotic drug delivery, a review of the patent literature," J. Controlled Release 35:1-21 (1995).

\* cited by examiner

3,5-DIAMINOPYRAZOLE KINASE INHIBITORS

CROSS REFERENCE TO RELATED APPLICATION

This application is a divisional of U.S. patent application Ser. No. 14/979,294, filed Dec. 22, 2015, which claims the benefit of priority to U.S. Provisional Patent Application Ser. No. 62/096,308, filed Dec. 23, 2014, the disclosure of each of which is incorporated by reference herein in its entirety.

FIELD

Provided herein are 3,5-diaminopyrazoles that are useful for modulating regulated-in-COPD kinase (RC kinase) activity, and pharmaceutical compositions thereof. Also provided herein are methods of their use for treating, preventing, or ameliorating one or more symptoms of a RC kinase-mediated disorder, disease, or condition.

BACKGROUND

Regulated-in-COPD kinase (RC kinase) is closely related to MAPKKK3, which directly regulates the pathways of stress-activated protein kinase (SAPK) and extracellular signal-regulated protein kinase (ERK) by activating SEK and MEK1/2, respectively. See, U.S. Pat. No. 7,829,685, the disclosure of which is incorporated herein by reference in its entirety. RC kinase is an upstream activator in MAP kinase signaling cascades, capable of phosphorylating MAP kinase kinases such as MKK4 and MKK6. The activation of MKK4 leads to the phosphorylation of JNK-type MAP kinases, leading to the phosphorylation of c-Jun and thus the activation of the AP-1 transcription factor complex. As a result, interleukin-8 production is increased, leading to the recruitment of inflammatory cells, such as neutrophils. The activation of MKK6 leads to the phosphorylation of p38-type MAP kinases, which is important in the activation of the immune response and key regulators of inflammatory cytokine expression. The occurrence of cellular stresses, the activation of the transcription factor, and the overproduction of interleukin-8 are characteristic of numerous inflammatory diseases. Thus, the regulation of RC kinase activity can potentially be beneficial to patients with inflammatory diseases.

RC kinase has been shown to be highly expressed in the lung and trachea. Some of the expressed sequence tags of human RC kinase are also expressed in the lung epithelial cells and in primary lung cystic fibrosis epithelial cells. Microarray analyses of patients with chronic obstructive pulmonary disease (COPD) show that RC kinase is upregulated in the lungs of COPD patients. On the cellular level, it has been shown that the expression of RC kinase is upregulated in response to hyperosmotic or oxidative stress. For example, the expression of RC kinase in cells increases significantly after exposure to potassium chloride or hydrogen peroxide. Potassium chloride subjects cells to a hyperosmotic stress. Hydrogen peroxide subjects cells to an oxidative stress, which impairs the capacity of B cells to stimulate specific T cells. Such upregulation of RC kinase in cells in response to hyperosmotic and oxidative stress suggests that higher expression of RC kinase in lungs of COPD patients may be the result of cellular stresses caused by the irritants in tobacco smoke or stresses caused by inflammatory response to those irritants. Therefore, RC kinase inhibitors are potentially useful for the treatment of inflammatory diseases, including COPD.

Janus Kinase (JAK) is a family of intracellular, nonreceptor tyrosine kinases that transduce cytokine-mediated signals via the JAK/STAT signaling pathway. This family, comprising JAK1, JAK2, JAK3 and TYK2 (tyrosine kinase 2), was first described more than 20 years ago, but the complexities underlying their activation, regulation and pleiotropic signaling functions are still being explored. See, e.g., Babon et al., *Biochem J.* 2014; 462(1), 1-13. Disrupted or dysregulated JAK-STAT functionality may result in a variety of disorders, including immune deficiency syndromes and cancers. Aaronson et al., *Science* 2002, 296, 1653-1655. The primary challenge with most kinase inhibitor programs aimed at non-oncologic indications is to define the degree of selectivity required across the kinome that will limit the off-target kinase induced side effect profile of a potential drug. Designing in compound selectivity across the kinome is difficult due to the highly conserved structure within the kinase active site. See, e.g., Rokosz et al., *Expert Opin. Ther. Targets* 2008, 12(7) 883-903; Bhattacharya et al., *Biochemical and Biophysical Research Communications* 2003, 307, 267-273.

Since disrupting the JAK-STAT pathway may lead to unwanted side effects, development of a therapeutic that can inhibit RC kinase expression while minimally affecting the function of JAK is of great importance.

SUMMARY OF THE DISCLOSURE

Provided herein is a 3,5-diaminopyrazole of Formula I:

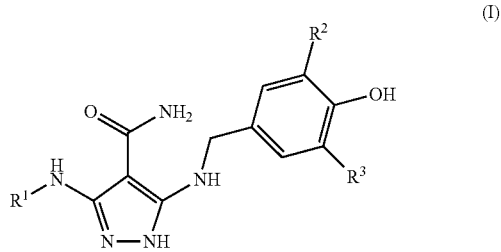

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents Q, where each Q is independently selected from halo, $C_{1-6}$ alkyl, heteroaryl, and heterocyclyl, each of which is further optionally substituted with one or more $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula I:

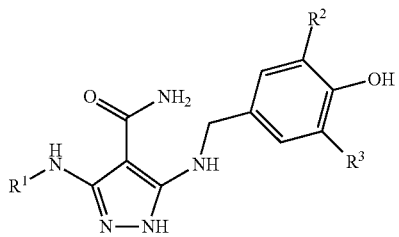

(I)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents Q, where each Q is independently selected from halo, amino, aminosulfonyl, $C_{1-6}$ alkyl, $C_{1-6}$ alkoxy, alkylamido, cyano, aryl, heteroaryl, and heterocyclyl, each of which is further optionally substituted with one or more $C_{1-6}$ alkyl, halo, cyano, oxo, aralkyl, dialkylamino, arylamido, heterocyclyl, heterocyclylalkyl, and heterocyclylcarbonyl;

with the proviso that the compound is not 3-((3-chlorophenyl)amino)-5-((4-hydroxy-3,5-dimethylbenzyl)amino)-1H-pyrazole-4-carboxamide.

Also provided herein are pharmaceutical compositions comprising a compound disclosed herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

Further provided herein is a method of treating, preventing, or ameliorating one or more symptoms of a RC kinase-mediated disorder, disease, or condition in a subject, comprising administering to the subject a therapeutically effective amount of a compound disclosed herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

Additionally provided herein is a method of modulating RC kinase activity, comprising contacting a RC kinase with a therapeutically effective amount of a compound disclosed herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

Also provided herein is a method of treating, preventing, or ameliorating one or more symptoms of a RC kinase-mediated disorder, disease, or condition in a subject, comprising administering to the subject a therapeutically effective amount of a compound disclosed herein, e.g., a compound of Formula I, including a stereoisomer, enantiomer, mixture of enantiomers, mixture of diastereomers, or isotopic variant thereof, or a pharmaceutically acceptable salt, solvate, hydrate, or prodrug thereof, wherein the compound displays increased potency against RC kinase and/or increased RC kinase to JAK2 selectivity and/or increased RC kinase to JAK3 selectivity.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers an amount, concentration, or dosage of a compound that is required for 50% inhibition of a maximal response in an assay that measures such response.

The term "$CC_{50}$" refers an amount, concentration, or dosage of a compound that results in 50% reduction of the viability of a host. In certain embodiments, the $CC_{50}$ of a compound is the amount, concentration, or dosage of the compound that is required to reduce the viability of cells treated with the compound by 50%, in comparison with cells untreated with the compound.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science* and *Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s), wherein the alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_2$-6) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s), wherein the alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_2$-6) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, wherein the cycloalkyl is optionally substituted with one or more substituents Q as described herein. In one embodiment, cycloalkyl groups may be saturated or unsaturated but non-aromatic, and/or spiro, and/or non-spiro, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent polycyclic aromatic group that contain at least one aromatic carbon ring, wherein the aryl is optionally substituted with one or more substituents Q as described herein. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl).

The term "aralkyl" or "arylalkyl" refers to a monovalent alkyl group substituted with one or more aryl groups, wherein the aralkyl or arylalkyl is optionally substituted with one or more substituents Q as described herein. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, N, and P in the ring. Heteroaryl groups are bonded to the rest of a molecule through the aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heteroaralkyl" or "heteroarylalkyl" refers to a monovalent alkyl group substituted with one or more heteroaryl groups, wherein the alkyl and heteroaryl are each as defined herein. In certain embodiments, the heteroaralkyl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, 3-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "heterocyclylalkyl" refers to a monovalent alkyl group substituted with one or more heterocyclyl groups, wherein the alkyl and heterocyclyl are each as defined herein. In certain embodiments, the heteroaralkyl is optionally substituted with one or more substituents Q as described herein.

The term "alkoxy" refers to —O-alkyl, wherein the alkyl is as defined herein. For example, the term "$C_{1-6}$ alkoxy" refers to —O—$C_{1-6}$ alkyl.

The term "halogen", "halide" or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents Q, each of which is independently selected from, e.g., (a) oxo (=O), halo, cyano (—CN), nitro (—$NO_2$), and pentafluorosulfanyl (—$SF_5$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, heteroaralkyl, heterocyclyl, and heterocyclylalkyl, each of which is further optionally substituted with one or more, in one embodiment, one, two, three, or four, substituents $Q^a$; and (c) —B($R^a$)$OR^d$, —B($OR^a$)$OR^d$, —C(O)$R^a$, —C(O)$OR^a$, —C(O)$NR^b R^c$, —C($NR^a$)$NR^b R^c$, —$OR^a$, —OC(O)$R^a$, —OC(O)$OR^a$, —OC(O)$NR^b R^c$, —OC(=$NR^a$)$NR^b R^c$, —OS(O)$R^a$, —OS(O)$_2 R^a$, —OS(O)$NR^b R^c$, —OS(O)$_2$ $NR^b R^c$, —$NR^b R^c$, —$NR^a$C(O)$R^d$, —$NR^a$C(O)$OR^d$, —$NR^a$C(O)$NR^b R^c$, —$NR^a$C(=$NR^d$)$NR^b R^c$, —$NR^a$S(O) $R^d$, —$NR^a$S(O)$_2 R^d$, —$NR^a$S(O)$NR^b R^c$, —$NR^a$S(O)$_2$ $NR^b R^c$, —P(O)$R^a R^d$, —P(O)($OR^a$)$R^d$, —P(O)($OR^a$)($OR^d$), —$SR^a$, —S(O)$R^a$, —S(O)$_2 R^a$, —S(O)$NR^b R^c$, and —S(O)$_2$ $NR^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, heteroaralkyl, heterocyclyl, or heterocyclylalkyl, each optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, nitro, and pentafluorosulfanyl (—$SF_5$); and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, heteroaralkyl, heterocyclyl, and heterocyclylalkyl; and (c) —B($R^e$)$OR^g$, —B($OR^e$)$OR^g$, —C(O)$R^e$, —C(O)$OR^e$, —C(O)$NR^f R^g$, —C($NR^e$)$NR^f R^g$, —$OR^e$, —OC(O)$R^e$, —OC(O)$OR^e$, —OC(O)$NR^f R^g$, —OC(=$NR^e$) $NR^f R^g$, —OS(O)$R^e$, —OS(O)$_2 R^e$, —OS(O)$NR^f R^g$, —OS (O)$_2 NR^f R^g$, —$NR^f R^g$, —$NR^e$C(O)$R^h$, —$NR^e$C(O)$OR^h$, —$NR^e$C(O)$NR^f R^g$, —$NR^e$C(=$NR^h$)$NR^f R^g$, —$NR^e$S(O)$R^h$, —$NR^e$S(O)$_2 R^h$, —$NR^e$S(O)$NR^f R^g$, —$NR^e$S(O)$_2 NR^f R^g$, —P(O)$R^e R^h$, —P(O)($OR^e$)$R^h$, —P(O)($OR^e$)($OR^h$), —$SR^e$, —S(O)$R^e$, —S(O)$_2 R^e$, —S(O)$NR^f R^g$, and —S(O)$_2 NR^f R^g$; wherein each $R^e$, $R^f$, $R^g$, and $R^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, heteroaralkyl, heterocyclyl, or heterocyclylalkyl; or (ii) $R^f$ and $R^g$ together with the N atom to which they are attached form heteroaryl or heterocyclyl.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^{2}H$, as example, or any carbon can be $^{13}C$, as example, or any nitrogen can be $^{15}N$, as example, and any oxygen can be $^{18}O$, as example, where feasible according to the judgment of one of skill in the art. In certain embodiments, an "isotopic variant" of a compound contains a unnatural proportion of deuterium.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, MeOH, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "RC kinase" refers to regulated in COPD kinase or a variant thereof. RC kinase variants include proteins substantially homologous to a native RC kinase, i.e., proteins having one or more naturally or non-naturally occurring amino acid deletions, insertions, or substitutions (e.g., RC kinase derivatives, homologs and fragments), as compared to the amino acid sequence of a native RC kinase. The amino acid sequence of a RC kinase variant is at least about 80% identical, at least about 90% identical, or at least about 95% identical to a native RC kinase. Some examples of RC kinases are disclosed in U.S. Pat. No. 7,829,685, the disclosure of which is incorporated herein by reference in its entirety.

The terms "RC kinase-mediated disorder, disease, or condition" and "a disorder, disease, or condition mediated by RC kinase" refer to a disorder, disease, or condition, characterized by abnormal or dysregulated, e.g., less than or greater than normal, RC kinase activity. Abnormal RC kinase functional activity might arise as the result of RC kinase overexpression in cells, expression of RC kinase in cells which normally do not express RC kinase, or dysregulation due to constitutive activation, caused, for example, by a mutation in RC kinase. A RC kinase-mediated disorder, disease, or condition may be completely or partially mediated by abnormal or dysregulated RC kinase activity. In particular, a RC kinase-mediated disorder, disease, or condition is one in which modulation of a RC kinase activity results in some effect on the underlying disorder, disease, or condition, e.g., a RC kinase inhibitor results in some improvement in at least some of patients being treated.

The phrase "a stereoisomer, enantiomer, mixture of enantiomers, mixture of diastereomers, or isotopic variant thereof; or a pharmaceutically acceptable salt, solvate, hydrate, or prodrug thereof" has the same meaning as the phrase "a stereoisomer, enantiomer, mixture of enantiomers, mixture of diastereomers, or isotopic variant of the compound referenced therein; a pharmaceutically acceptable salt, solvate, hydrate, or prodrug of the compound referenced therein; or a pharmaceutically acceptable salt, solvate, hydrate, or prodrug of a stereoisomer, enantiomer, mixture of enantiomers, mixture of diastereomers, or isotopic variant of the compound referenced therein."

Compounds

In one embodiment, provided herein is a 3,5-diaminopyrazole of Formula I:

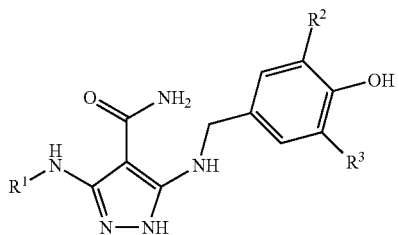

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents Q, where each Q is independently selected from halo, $C_{1-6}$ alkyl, heteroaryl, and heterocyclyl, each of which is further optionally substituted with one or more $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula I:

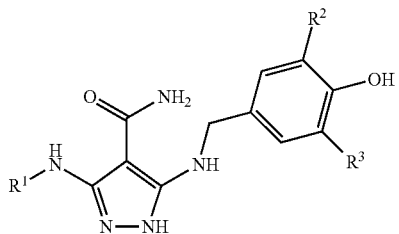

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents Q, where each Q is independently selected from halo, amino, aminosulfonyl, $C_{1-6}$ alkyl, $C_{1-6}$ alkoxy, alkylamido, cyano, aryl, heteroaryl, and heterocyclyl, each of which is further optionally substituted with one or more $C_{1-6}$ alkyl, halo, cyano, oxo, aralkyl, dialkylamino, arylamido, heterocyclyl, heterocyclylalkyl, or heterocyclylcarbonyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl; each of which is optionally substituted with one or more substituents Q, where each Q is independently selected from halo, $C_{1-6}$ alkyl, heteroaryl, and heterocyclyl, each of which is further optionally substituted with one or more, in one embodiment, one, two, three, four, or five $C_{1-6}$ alkyl; and $R^2$ and $R^3$ are each $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl; each of which is optionally substituted with one or more substituents Q, where each Q is independently selected from halo, $C_{1-6}$ alkyl, $C_{1-6}$ alkoxy, alkylamido, amino, sulfonamide, cyano, aryl, heteroaryl, and heterocyclyl, each of which is further optionally substituted with one or more, in one embodiment, one, two, three, four, or five, groups selected from halo, cyano, oxo, aralkyl, dialkylamino, arylamido, heterocyclyl, heterocyclylalkyl, heteroaryl, and heterocyclylcarbonyl;

$R^2$ and $R^3$ are each $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is phenyl or pyridinyl; each of which is optionally substituted with one or more substituents Q;

$R^2$ and $R^3$ are each $C_{1-6}$ alkyl; and

Q is as defined herein;

with the proviso that the compound is not 3-((3-chlorophenyl)amino)-5-((4-hydroxy-3,5-dimethylbenzyl)amino)-1H-pyrazole-4-carboxamide.

In yet another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl; each of which is optionally substituted with one or more substituents Q, where each Q is independently selected from fluoro, chloro, bromo, iodo, methyl, morpholinyl, dimethylmorpholinyl, pyrrolyl, isopropylpiperazinyl, methylpiperazinyl, pyridinyl, and benzylpiperazinyl;

$R^2$ and $R^3$ are each $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In yet another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl; each of which is optionally substituted with one or more substituents Q, where each Q is independently selected from fluoro, chloro, bromo, iodo, cyano, amino, aminosulfonyl, methyl, methoxy, morpholinyl, dimethylmorpholinyl, pyrrolyl, isopropylpiperazinyl, methylpiperazinyl, pyridinyl, benzylpiperazinyl, phenyl, imidazolyl, methoxy, tert-butyl, indazolyl, methylpiperidinyl, (pyrrolidinecarbonyl)piperazinyl, flouropiperidinyl, dimethylpyranyl, piperidinyl, benzyl, 1,1-dioxidothiomorpholino, pyrrolidinylmethyl, morpholinomethyl, dimethylamino, oxazolyl, pyrazolyl, (piperidinecarbonyl)piperazinyl, acetamido, (pyrimidinyl)piperizinyl, piperidinylmethyl, thiomorpholinyl, fluorophenylamido, methoxyphenylamido, isopropylpiperidinyl, cyanomethyl, (trifluoromethyl)phenylamido, and oxomorpholinyl;

$R^2$ and $R^3$ are each $C_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

In still another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is 3-methyl-4-morpholinophenyl, 3-chloro-4-morpholinophenyl, 4-morpholinophenyl, 4-(2,6-dimethylmorpholino)phenyl, 2-morpholino-3-chloropyridin-5-yl, 4-(1H-pyrrol-1-yl)phenyl, 2-morpholinopyridin-5-yl, 4-(4-isopropylpiperazin-1-yl)phenyl, 4-(pyridin-2-yl)phenyl, 4-(4-methylpiperazin-1-yl)phenyl, 5-morpholinopyridin-2-yl, 2-morpholino-3-methylpyridin-5-yl, 2-(4-isopropylpiperazin-1-yl)-3-methylpyridin-5-yl, 2-(4-methylpiperazin-1-yl)-3-methylpyridin-5-yl, 3-chloro-4-(2,6-dimethylmorpholino)phenyl, 4-(pyridin-3-yl)phenyl, or 3-chloro-4-(4-isopropylpiperazin-1-yl)phenyl;

$R^2$ and $R^3$ are each methyl;

with the proviso that the compound is not 3-((3-chlorophenyl)amino)-5-((4-hydroxy-3,5-dimethylbenzyl)amino)-1H-pyrazole-4-carboxamide.

In still another embodiment, provided herein is a compound of Formula I, or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is 3-methyl-4-morpholinophenyl, 3-chloro-4-morpholinophenyl, 4-morpholinophenyl, 4-(2,6-dimethylmorpholino)phenyl, 2-morpholino-3-chloropyridin-5-yl, 4-(1H-pyrrol-1-yl)phenyl, 2-morpholinopyridin-5-yl, 4-(4-isopropylpiperazin-1-yl)phenyl, 4-(pyridin-2-yl)phenyl, 4-(4-methylpiperazin-1-yl)phenyl, 5-morpholinopyridin-2-yl, 2-morpholino-3-methylpyridin-5-yl, 2-(4-isopropylpiperazin-1-yl)-3-methylpyridin-5-yl, 2-(4-methylpiperazin-1-yl)-3-methylpyridin-5-yl, 3-chloro-4-(2,6-dimethylmorpholino)phenyl, 4-(pyridin-3-yl)phenyl, 3-chloro-4-(4-isopropylpiperazin-1-yl)phenyl, 1,1'-biphenyl, 4-(1H-imidazol-1-yl)phenyl, 4-methoxyphenyl, 4-tert-butylphenyl, 1H-indazol-5-yl, 4-(4-methyl-[1,4'-bipiperidin]-1'-yl)phenyl, 4-(4-(pyrrolidine-1-carbonyl)piperazin-1-yl)phenyl, 4-(4-fluoropiperidin-1-yl)phenyl, 6-(2,6-dimethyltetrahydro-2H-pyran-4-yl)pyridin-3-yl, 4-(piperidin-1-yl)phenyl. 3-chloro-4-(2,6-dimethylmorpholino)phenyl, 3-methyl-4-(4-methylpiperazin-1-yl)phenyl, 3-methyl-4-(piperidin-1-yl)phenyl, 4-(4-benzylpiperazin-1-yl)-3-methylphenyl, 4-(1,1-dioxidothiomorpholino)phenyl, (5-(piperidin-1-yl)pyridine-2-yl)phenyl, 4-(4-chloropiperidin-1-yl)phenyl, 4-(pyrrolidin-1-ylmethyl)phenyl, 4-(4-(dimethylamino)piperidin-1-yl)phenyl, 3-fluoro-4-morpholinophenyl, 4-(oxazol-5-yl)phenyl, 4-(4-(morpholine-4-carbonyl)piperazin-1-yl)phenyl, 3-acetamidophenyl, 3-chloro-4-(4-methylpiperazin-1-yl)phenyl, 4-fluorophenyl, 3-cyanophenyl, 4-(4-(pyrimidin-2-yl)piperazin-1-yl)phenyl, 4-(piperidin-1-ylmethyl)phenyl, 4-thiomorpholinophenyl, 4-aminophenyl, 4-(aminosulfonyl)phenyl, 2-(4-(pyrrolidin-1-yl)piperidin-1-yl)pyridin-5-yl, 4-(dimethylamino)phenyl, 4-(morpholinomethyl)phenyl. 2-methoxyphenyl, 4-(4-fluorophenylamido)phenyl, 4-(4,5-dihydro-1H-pyrazol-3-yl)phenyl, 4-(2-methoxyphenylamido)phenyl, 4-(3-methoxyphenylamido)phenyl, 4-(4-methoxyphenylamido)phenyl, 4-(4-isopropylpiperidin-1-yl)phenyl 4-(3-oxomorpholinyl)phenyl, 4-(1H-pyrazol-1-yl)phenyl, 4-(2-cyanomethyl)phenyl, 4-((4-trifluoromethyl)phenylamido)phenyl, or 4-(4-methylpiperidin-1-yl)phenyl;

$R^2$ and $R^3$ are each methyl;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula II:

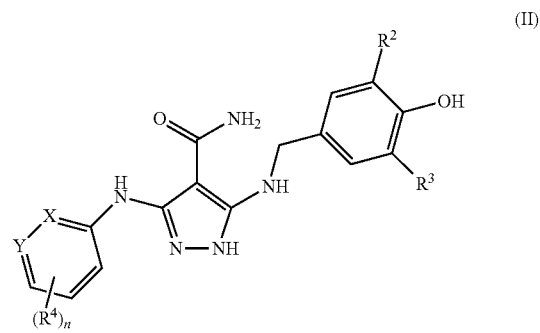

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, $C_{1-6}$ alkyl, $C_{7-15}$ aralkyl, heterocyclyl, each of which is optionally substituted with one or more $C_{1-6}$ alkyl;

wherein X and Y are each independently N or CH; and n is 0, 1, 2, 3, 4, or 5;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula II:

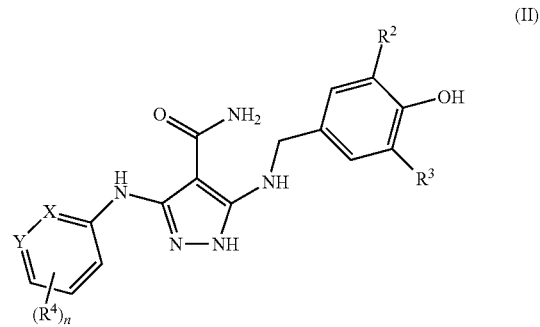

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, alkylamido, cyano, $C_{1-6}$ alkyl, $C_{1-6}$ alkoxy, aryl, $C_{7-15}$ aralkyl, heterocyclyl, and heteroaryl, each of which is optionally substituted with one or more halo, $C_{1-6}$ alkyl, aryl, $C_{7-15}$ aralkyl, heterocyclyl, dialkylamino, or dialkylaminocarbonyl;

wherein X and Y are each independently N or CH; and n is 0, 1, 2, 3, 4, or 5;

In another embodiment, provided herein is a 3,5-diaminopyrazole of Formula II:

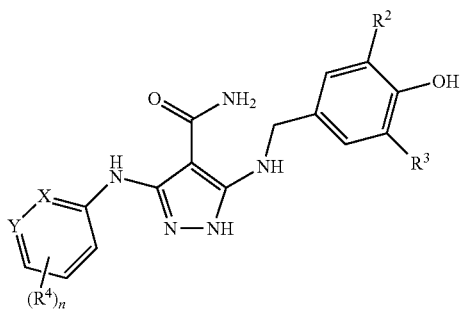

(II)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, amino, aminosulfonyl, alkylamido, arylamido, cyano, $C_{1-6}$ alkyl, $C_{1-6}$ alkoxy, aryl, $C_{7-15}$ aralkyl, heterocyclyl, and heteroaryl, each of which is optionally substituted with one or more halo, cyano, oxo, $C_{1-6}$ alkyl, aryl, $C_{7-15}$ aralkyl, heterocyclyl, oxo, dialkylamino, or dialkylaminocarbonyl;

wherein X and Y are each independently N or CH; and n is 0, 1, 2, 3, 4, or 5;

In another embodiment, provided herein is a 3,5-diaminopyrazole of Formula II-a:

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, $C_{1-6}$ alkyl, heteroaryl, and heterocyclyl, each of which is optionally substituted with one or more $C_{1-6}$ alkyl; and n is 0, 1, 2, 3, 4, or 5;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula II-a:

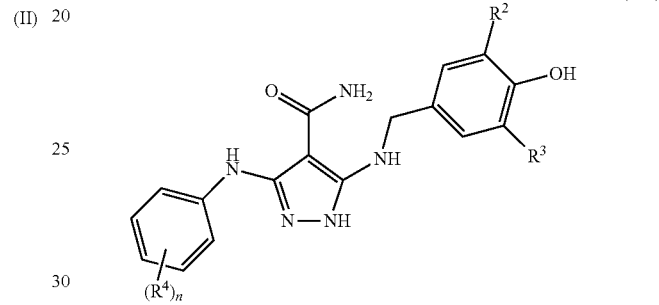

(II-a)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, alkylamido, arylamido, amino, aminosulfonyl, cyano, $C_{1-6}$ alkyl, $C_{1-6}$ alkoxy, aryl, $C_{7-15}$ aralkyl, heterocyclyl, heterocyclylalkyl, and heteroaryl, each of which is optionally substituted with one or more halo, cyano, oxo, $C_{1-6}$ alkyl, aryl, $C_{7-15}$ aralkyl, heterocyclyl, dialkylamino, or dialkylaminocarbonyl; and n is 0, 1, 2, 3, 4, or 5;

with the proviso that the compound is not 3-((3-chlorophenyl)amino)-5-((4-hydroxy-3,5-dimethylbenzyl)amino)-1H-pyrazole-4-carboxamide.

In another embodiment, provided herein is a 3,5-diaminopyrazole of Formula II-b:

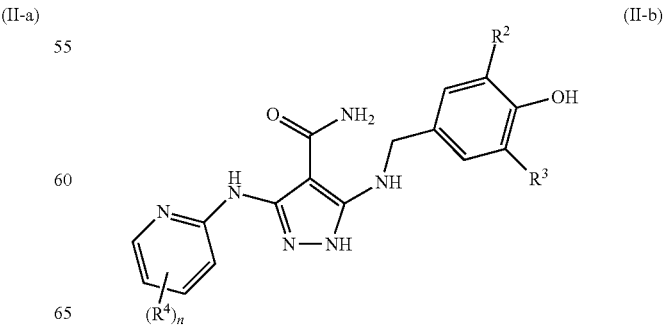

(II-b)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, $C_{1-6}$ alkyl, heteroaryl, and heterocyclyl, each of which is optionally substituted with one or more $C_{1-6}$ alkyl; and n is 0, 1, 2, 3, or 4.

In another embodiment, provided herein is a 3,5-diaminopyrazole of Formula II-c:

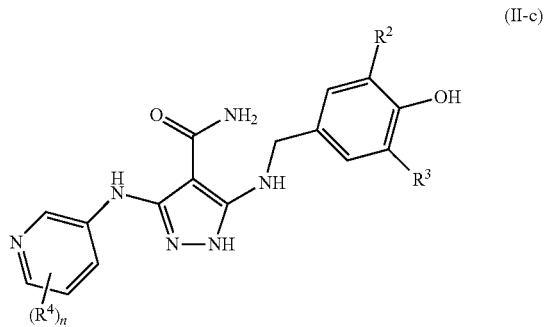

(II-c)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, $C_{1-6}$ alkyl, heteroaryl, and heterocyclyl, each of which is optionally substituted with one or more $C_{1-6}$ alkyl; and n is 0, 1, 2, 3, or 4.

In another embodiment, provided herein is a 3,5-diaminopyrazole of Formula II-c:

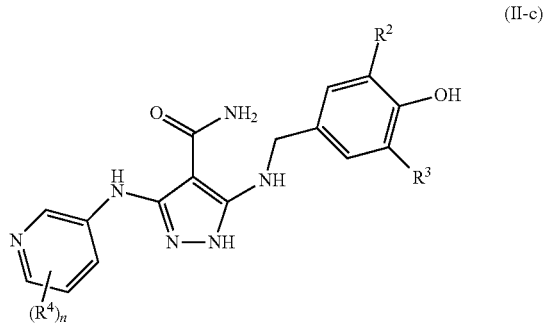

(II-c)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^2$ and $R^3$ are each independently $C_{1-6}$ alkyl or $C_{3-10}$ cycloalkyl;

wherein each alkyl or cycloalkyl is optionally substituted with one or more halo;

each $R^4$ is independently selected from halo, $C_{1-6}$ alkyl, heteroaryl, and heterocyclyl, each of which is optionally substituted with one or more $C_{1-6}$ alkyl or heterocyclyl; and n is 0, 1, 2, 3, or 4.

The groups, $R^1$, $R^2$, $R^3$, $R^4$, Q, and n in formulae described herein, including Formulae I, II, II-a, II-b, and II-c, are further defined herein. All combinations of the embodiments provided herein for such groups are within the scope of this disclosure.

In certain embodiments, $R^1$ is $C_{6-14}$ aryl, optionally substituted with one or more substituents Q. In certain embodiments, $R^1$ is $C_{6-14}$ aryl, optionally substituted with one or more substituents Q, wherein each Q independently selected from halo, $C_{1-6}$ alkyl, heteroaryl, and heterocyclyl, where the alkyl, heteroaryl, and heterocyclyl are each optionally substituted with one or more $C_{1-6}$ alkyl. In certain embodiments, $R^1$ is $C_{6-14}$ aryl, optionally substituted with one or more substituents Q, wherein each substituent Q is independently selected from chloro, methyl, piperazinyl, pyrrolyl, and morpholinyl, wherein each optionally substituted with one or more $C_{1-6}$ alkyl.

In certain embodiments, $R^1$ is $C_{6-14}$ aryl, optionally substituted with one or more substituents Q. In certain embodiments, $R^1$ is $C_{6-14}$ aryl, optionally substituted with one or more substituents Q, wherein each Q independently selected from halo, alkylamido, cyano, $C_{1-6}$ alkyl, $C_{1-6}$ alkoxy, heteroaryl, and heterocyclyl, where the alkyl, alkoxy, heteroaryl, and heterocyclyl are each optionally substituted with one or more halo, $C_{1-6}$ alkyl, aralkyl, dialkylamino, heterocyclyl, heterocyclylalkyl, or heterocyclylcarbonyl. In certain embodiments, $R^1$ is $C_{6-14}$ aryl, optionally substituted with one or more substituents Q, wherein each substituent Q is independently selected from chloro, fluoro, acetamido, cyano, methyl, methoxy, tert-butyl, imidazolyl, indazolyl, piperazinyl, piperidinyl, pyridinyl, pyrrolyl, morpholinyl, 1,1-dioxidothiomorpholinyl, pyrrolidinylmethyl, morpholinomethyl, dimethylamino, oxazolyl, pyrazolyl, (piperidinecarbonyl)piperazinyl, acetamido, (pyrimidinyl)piperizinyl, piperidinylmethyl, thiomorpholinyl, fluorophenylamido, methoxyphenylamido, isopropylpiperidinyl, cyanomethyl, (trifluoromethyl)phenylamido, and oxomorpholinyl, wherein each substituent Q optionally substituted with one or more halo, $C_{1-6}$ alkyl, aryl, cyano, oxo, dialkylamino, heterocyclyl, and heterocyclylcarbonyl.

In certain embodiments, $R^1$ is phenyl, optionally substituted with one or more substituents Q. In certain embodiments, $R^1$ is phenyl, optionally substituted with one, two, three, four, or five substituents Q. In certain embodiments, $R^1$ is phenyl, optionally substituted with one, two, three, four, or five substituents Q, wherein each substituent Q is independently selected from halo, $C_{1-6}$ alkyl, heteroaryl, and heterocyclyl, where the alkyl, heteroaryl, and heterocyclyl are each optionally substituted with one or more $C_{1-6}$ alkyl. In certain embodiments, $R^1$ is phenyl, optionally substituted with one, two, three, four, or five substituents Q, wherein each substituent Q is independently selected from chloro, methyl, piperazinyl, morphoplinyl, wherein each each optionally substituted with one or more $C_{1-6}$ alkyl. In certain embodiments, $R^1$ is 3-methyl-4-morpholinophenyl, 3-chloro-4-morpholinophenyl, 4-morpholinophenyl, 4-(2,6-dimethylmorpholino)phenyl, 4-(1H-pyrrol-1-yl)phenyl, 4-(4-isopropylpiperazin-1-yl)phenyl, 4-(pyridin-2-yl)phenyl, (4-methylpiperazin-1-yl)phenyl, 3-chloro-4-(2,6-dimethylmorpholino)phenyl, 4-(pyridin-3-yl)phenyl, or 3-chloro-4-(4-isopropylpiperazin-1-yl)phenyl.

In certain embodiments, $R^1$ is phenyl, optionally substituted with one or more substituents Q. In certain embodiments, $R^1$ is phenyl, optionally substituted with one, two, three, four, or five substituents Q. In certain embodiments, $R^1$ is phenyl, optionally substituted with one, two, three, four, or five substituents Q, wherein each substituent Q is independently selected from halo, $C_{1-6}$ alkyl, heteroaryl, and heterocyclyl, halo, $C_{1-6}$ alkyl, $C_{1-6}$ alkoxy, heteroaryl, and heterocyclyl, where the alkyl, alkoxy, heteroaryl, and heterocyclyl are each optionally substituted with one or more halo, $C_{1-6}$ alkyl, aralkyl, dialkylamino, heterocyclyl, heterocyclylalkyl, or heterocyclylcarbonyl. In certain embodiments, $R^1$ is phenyl, optionally substituted with one, two, three, four, or five substituents Q, wherein each substituent Q is independently selected from chloro, fluoro, methyl, methoxy, tert-butyl, imidazolyl, indazolyl, piperazinyl, piperidinyl, pyridinyl, pyrrolyl, morpholinyl, and 1,1-dioxidothiomorpholinyl, wherein each substituent Q is optionally substituted with one or more halo, $C_{1-6}$ alkyl, aralkyl, heteroarylalkyl, heterocyclyl, or heterocylylcarbonyl. In certain embodiments, is 3-methyl-4-morpholinophenyl, 3-chloro-4-morpholinophenyl, 4-morpholinophenyl, 4-(2,6-dimethylmorpholino)phenyl, 4-(1H-pyrrol-1-yl)phenyl, 4-(4-isopropylpiperazin-1-yl)phenyl, 4-(pyridin-2-yl)phenyl, 4-(4-methylpiperazin-1-yl)phenyl, 3-chloro-4-(2,6-dimethylmorpholino)phenyl, 4-(pyridin-3-yl)phenyl, 3-chloro-4-(4-isopropylpiperazin-1-yl)phenyl, 1,1'-biphenyl, 4-(1H-imidazol-1-yl)phenyl, 4-methoxyphenyl, 4-tert-butylphenyl, 4-(4-methyl-[1,4'-bipiperidin]-1'-yl)phenyl, 4-(4-(morpholine-4-carbonyl)piperazin-1-yl)phenyl, 4-(4-fluoropiperidin-1-yl)phenyl, 4-(piperidin-1-yl)phenyl. 3-chloro-4-(2,6-dimethylmorpholino)phenyl, 3-methyl-4-(4-methylpiperazin-1-yl)phenyl, 3-methyl-4-(piperidin-1-yl)phenyl, 4-(4-benzylpiperazin-1-yl)-3-methylphenyl, 4-(1,1-dioxidothiomorpholino)phenyl, (5-(piperidin-1-yl)pyridine-2-yl)phenyl, 4-(4-chloropiperidin-1-yl)phenyl, 4-(pyrrolidin-1-ylmethyl)phenyl, 4-(4-(dimethylamino)piperidin-1-yl)phenyl, 3-fluoro-4-morpholinophenyl, 4-(oxazol-5-yl)phenyl, 4-(4-(piperidine-1-carbonyl)piperazin-1-yl)phenyl, 3-acetamidophenyl, 3-chloro-4-(4-methylpiperazin-1-yl)phenyl, 4-fluorophenyl, 3-cyanophenyl, 4-(4-(pyrimidin-2-yl)piperazin-1-yl)phenyl, 4-(piperidin-1-ylmethyl)phenyl, 4-thiomorpholinophenyl, 4-aminophenyl, 4-(aminosulfonyl)phenyl, 4-(dimethylamino)phenyl, 4-(morpholinomethyl)phenyl. 2-methoxyphenyl, 4-(4-fluorophenylamido)phenyl, 4-(4,5-dihydro-1H-pyrazol-3-yl)phenyl, 4-(2-methoxyphenylamido)phenyl, 4-(3-methoxyphenylamido)phenyl, 4-(4-methoxyphenylamido)phenyl, 4-(4-isopropylpiperidin-1-yl)phenyl 4-(3-oxomorpholinyl)phenyl, 4-(2-cyanomethyl)phenyl, 4-((4-trifluoromethyl)phenylamido)phenyl, or 4-(4-methylpiperidin-1-yl)phenyl.

In certain embodiments, $R^1$ is heteroaryl, optionally substituted with one or more substituents Q. In certain embodiments, $R^1$ is monocyclic heteroaryl, optionally substituted with one or more substituents Q. In certain embodiments, $R^1$ is 5- or 6-membered heteroaryl, optionally substituted with one or more substituents Q. In certain embodiments, $R^1$ is 5-membered heteroaryl, optionally substituted with one or more substituents Q. In certain embodiments, $R^1$ is 6-membered heteroaryl, optionally substituted with one or more substituents Q. In certain embodiments, $R^1$ is pyridinyl, optionally substituted with one or more substituents Q. In certain embodiments, $R^1$ is 2-morpholino-3-chloropyridin-5-yl, 2-morpholinopyridin-5-yl, 5-morpholinopyridin-2-yl, 2-morpholino-3-methylpyridin-5-yl, 2-(4-isopropylpiperazin-1-yl)-3-methylpyridin-5-yl, or 2-(4-methylpiperazin-1-yl)-3-methylpyridin-5-yl.

In certain embodiments, $R^1$ is heteroaryl, optionally substituted with one or more substituents Q. In certain embodiments, $R^1$ is monocyclic heteroaryl, optionally substituted with one or more substituents Q. $R^1$ is bicyclic heteroaryl, optionally substituted with one or more substituents Q. In certain embodiments, $R^1$ is 5- or 6-membered heteroaryl, optionally substituted with one or more substituents Q. In certain embodiments, $R^1$ is 5-membered heteroaryl, optionally substituted with one or more substituents Q. In certain embodiments, $R^1$ is 6-membered heteroaryl, optionally substituted with one or more substituents Q. In certain embodiments, $R^1$ is pyridinyl, optionally substituted with one or more substituents Q. In certain embodiments, $R^1$ is 2-morpholino-3-chloropyridin-5-yl, 2-morpholinopyridin-5-yl, 5-morpholinopyridin-2-yl, 2-morpholino-3-methylpyridin-5-yl, 2-(4-isopropylpiperazin-1-yl)-3-methylpyridin-5-yl, 2-(4-methylpiperazin-1-yl)-3-methylpyridin-5-yl, 1H-indazol-5-yl, 6-(2,6-dimethyltetrahydro-2H-pyran-4-yl)pyridin-3-yl, or 2-(4-(pyrrolidin-1-yl)piperidin-1-yl)pyridin-5-yl.

In certain embodiments, $R^2$ is $C_{1-6}$ alkyl, optionally substituted with one or more substituents Q. In certain embodiments, $R^2$ is $C_{3-10}$ cycloalkyl, optionally substituted with one or more substituents Q. In certain embodiments, $R^2$ is methyl.

In certain embodiments, $R^3$ is $C_{1-6}$ alkyl, optionally substituted with one or more substituents Q. In certain embodiments, $R^3$ is $C_{3-10}$ cycloalkyl, optionally substituted with one or more substituents Q. In certain embodiments, $R^3$ is methyl.

In certain embodiments, $R^4$ is halo. In certain embodiments, $R^4$ is flouro, chloro, or bromo. In certain embodiments, $R^4$ is $C_{1-6}$ alkyl. In certain embodiments, $R^4$ is heteroaryl, optionally substituted with one or more $C_{1-6}$ alkyl. In certain embodiments, $R^4$ is heterocyclyl, optionally substituted with one or more $C_{1-6}$ alkyl.

In certain embodiments, $R^4$ is halo. In certain embodiments, $R^4$ is flouro, chloro, or bromo. In certain embodiments, $R^4$ is cyano. In certain embodiments, $R^4$ is alkylamido. In certain embodiments, $R^4$ is acetamido. In certain embodiments, $R^4$ is arylamido. In certain embodiments, $R^4$ is amino. In certain embodiments, $R^4$ is dialkylamino. In certain embodiments, $R^4$ is aminosulfonyl. In certain embodiments, $R^4$ is $C_{1-6}$ alkyl. In certain embodiments, $R^4$ is $C_{1-6}$ alkyl substituted with one or more cyano. In certain embodiments, $R^4$ is heteroaryl, optionally substituted with one or more $C_{1-6}$ alkyl. In certain embodiments, $R^4$ is heterocyclyl, optionally substituted with one or more $C_{1-6}$ alkyl. In certain embodiments, $R^4$ is heterocyclyl, optionally substituted with one or more oxo.

In certain embodiments, n is 0. In certain embodiments, n is 1. In certain embodiments, n is 2. In certain embodiments, n is 3. In certain embodiments, n is 4. In certain embodiments, n is 5.

In one embodiment, the compound provided herein is selected from:
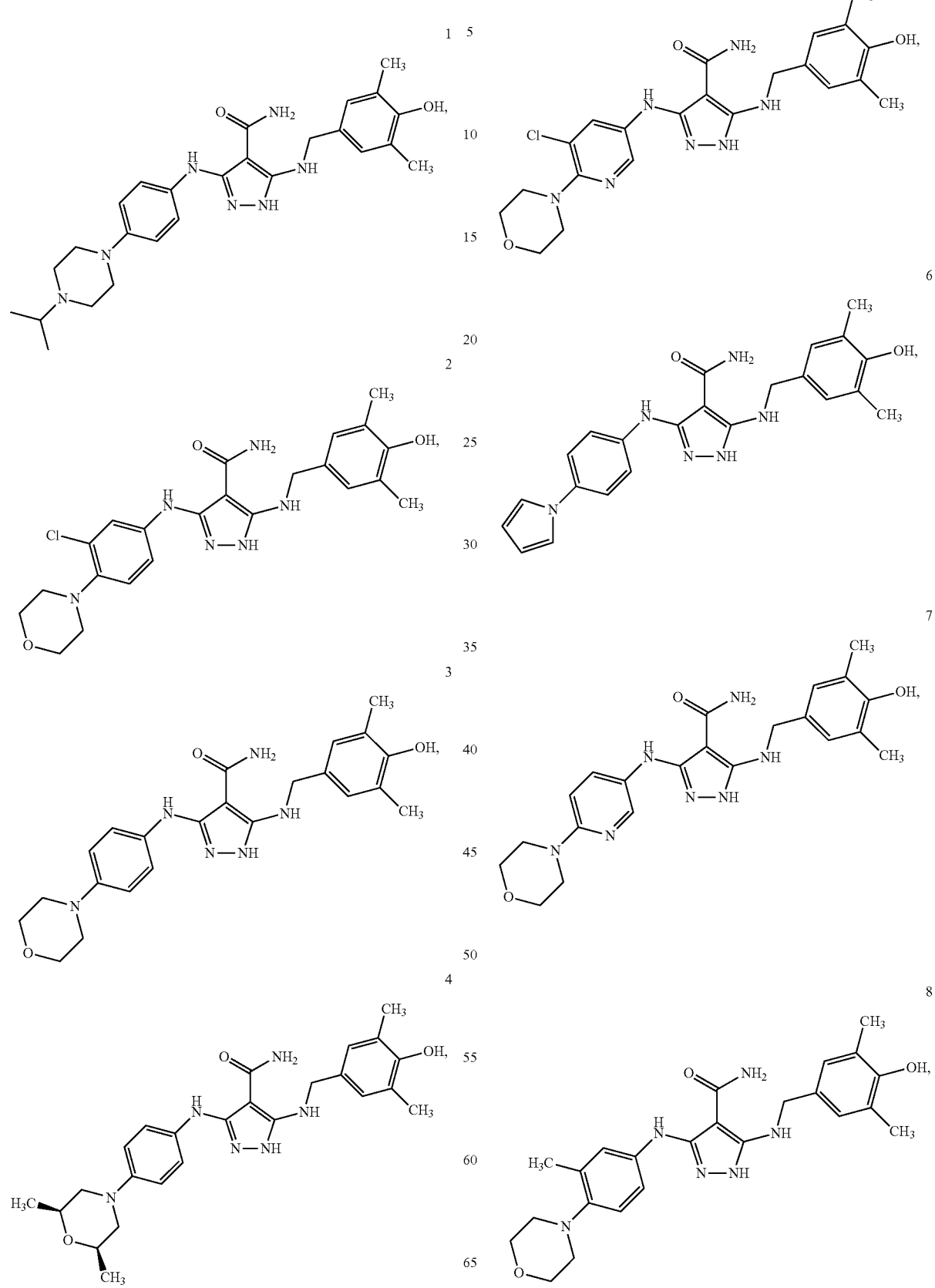

9
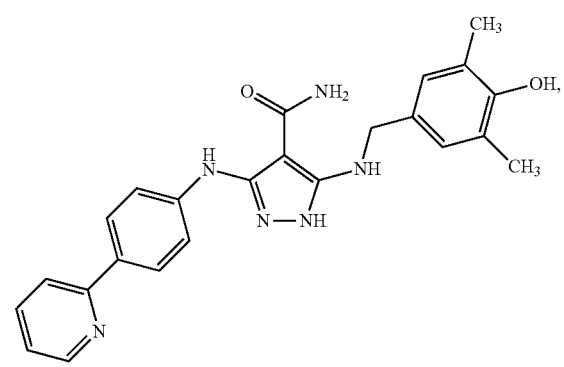
10
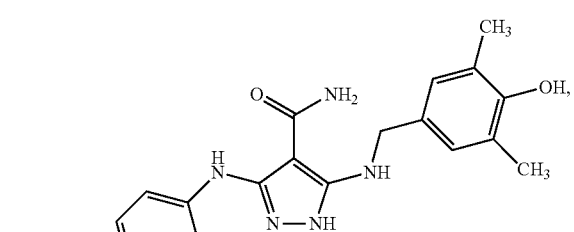
11
12
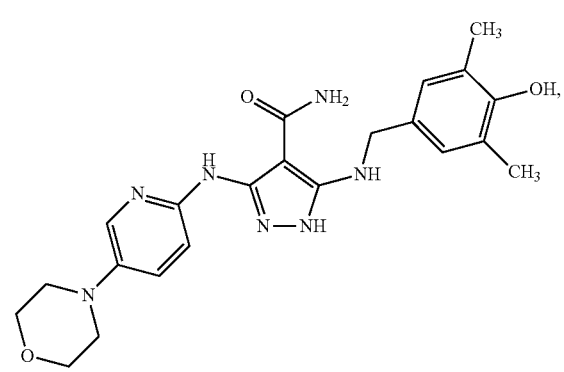
13
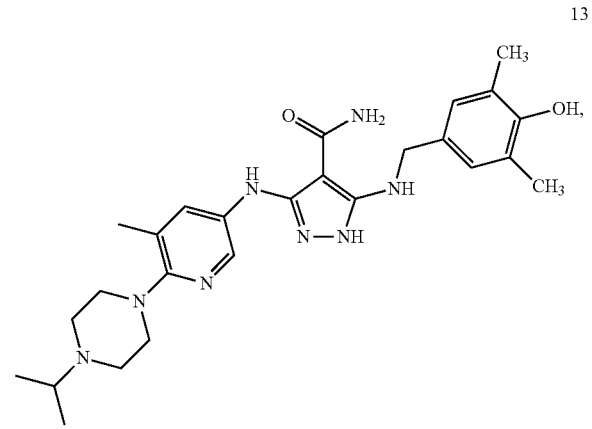 [SMILES: Cc1cc(CNc2[nH]nc(Nc3ccc(N4CCN(C(C)C)CC4)c(Cl)c3)c2C(N)=O)cc(C)c1O]
14
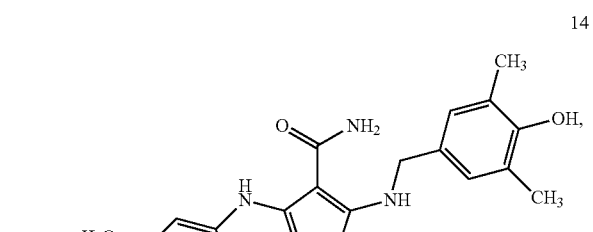
15
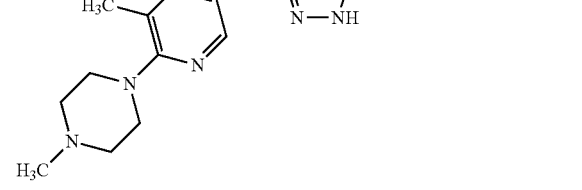
16
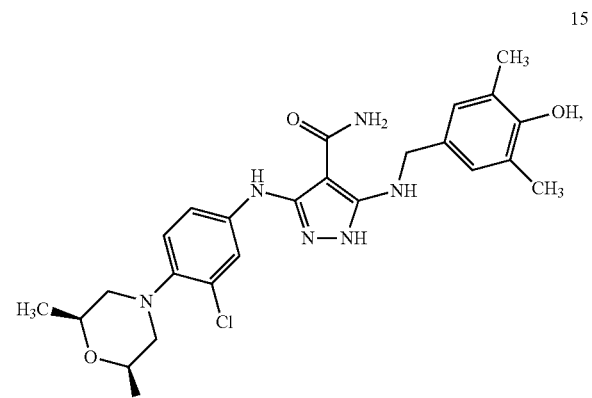

17
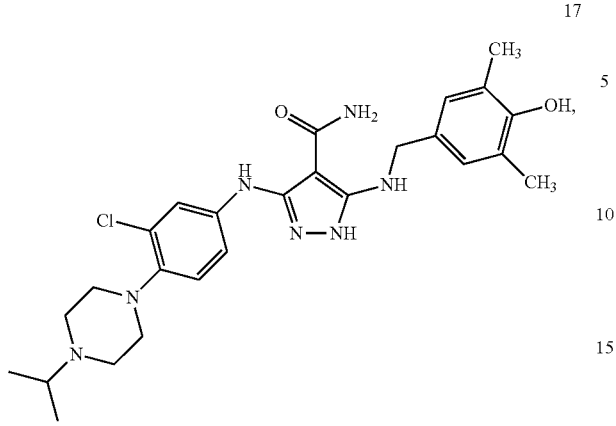
and stereoisomers, enantiomers, mixtures of enantiomers, mixtures of diastereomers, and isotopic variants thereof; and pharmaceutically acceptable salts, solvates, hydrates, and prodrugs thereof.
In one embodiment, the compound provided herein is selected from:
18
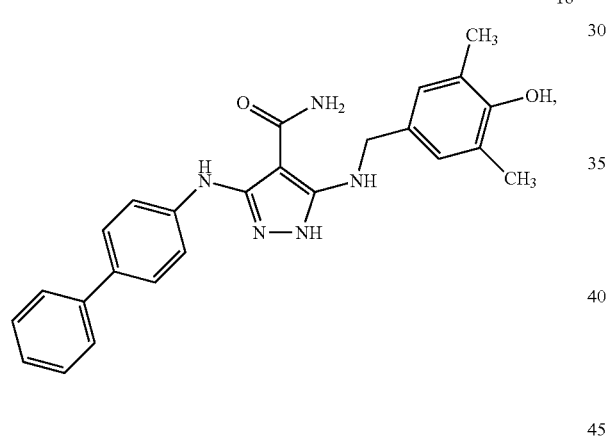
19
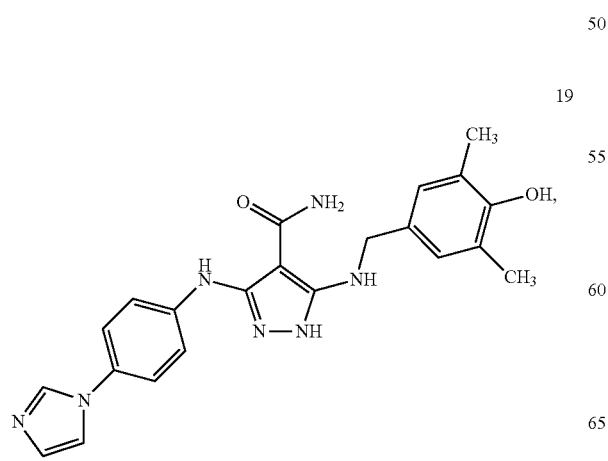
20
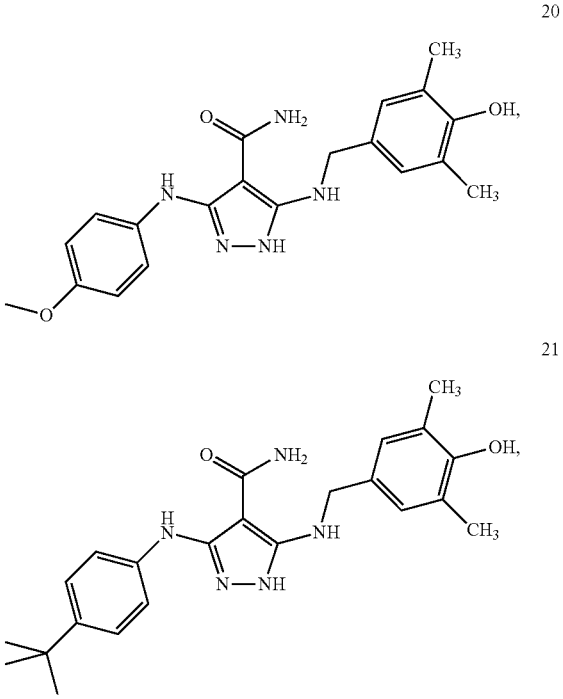
21
22
23
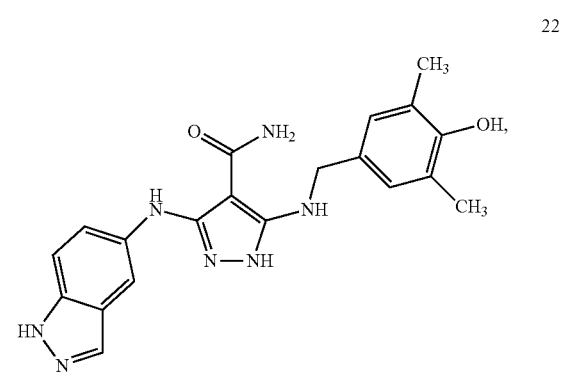
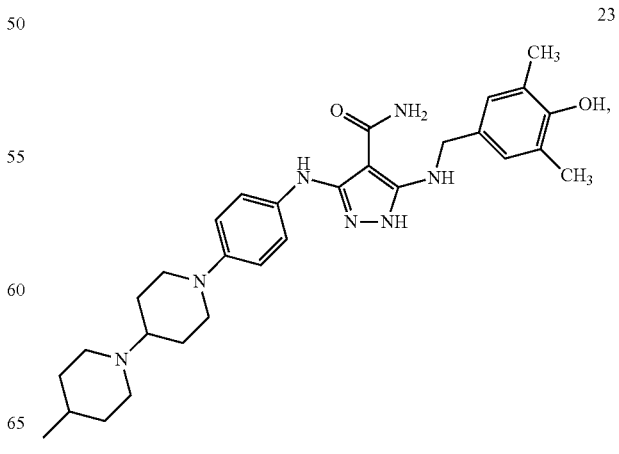

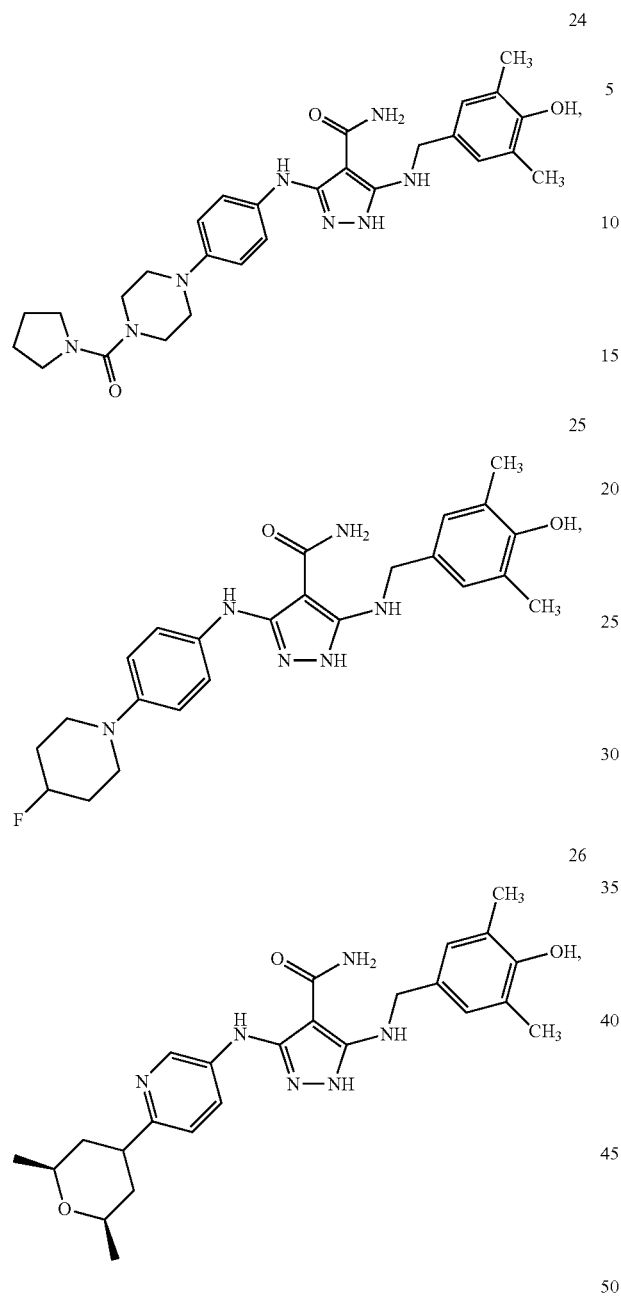
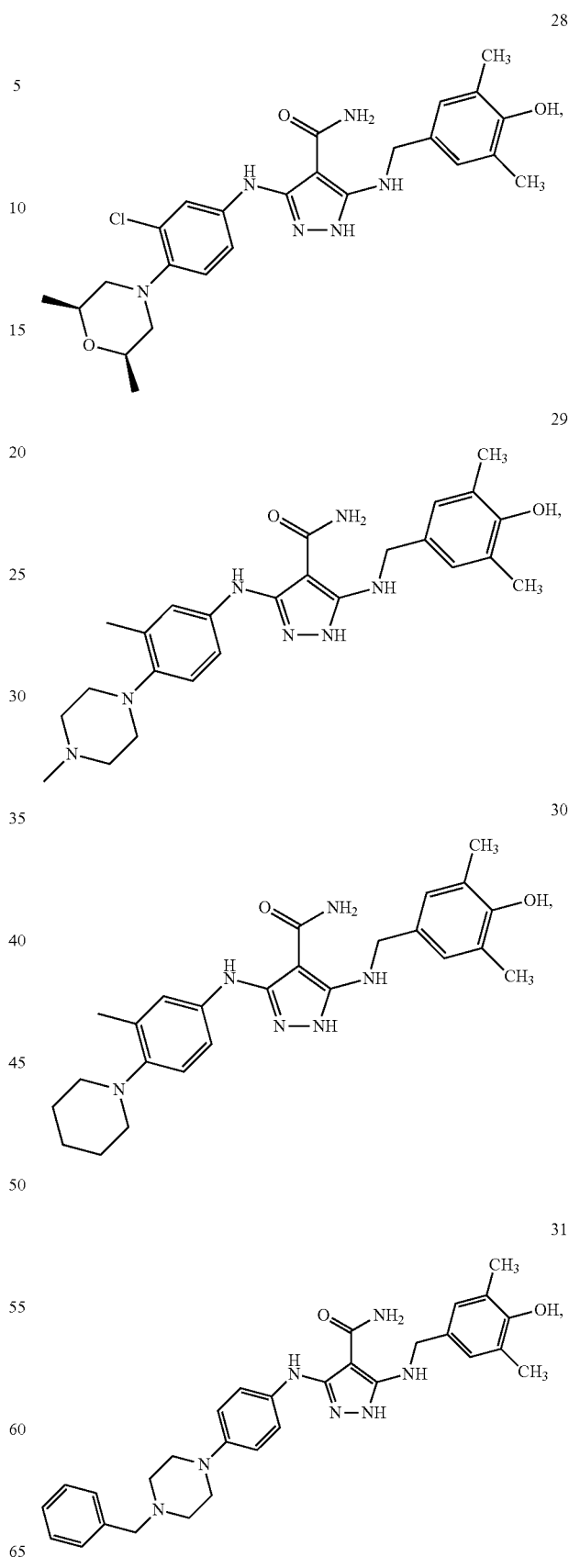

32
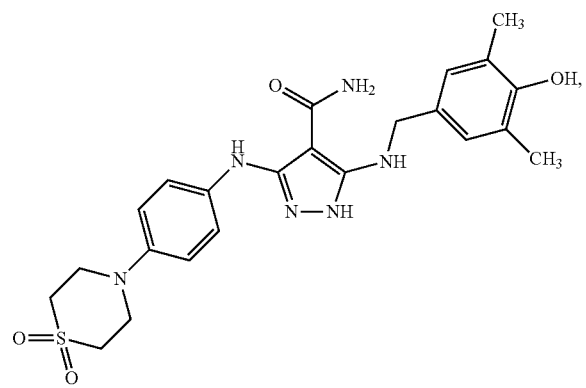
33
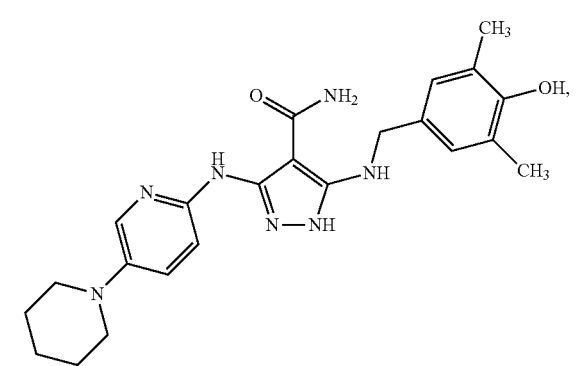
34
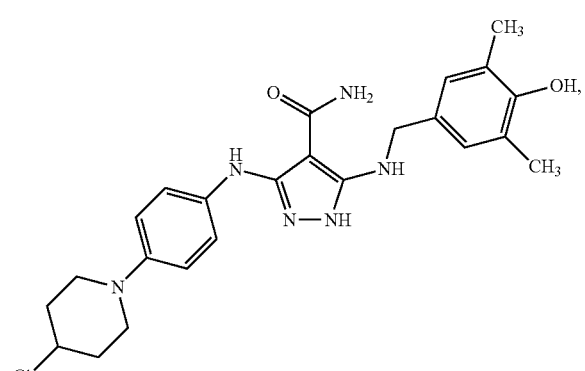
35
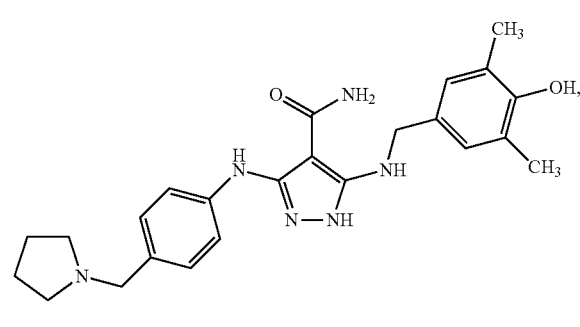
36
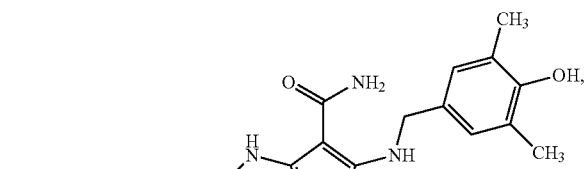
37
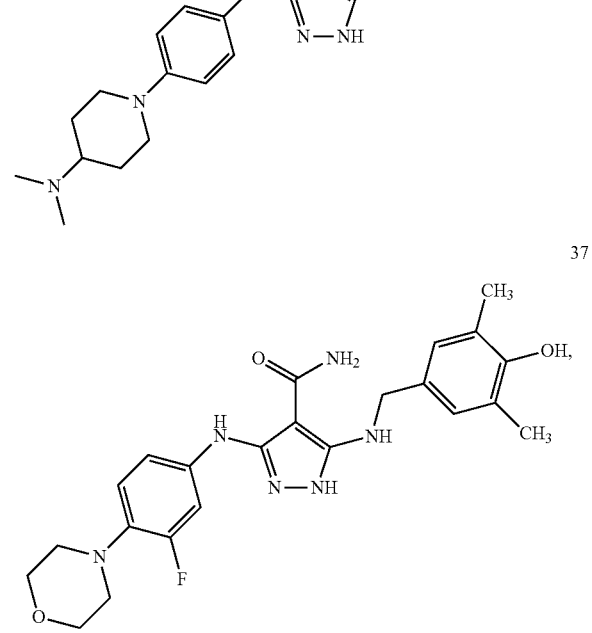
38
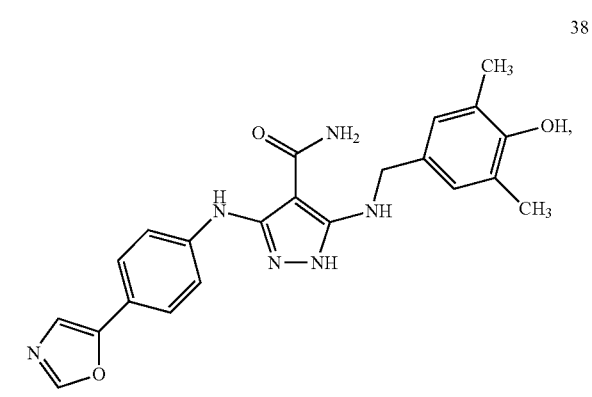
39
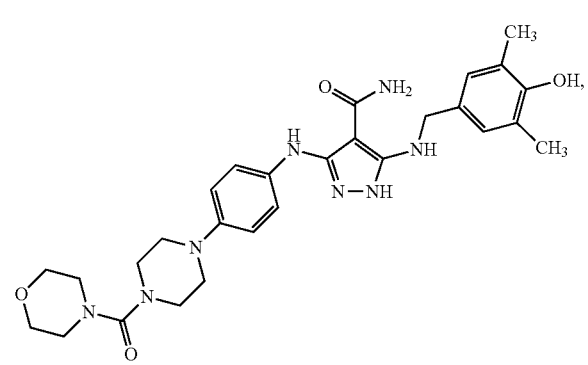

40
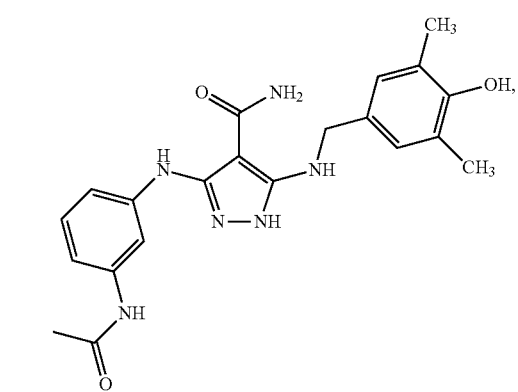
41
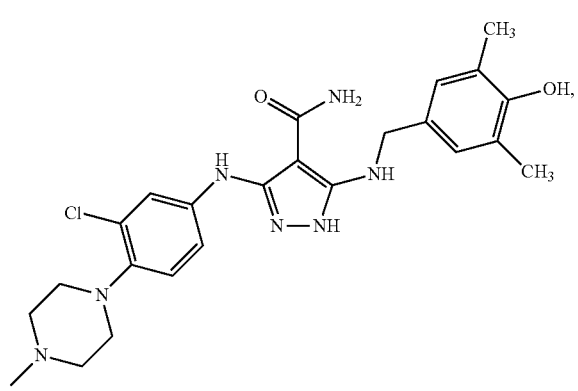
42
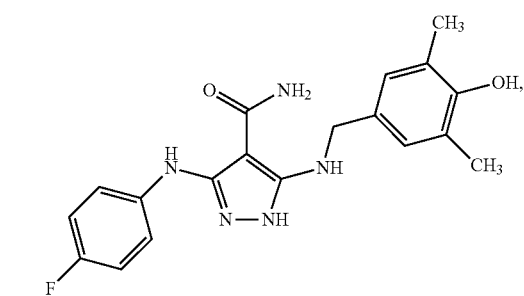
43
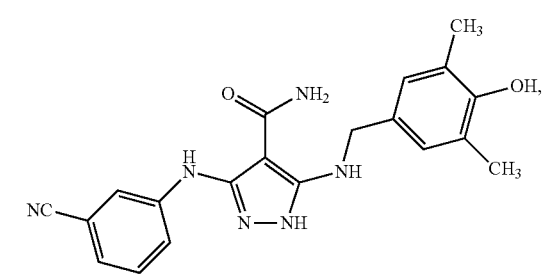
44
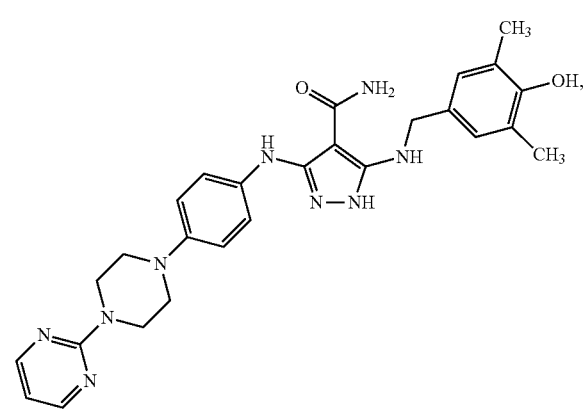
45
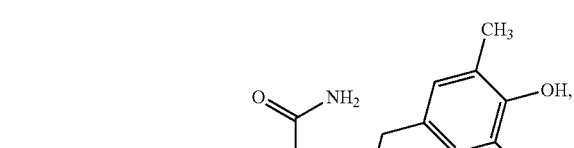
46
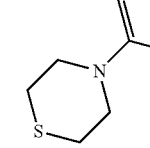
47

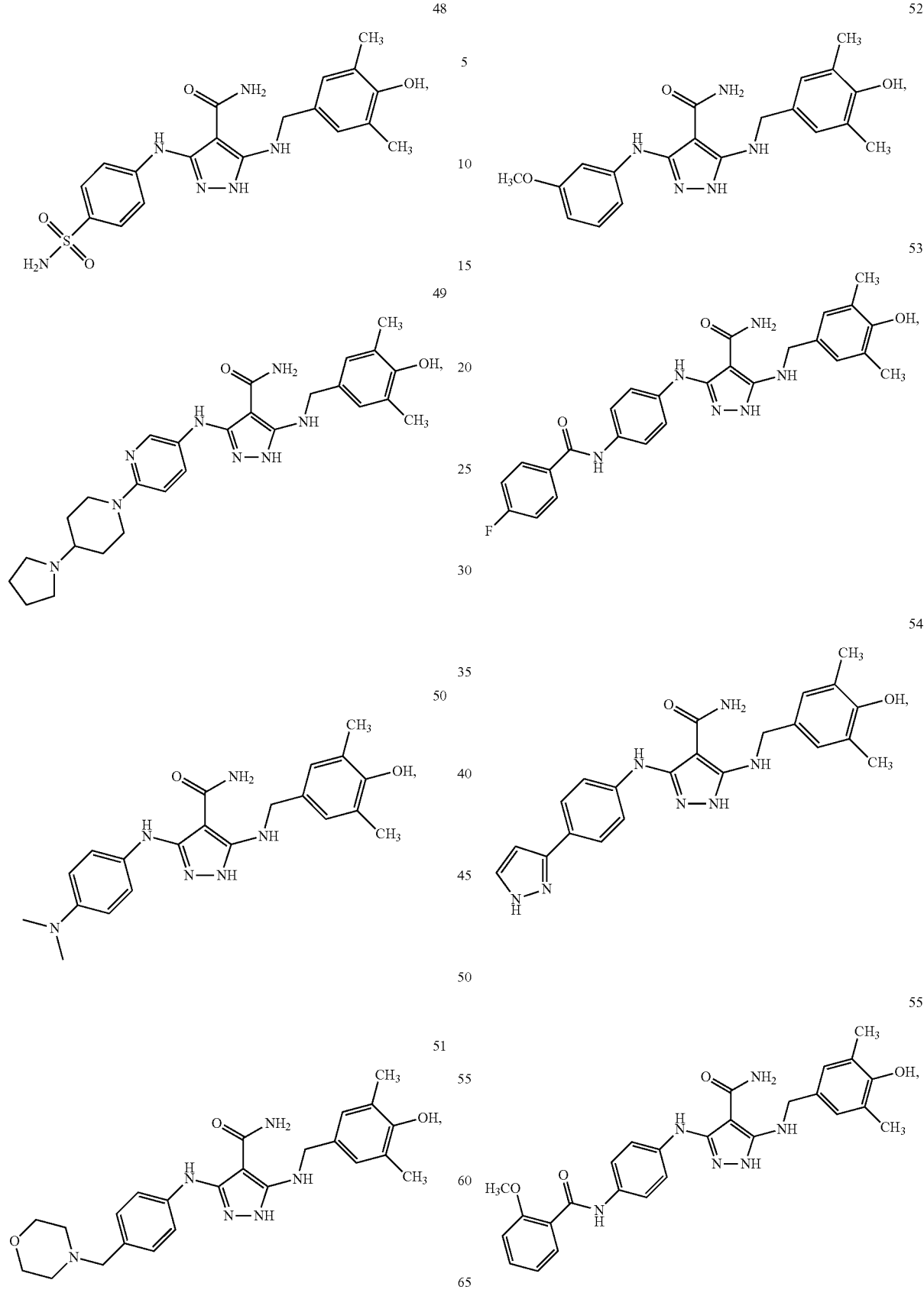

-continued

56
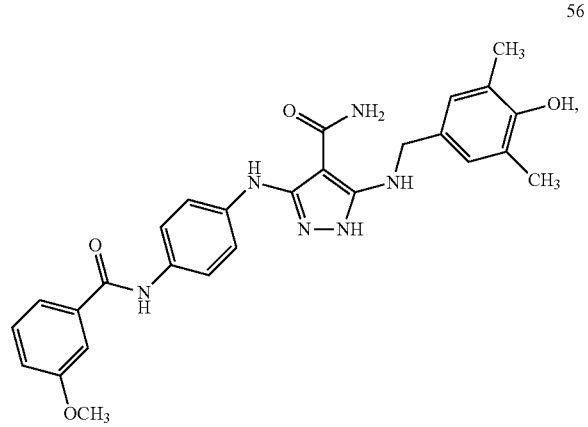

57
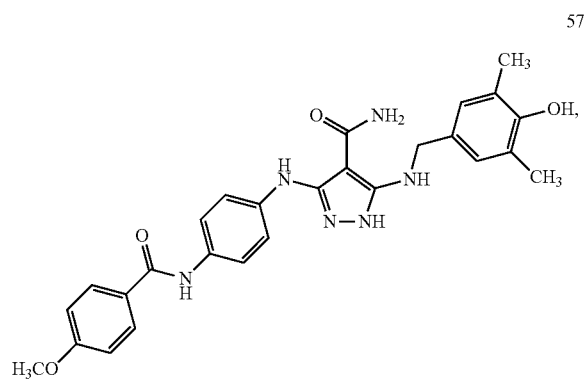

58
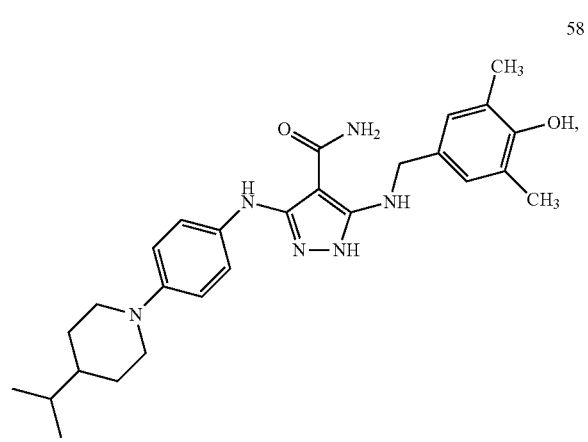

59
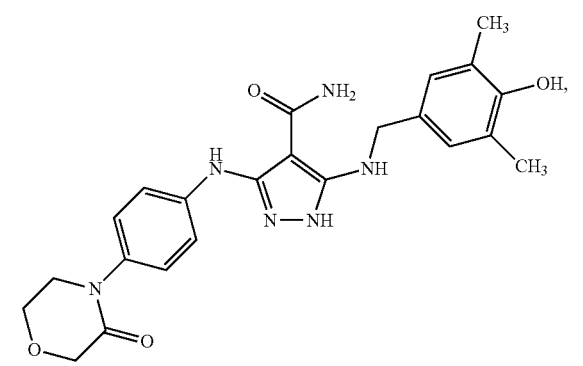

-continued

61
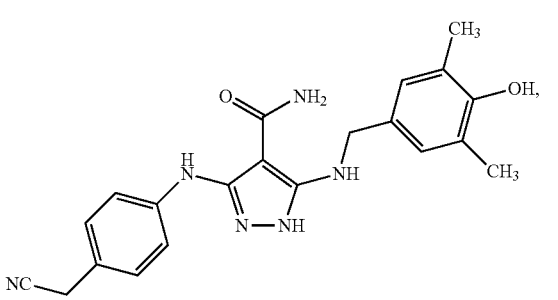

62
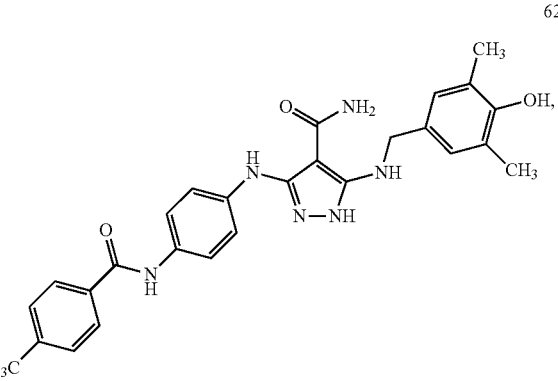

63
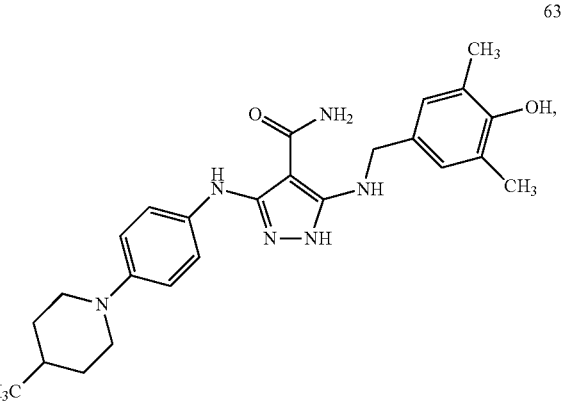

and stereoisomers, enantiomers, mixtures of enantiomers, mixtures of diastereomers, and isotopic variants thereof, and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or a mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs*, 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. USA* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *ChemMedChem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

Methods of Synthesis

The compounds provided herein can be prepared, isolated, or obtained by any method known to one of skill in the art; and the following examples are only representative and do not exclude other related methods and procedures. See also, U.S. patent application Ser. Nos. 13/830,486 and 13/830,712, the disclosure of each of which is incorporated herein by reference in its entirety.

In one embodiment, for example, a compound of Formula I can be prepared as shown in Scheme I. Compound I-1 is first converted to compound I-2 by reacting with carbon disulfide and dimethylsulfate. Compound I-2 then reacts with an amine, such as $R^1NH_2$, to form compound I-3. Alternatively, Compound I-3 may be made by reacting an isothiocyanate ($R^1NCS$) with Compound I-1 and methyl iodide. Subsequently, compound I-3 reacts with hydrazine to form compound I-4, which is then treated with a carbonyl compound, such as 4-hydroxy-3,5-dimethylbenzaldehyde, to form a compound of Formula I, e.g., compound I-5. The imine group of compound I-5 can be reduced with a reducing agent, e.g., sodium borohydride ($NaBH_4$) or sodium cyanoborohydride ($NaB(CN)H_3$), to form compound I-6.

Scheme II

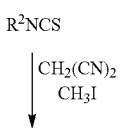

Scheme I

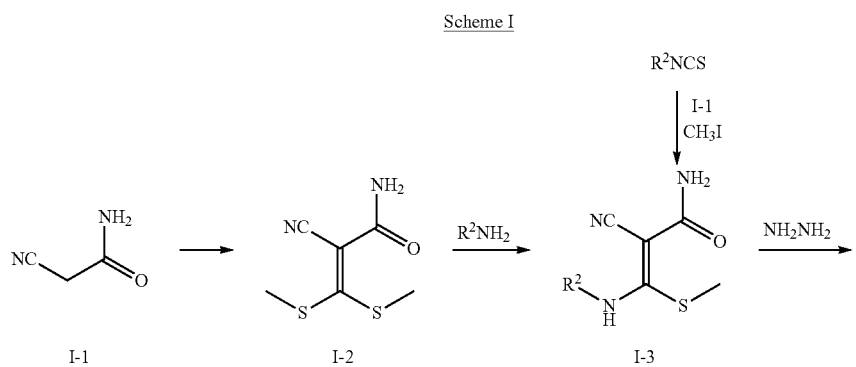

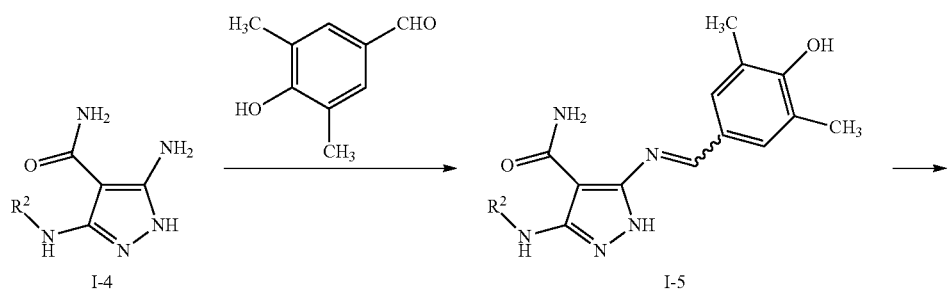

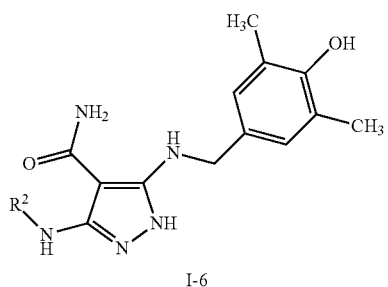

In another embodiment, for example, a compound of Formula I can be prepared as shown in Scheme II. Compound I-7 reacts an amine, such as $R^2NH_2$, to form compound I-8. Alternatively, compound I-8 can be made by reacting an isothiocyanate ($R^2NCS$) with malononitrile and methyl iodide. Compound I-8 is then treated with hydrazine to form compound I-9. The cyano group of compound I-9 is converted to aminocarbonyl, e.g., by reacting with hydrogen peroxide. Compound I-4 can then be converted into compounds I-5 and I-6 as described herein.

-continued

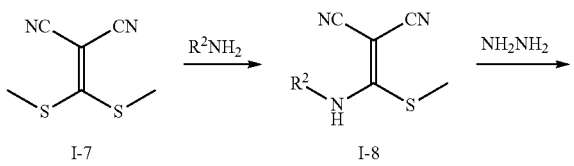

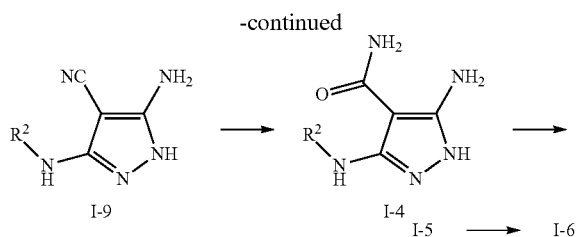

Pharmaceutical Compositions

Provided herein are pharmaceutical compositions comprising a compound provided herein, e.g., a compound of Formula I, as an active ingredient, including a stereoisomer, enantiomer, mixture of enantiomers, mixture of diastereomers, or isotopic variant thereof; or a pharmaceutically acceptable salt, solvate, hydrate, or prodrug thereof; and a pharmaceutically excipient.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

In another embodiment, the pharmaceutical compositions are provided in a dosage form for parenteral administration, which comprise a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

In yet another embodiment, the pharmaceutical compositions are provided in a dosage form for topical administration, which comprise a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-3-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. DrugDeliv.*

2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS Pharm Sci Tech.* 2008, 9, 635-638; Chrzanowski, *AAPS Pharm Sci Tech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein is a method of treating, preventing, or ameliorating one or more symptoms of a RC kinase-mediated disorder, disease, or condition in a subject, comprising administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In another embodiments, provided herein is a method of treating, preventing, or ameliorating one or more symptoms of a disorder, disease, or condition responsive to the modulation of RC kinase activity in a subject, administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In yet another embodiments, provided herein is a method of treating, preventing, or ameliorating one or more symptoms of a disorder, disease, or condition responsive to the inhibition of RC kinase activity in a subject, administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In yet another embodiment, provided herein is a method for treating, preventing, or ameliorating one or more symptoms of an eosinophil-related disorder, disease, or condition in a subject, comprising administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In yet another embodiment, provided herein is a method for treating, preventing, or ameliorating one or more symptoms of a basophil-related disorder, disease, or condition in a subject, comprising administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In yet another embodiment, provided herein is a method for treating, preventing, or ameliorating one or more symptoms of a mast cell-related disorder, disease, or condition in a subject, comprising administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In still another embodiment, provided herein is a method for treating, preventing, or ameliorating one or more symptoms of an inflammatory disease in a subject, comprising administering to the subject a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In one embodiment, the subject is a mammal. In another embodiment, the subject is a human.

The disorders, diseases, or conditions treatable with a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disorder, disease, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease (COPD), Churg-Strauss syndrome, sinusitis, basophilic leukemia, chronic urticaria, basophilic leukocytosis, eczema, arthritis, rheumatoid arthritis, psoriatic arthritis, and osteoarthritis.

In certain embodiments, the disorder, disease, or condition is asthma, exercise induced asthma, allergic rhinitis, atopic dermatitis, chronic obstructive plumonary disease, or allergic conjunctivitis. In certain embodiments, the disorder, disease, or condition is COPD.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided herein is administration of the compounds or pharmaceutical compositions provided herein in a depot formulation, in which the active ingredient is released over a predefined time period.

In the treatment, prevention, or amelioration of one or more symptoms of the disorders, diseases, and conditions, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day. In certain embodiments, the dosage level is ranging from about 0.001 to about 100 mg/kg per day. In certain embodiments, the dosage level is ranging from about 0.01 to about 75 mg/kg per day. In certain embodiments, the dosage level is ranging from about 0.1 to about 50 mg/kg per day. In certain embodiments, the dosage level is ranging from about 0.5 to about 25 mg/kg per day. In certain embodiments, the dosage level is ranging from about 1 to about 20 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, provided herein are methods of modulating RC kinase activity, comprising contacting a RC kinase with a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof. In one embodiment, the RC kinase is expressed by a cell.

The compounds provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof; can also be combined or used in combination with other agents useful in the treatment, prevention, or amelioration of one or more symptoms of the disorders, diseases, or conditions for which the compounds provided herein are useful, including, but not limited to, asthma, COPD, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted herein.

In certain embodiments, the compounds provided herein can be combined with one or more steroidal drugs known in the art, including, but not limited to, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to, amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to, amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to, acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to, anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as paclitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

Such other agents, or drugs, can be administered, by a route and in an amount commonly used therefor, simultaneously or sequentially with the compounds provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof.

In certain embodiments, the kit includes a container comprising a dosage form of the compound provided herein, e.g., a compound of Formula I, including a stereoisomer, enantiomer, mixture of enantiomers, mixture of diastereomers, or isotopic variant thereof; or a pharmaceutically acceptable salt, solvate, hydrate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); L (liter); mM (millimolar); μM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); ACN (acetonitrile); CDCl$_3$ (deuterated chloroform); DCM (dichloromethane); DMF (N,N-dimethylformamide); DMSO (dimethylsulfoxide); DMSO-d$_6$ (deuterated dimethylsulfoxide); EtOAc (ethyl acetate); EtOH (ethanol); Et$_2$O (diethylether); MeOH (methanol); PE (petroleum ether); TBDME (tert-butyldimethylether); THF (tetrahydrofuran); DIPEA (N,N-diisopropylethylamine); TEA (triethylamine); DBU (1,8-diazabicyclo[5.4.0]undec-7-ene); DMAP (4-dimethylaminopyridine); AIBN (1,1'-azobis(cyclohexanecarbonitrile); CDI (carbonyldiimidazole); EDCI or EDC (N'-ethyl-N-(3-dimethylaminopropyl)-carbodiimide); TBTU (O-(benzotriazol-1-yl)-N,N,N',N'-tetramethyluronium tetrafluoroborate); Me (methyl); Et (ethyl); iPr (isopropyl); tBu (tert-butyl); Boc (tert-butoxylcarbonyl); Cbz (benzylcarbomate); Fmoc (9-fluorenylmethyl carbomate); Bn (benzyl); PMB (para-methoxy benzyl); Bs (4-bromo-benzenesulfonyl); TMS (trimethylsilyl); TsOH (tosylic acid); TsO (tosylate); DEAD (diethylazodicarboxylate), DIAD (diisopropylazodicarboxylate); AcCl (acetyl chloride); TFA (trifluoroacetic acid); TBAF (tetra-n-butylammonium fluoride); and tBuOK (potassium tert-butoxide).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure. Examples of related syntheses may be found, e.g., in U.S. patent application Ser. Nos. 13/830,486 and 13/830,712, the disclosure of each of which is incorporated herein by reference in its entirety.

The starting materials used in the examples described herein are either commercially available or can be prepared by a method known to one of skill in the art.

Example 1

5-((4-hydroxy-3, 5-dimethylbenzyl)amino)-3-((4-(4-isopropylpiperazin-1-yl)phenyl)amino)-1H-pyrazole-4-carboxamide 1

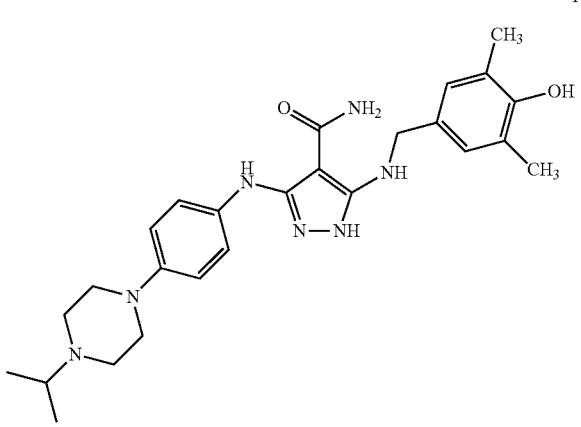

Compound 1 was prepared according to Scheme 1.

Scheme 1

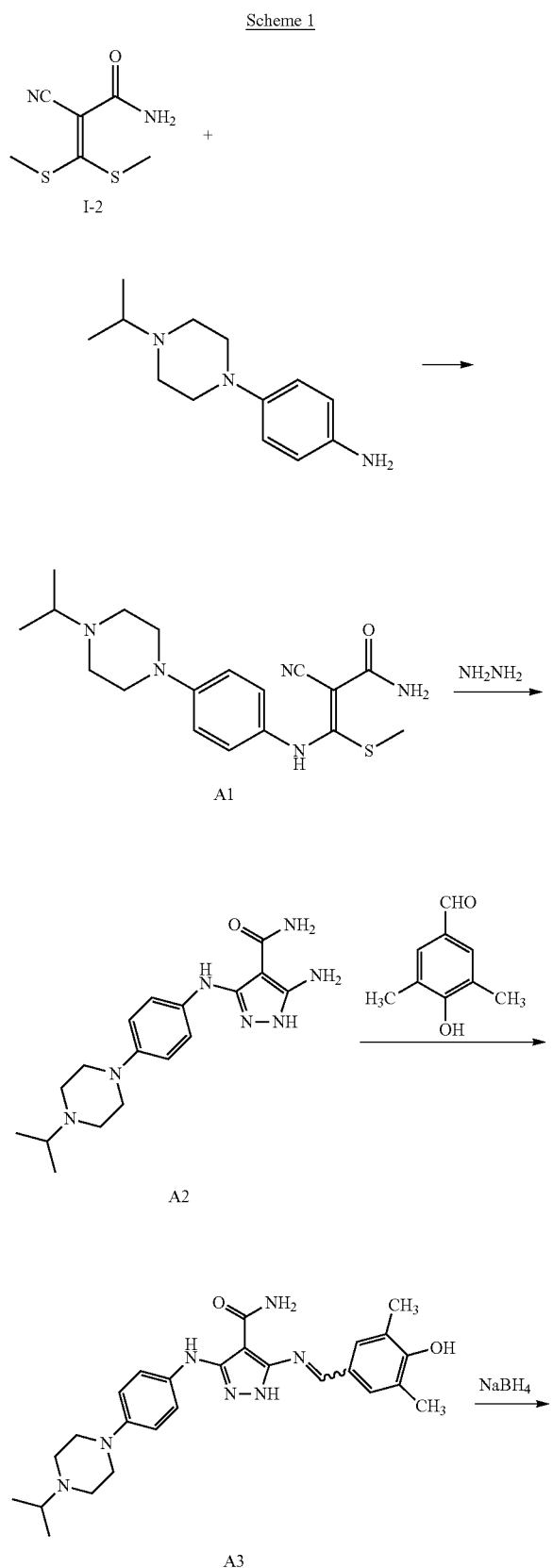

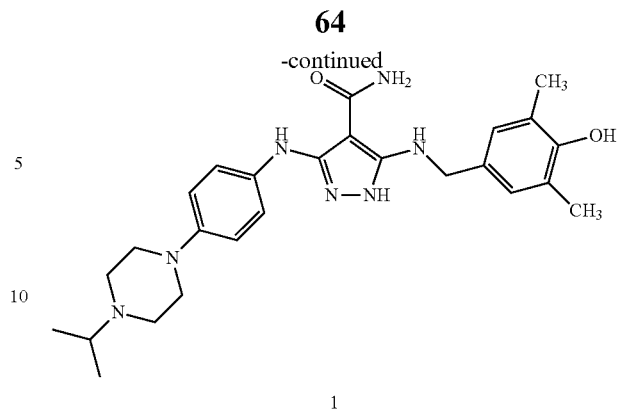

Preparation of 2-cyano-3,3-bis(methylthio)acrylamide I-2

A mixture of 2-cyanoacetamide (10 g, 118.9 mmol) and potassium hydroxide (6.661 g, 118.9) in ACN (100 mL) was stirred at room temperature for 1 hr followed by slow addition of carbon disulfide (9.054 g, 118.9 mmol) at room temperature. After the solution was stirred for 3 hrs at room temperature, dimethylsulfate (19.5 g, 154.6 mmol) was added and the reaction mixture was stirred overnight at room temperature. The volatiles were then removed under vacuum, and the residual was redissolved in EtOAc and washed sequentially with water and brine, dried over anhydrous MgSO$_4$, and concentrated in vacuo. The resulting solid was triturated with EtOAc/hexanes, filtered, and dried to give compound I-2 (9.4 g, 42% yield, 99.0% purity) as a yellow solid.

2-cyano-3,3-bis(methylthio)acrylamide I-2 (0.500 g) was dissolved in 15 mL EtOH and 4-(4-(2-propyl)-piperazin-1-yl)aniline (1.0 eq.) was added. The reaction was stirred at 75° C. until the starting amide was absent by HPLC. Once complete (18 hrs), reaction was brought to room temperature and filtered to obtain 2-cyano-3-((4-(4-isopropylpiperazin-1-yl)phenyl)amino)-3-(methylthio)acrylamide A1 as a purple powder. The product was allowed to dry under vacuum for 1 hr.

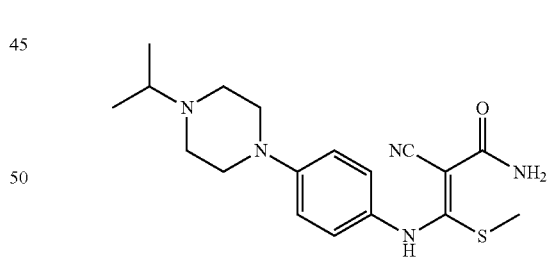

2-cyano-3-((4-(4-isopropylpiperazin-1-yl)phenyl)amino)-3-(methylthio)acrylamide A1

2-cyano-3-((4-(4-isopropylpiperazin-1-yl)phenyl)amino)-3-(methylthio)acrylamide A1 was then suspended in 10 mL EtOH and hydrazine hydrate (1.0 eq.) was added dropwise. The reaction was heated at 75° C. until A1 was absent (HPLC). Once the intermediate was absent (18 hrs), the reaction was brought to room temperature and filtered to obtain 5-amino-3-((4-(4-isopropylpiperazin-1-yl)phenyl)amino)-1H-pyrazole-4-carboxamide A2 as a purple powder. The product was allowed to dry under vacuum for 1 hr.

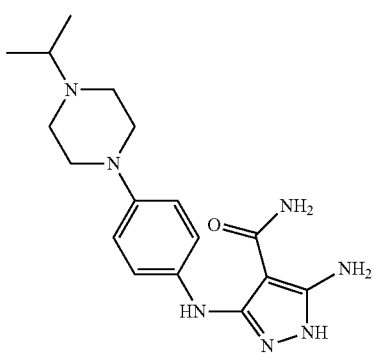 [SMILES: CC(C)N1CCN(c2ccc(Nc3n[nH]c(N)c3C(N)=O)cc2)CC1]

5-amino-3-((4-(4-isopropylpiperazin-1-yl)phenyl)amino)-1H-pyrazole-4-carboxamide A2

5-amino-3-((4-(4-isopropylpiperazin-1-yl)phenyl)amino)-1H-pyrazole-4-carboxamide (0.200 g) A2 was suspended in EtOH (4 mL) and piperidine (5 drops). The reaction mixture was heated at 80° C. while stirring, and 3,5-dimethyl-4-hydroxybenzaldehyde (0.122 g) was added. After 18 h, the reaction mixture was cooled to room temperature. The separated solids was collected by suction filtration and rinsed with ethanol to give the crude imine product A3, which was used without purification.

To a suspension of A3 (246 mg) in DMF (2 mL) and MeOH (4 mL) was slowly added sodium borohydride (39 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 1 (75 mg, 95.1% purity) as a powder. $^1$H-NMR (500 MHz, DMSO): 11.36 (s, 1H), 8.22 (s, 1H), 8.13 (s, 1H), 7.12 (s, 2H), 6.91 (s, 2H), 6.79 (d, J=8 Hz, 2H), 6.12 (s, 3H), 4.16 (d, J=8 Hz, 2H), 2.97 (m, 4H), 2.67 (m, 1H), 2.55 (m, 4H), 2.18 (s, 6H), 1.00 (s, 6H).

Example 2

Synthesis of 3-((3-chloro-4-morpholinophenyl)amino)-5-((4-hydroxy-3,5-dimethylbenzyl)amino)-1H-pyrazole-4-carboxamide 2

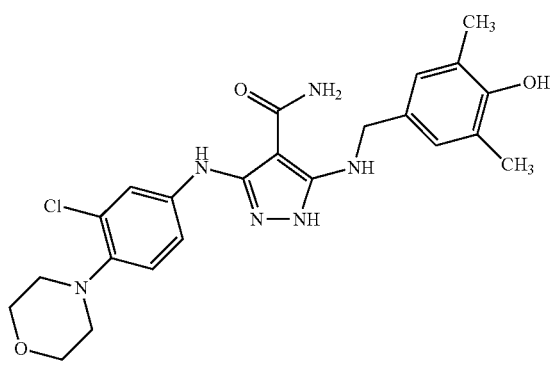

The intermediate 5-amino-3-((3-chloro-4-morpholinophenyl)amino)-1H-pyrazole-4-carboxamide was prepared in a manner substantially similar to that described for A2 of Example 1.

5-amino-3-((3-chloro-4-morpholinophenyl)amino)-1H-pyrazole-4-carboxamide (530 mg, 1.57 mmol) and 3,5-dimethyl-4-hydroxybenzaldehyde (0.285 g, 1.90 mmol, 1.2 eq.) were suspended in EtOH (9 mL) and piperidine (5 drops) was added. The reaction mixture was heated at 80° C. for 18 h and then cooled to room temperature. The separated precipitate was collected by suction filtration and rinsed with ethanol to give the crude imine as yellow powder.

To a suspension of imine (312 mg, 0.67 mmol) in DMF (15 mL) and MeOH (3 mL) was slowly added sodium borohydride (51 mg, 1.34 mmol, 2.0 eq.) at room temperature. After the reaction mixture was stirred at room temperature for 30 minutes, water (100 mL) was added until a clear solution was obtained. To the resulting stirring solution, HCl (3.0 N) was added dropwise until the precipitate persisted. Stirring was continued on an ice bath for 1 h. The resulting precipitate was filtered, washed with water, and dried to yield compound 2 (291 mg. 93% yield, 95.7% purity) as a white powder. $^1$H-NMR (500 MHz, DMSO): 11.47 (s, 1H), 8.54 (s, 1H), 7.51 (s, 1H), 7.04 (s, 2H), 6.92 (s, 2H), 6.68 (m, 3H), 4.17 (m, 2H), 3.71 (m, 4H), 2.86 (m, 4H), 2.14 (s, 6H).

Example 3

Synthesis of 5-((4-hydroxy-3,5-dimethylbenzyl)amino)-3-((4-morpholinophenyl)amino)-1H-pyrazole-4-carboxamide 3

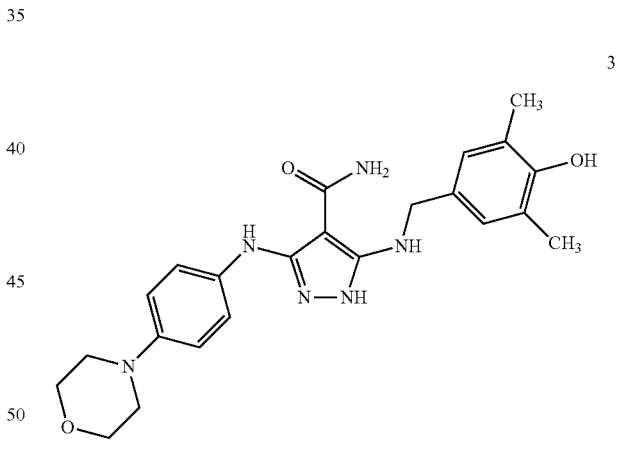

The intermediate 5-amino-3-((4-morpholinophenyl)amino)-1H-pyrazole-4-carboxamide was prepared in a manner substantially similar to that described for A2 of Example 1.

5-amino-3-((4-morpholinophenyl)amino)-1H-pyrazole-4-carboxamide (1.06 g, 3.51 mmol) and 3,5-dimethyl-4-hydroxybenzaldehyde (0.790 g, 5.26 mmol, 1.5 eq.) were suspended in EtOH (25 mL) and acetic acid (2.5 mL). The reaction mixture was heated at 80° C. for 24 h and then cooled to room temperature and concentrated in vacuo to approximately half of the original volume. The separated precipitate was collected by suction filtration and rinsed with ethanol to give the crude imine as an orange powder.

To a solution of imine (1.36 g, 3.13 mmol) in DMSO (15 mL) and MeOH (3 mL) was slowly added sodium borohydride (180 mg, 6.26 mmol, 2.0 eq.) at room temperature. After the reaction mixture was stirred at room temperature for 48 hours, water was added and the resulting precipitate was isolated by suction filtration and washed with water. The recovered precipitate was dissolved in DMSO (6 mL), filtered through a cotton plug, which was further rinsed with EtOH (3 mL). The DMSO and EtOH filtrates were combined, and water was added until a precipitate formed. The resulting suspension was chilled in a refrigerator for 3 hours. The resulting precipitate was filtered, washed with water, and dried to yield compound 3 (1.125 g. 82% yield, 97% purity) as a white powder. $^1$H-NMR (500 MHz, DMSO): 11.37 (s, 1H), 8.26 (s, 1H), 8.13 (s, 1H), 7.14 (m, 2H), 6.92 (s, 2H), 6.81 (d, J=8 Hz, 2H), 6.63 (s, 2H), 4.16 (d, J=8 Hz, 2H), 3.71 (m, 4H), 2.96 (m, 4H), 2.14 (s, 6H).

Example 4

Synthesis of 3-((4-(2,6-dimethylmorpholino)phenyl) amino)-5-((4-hydroxy-3,5-dimethylbenzyl)amino)-1H-pyrazole-4-carboxamide 4

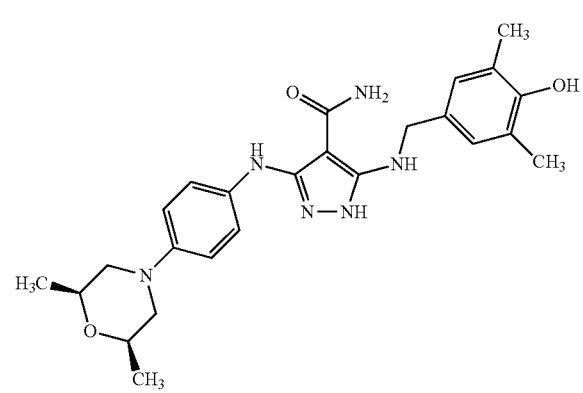

The intermediate 5-amino-3-((4-(2,6-dimethylmorpholino)phenyl)amino)-1H-pyrazole-4-carboxamide was prepared in a manner substantially similar to that described for A2 of Example 1.

5-amino-3-((4-(2,6-dimethylmorpholino)phenyl)amino)-1H-pyrazole-4-carboxamide (0.530 g) was suspended in EtOH (11 mL) and piperidine (5 drops). The reaction mixture was heated at 80° C. while stirring, and 3,5-dimethyl-4-hydroxybenzaldehyde (0.330 g) was added. After 18 h, the reaction mixture was cooled to room temperature. The separated solids was collected by suction filtration and rinsed with ethanol to give the crude imine product which was used without purification.

To a suspension of imine (100 mg) in DMF (1 mL) and MeOH (2 mL) was slowly added sodium borohydride (17 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 4 (60 mg, 99% purity) as a powder. $^1$H-NMR (500 MHz, DMSO): 11.37 (s, 1H), 8.26 (s, 1H), 8.12 (s, 1H), 7.14 (m, 2H), 6.92 (s, 2h), 6.81 (m, 2H), 6.62 (s, 3H), 4.16 (d, J=8 Hz, 2H), 3.68 (m, 2H), 3.37 (d, J=8 Hz, 2H), 2.16 (s, 6H), 1.13 (d, J=8 Hz, 6H).

Example 5

Synthesis of 3-((5-chloro-6-morpholinopyridin-3-yl) amino)-5-((4-hydroxy-3,5-dimethylbenzyl)amino)-1H-pyrazole-4-carboxamide 5

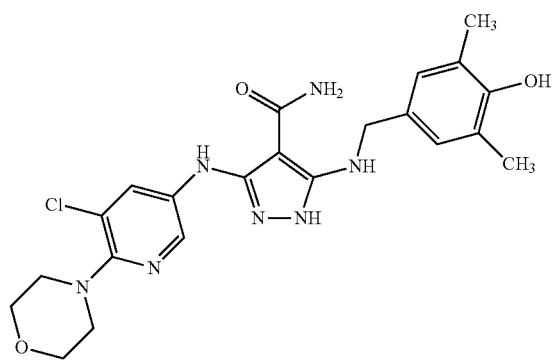

The intermediate 5-amino-3-((5-chloro-6-morpholinopyridin-3-yl)amino)-1H-pyrazole-4-carboxamide was prepared in a manner substantially similar to that described for A2 of Example 1.

5-amino-3-((5-chloro-6-morpholinopyridin-3-yl)amino)-1H-pyrazole-4-carboxamide (0.091 g) was suspended in EtOH (10 mL) and piperidine (5 drops). The reaction mixture was heated at 80° C. while stirring, and 3,5-dimethyl-4-hydroxybenzaldehyde (0.060 g) was added. After 18 h, the reaction mixture was cooled to room temperature. The separated solids was collected by suction filtration and rinsed with ethanol to give the crude imine product (122 mg) which was used without purification.

To a suspension of imine (122 mg) in DMF (3 mL) and MeOH (1 mL) was slowly added sodium borohydride (20 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 5 (99 mg, 96.5% purity) as a powder. $^1$H-NMR (500 MHz, DMSO): 11.51 (s, 1H), 8.74 (s, 1H), 8.19 (s, 1H), 8.13 (s, 1H), 8.08 (s, 1H), 6.92 (s, 2H), 6.74 (m, 3H), 4.17 (d, J=8 Hz, 2H), 3.72 (m, 4H), 3.07 (m, 4H), 2.14 (s, 6H).

Example 6

Synthesis of 3-((4-(1H-pyrrol-1-yl)phenyl)amino)-5-((4-hydroxy-3,5-dimethylbenzyl)amino)-1H-pyrazole-4-carboxamide 6

Example 7

Synthesis of 5-((4-hydroxy-3,5-dimethylbenzyl)amino)-3-((6-morpholinopyridin-3-yl)amino)-1H-pyrazole-4-carboxamide 7

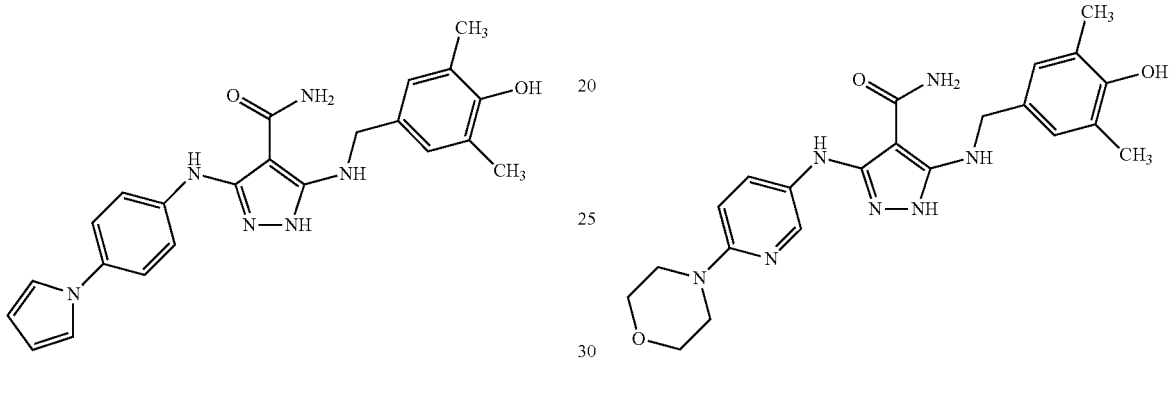

The intermediate 3-((4-(1H-pyrrol-1-yl)phenyl)amino)-5-amino-1H-pyrazole-4-carboxamide was prepared in a manner substantially similar to that described for A2 of Example 1.

3-((4-(1H-pyrrol-1-yl)phenyl)amino)-5-amino-1H-pyrazole-4-carboxami de (0.150 g) was suspended in EtOH (10 mL) and piperidine (5 drops). The reaction mixture was heated at 80° C. while stirring, and 3,5-dimethyl-4-hydroxy-benzaldehyde (0.040 g) was added. After 18 h, the reaction mixture was cooled to room temperature. The separated solids was collected by suction filtration and rinsed with ethanol to give the crude imine product which was used without purification.

To a suspension of imine (275 mg) in DMF (2 mL) and MeOH (4 mL) was slowly added sodium borohydride (50 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 6 (75 mg, 99% purity) as a powder.
$^1$H-NMR (500 MHz, DMSO): 11.50 (s, 1H), 8.65 (s, 1H), 8.14 (s, 1H), 7.35 (m, 4H), 7.19 (s, 2H), 6.93 (s, 2H), 6.68 (s, 3H), 6.20 (s, 2H), 4.18 (d, J=8 Hz, 2H), 2.15 (s, 6H).

The intermediate 5-amino-3-((6-morpholinopyridin-3-yl)amino)-1H-pyrazole-4-carboxamide was prepared in a manner substantially similar to that described for A2 of Example 1.

5-amino-3-((6-morpholinopyridin-3-yl)amino)-1H-pyrazole-4-carboxamide (0.200 g) was suspended in EtOH (10 mL) and piperidine (5 drops). The reaction mixture was heated at 80° C. while stirring, and 3,5-dimethyl-4-hydroxy-benzaldehyde (0.050 g) was added. After 18 h, the reaction mixture was cooled to room temperature. The separated solids was collected by suction filtration and rinsed with ethanol to give the crude imine product which was used without purification.

To a suspension of imine (241 mg) in DMF (2 mL) and MeOH (4 mL) was slowly added sodium borohydride (42 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 7 (75 mg, 99% purity) as a powder.
$^1$H-NMR (500 MHz, DMSO): 11.36 (s, 1H), 8.27 (s, 1H), 8.18 (s, 1H), 8.13 (s, 1H), 7.63 (s, 1H), 6.91 (s, 2H), 6.74 (d, J=8 Hz, 1H), 6.66 (s, 3H), 4.16 (d, J=8 Hz, 2H), 3.69 (m, 4H), 3.28 (m, 4H), 2.14 (s, 6H).

Example 8

Synthesis of 5-((4-hydroxy-3,5-dimethylbenzyl)amino)-3-((3-methyl-4-morpholinophenyl)amino)-1H-pyrazole-4-carboxamide 8

Example 9

Synthesis of 5-((4-hydroxy-3,5-dimethylbenzyl)amino)-3-((4-(pyridin-2-yl)phenyl)amino)-1H-pyrazole-4-carboxamide 9

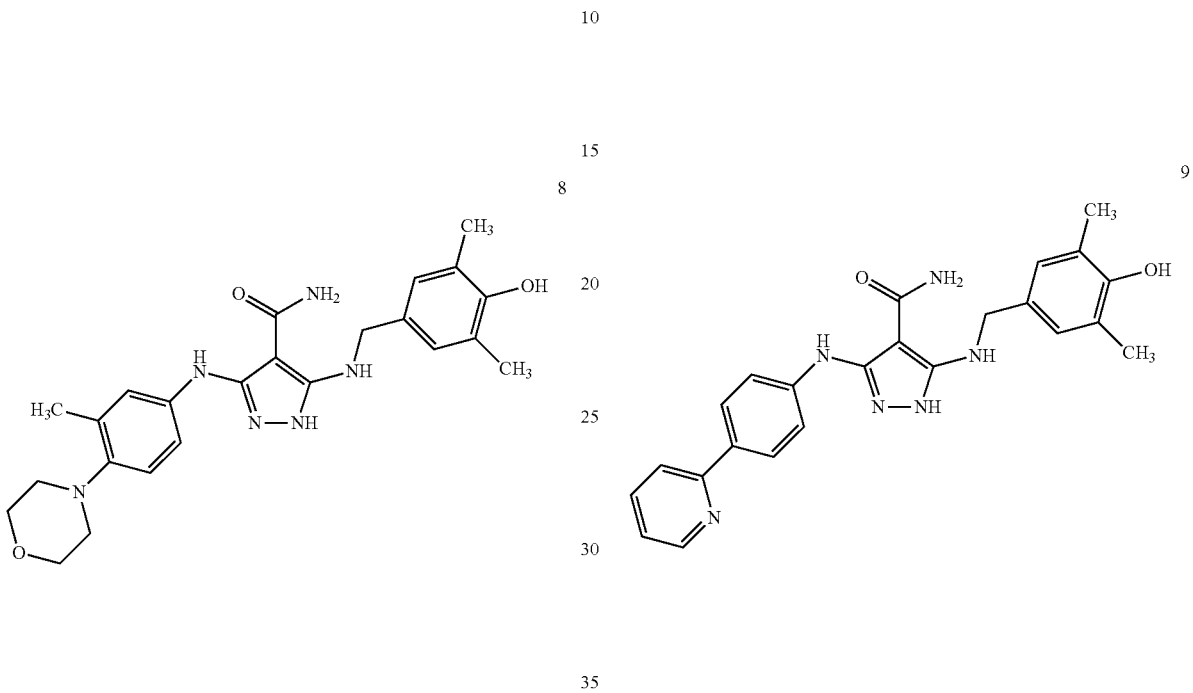

The intermediate 5-amino-3-((3-methyl-4-morpholinophenyl)amino)-1H-pyrazole-4-carboxamide was prepared in a manner substantially similar to that described for A2 of Example 1.

5-amino-3-((3-methyl-4-morpholinophenyl)amino)-1H-pyrazole-4-carboxamide (0.150 g) was suspended in EtOH (3 mL) and piperidine (5 drops). The reaction mixture was heated at 80° C. while stirring, and 3,5-dimethyl-4-hydroxybenzaldehyde (0.100 g) was added. After 18 h, the reaction mixture was cooled to room temperature. The separated solids was collected by suction filtration and rinsed with ethanol to give the crude imine product which was used without purification.

To a suspension of imine (145 mg) in DMF (2 mL) and MeOH (4 mL) was slowly added sodium borohydride (24 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 8 (100 mg, 99% purity) as a powder. $^1$H-NMR (500 MHz, DMSO): 11.43 (s, 1H), 8.34 (s, 1H), 8.13 (s, 1H), 7.07 (m, 2H), 6.91 (m, 3H), 6.64 (s, 3H), 4.16 (d, J=8 Hz, 2H), 3.70 (m, 4H), 2.74 (m, 4H), 2.19 (s, 3H), 2.15 (s, 6H).

The intermediate 5-amino-3-((4-(pyridin-2-yl)phenyl)amino)-1H-pyrazole-4-carboxamide was prepared in a manner substantially similar to that described for A2 of Example 1.

5-amino-3-((4-(pyridin-2-yl)phenyl)amino)-1H-pyrazole-4-carboxamide (0.200 g) was suspended in EtOH (4 mL) and piperidine (5 drops). The reaction mixture was heated at 80° C. while stirring, and 3,5-dimethyl-4-hydroxybenzaldehyde (0.143 g) was added. After 18 h, the reaction mixture was cooled to room temperature. The separated solids was collected by suction filtration and rinsed with ethanol to give the crude imine product which was used without purification.

To a suspension of imine (350 mg) in DMF (3 mL) and MeOH (6 mL) was slowly added sodium borohydride (62 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 9 (110 mg, 97.7% purity) as a powder. $^1$H-NMR (500 MHz, DMSO): 11.58 (s, 1H), 8.85 (s, 1H), 8.57 (m, 1H), 8.15 (s, 1H), 7.95 (d, J=8 Hz, 2H), 7.79 (m, 4H), 7.33 (m, 2H), 7.21, (m, 1H), 6.94 (s, 2H), 6.70 (s, 3H), 4.19 (m, 2H), 2.15 (s, 6H).

Example 10

Synthesis of 5-((4-hydroxy-3,5-dimethylbenzyl)amino)-3-((4-(4-methylpiperazin-1-yl)phenyl)amino)-1H-pyrazole-4-carboxamide 10

Example 11

Synthesis of 5-((4-hydroxy-3,5-dimethylbenzyl)amino)-3-((5-morpholinopyridin-2-yl)amino)-1H-pyrazole-4-carboxamide 11

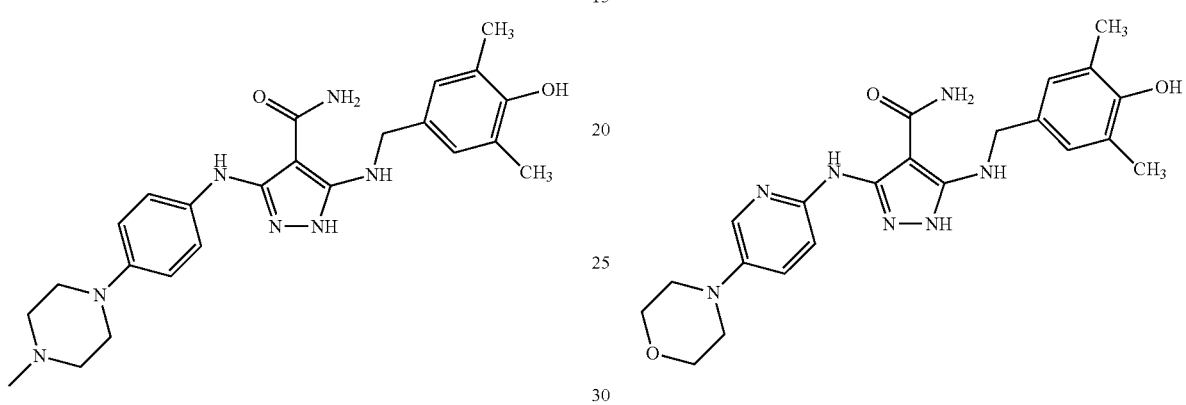

The intermediate 5-amino-3-((4-(4-methylpiperazin-1-yl)phenyl)amino)-1H-pyrazole-4-carboxamide was prepared in a manner substantially similar to that described for A2 of Example 1.

5-amino-3-((4-(4-methylpiperazin-1-yl)phenyl)amino)-1H-pyrazole-4-carboxamide (0.250 g) was suspended in EtOH (5 mL) and piperidine (5 drops). The reaction mixture was heated at 80° C. while stirring, and 3,5-dimethyl-4-hydroxybenzaldehyde (0.167 g) was added. After 18 h, the reaction mixture was cooled to room temperature. The separated solids was collected by suction filtration and rinsed with ethanol to give the crude imine product which was used without purification.

To a suspension of imine (250 mg) in DMF (2 mL) and MeOH (4 mL) was slowly added sodium borohydride (42 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 10 (30 mg, 94% purity) as a powder. $^1$H-NMR (500 MHz, DMSO): 11.38 (s, 1H), 8.29 (s, 1H), 8.13 (s, 1H), 7.15 (m, 2H), 6.92 (s, 2H), 6.84 (m, 2H), 6.63 (s, 3H), 4.16 (s, 2H), 3.11 (s, 2H), 2.99 (s, 2H), 2.89 (s, 2H), 2.58 (s, 3H), 2.14 (s, 6H), 1.57 (m, 2H), 1.23 (s, 1H).

The intermediate 5-amino-3-((5-morpholinopyridin-2-yl)amino)-1H-pyrazole-4-carboxamide was prepared in a manner substantially similar to that described for A2 of Example 1.

5-amino-3-((5-morpholinopyridin-2-yl)amino)-1H-pyrazole-4-carboxamide (0.153 g) was suspended in EtOH (3 mL) and acetic acid (1 mL). The reaction mixture was heated at 80° C. while stirring, and 3,5-dimethyl-4-hydroxybenzaldehyde (0.105 g) was added. After 18 h, the reaction mixture was cooled to room temperature. The separated solids was collected by suction filtration and rinsed with ethanol to give the crude imine product which was used without purification.

To a suspension of imine (80 mg) in DMF (4 mL) and MeOH (2 mL) was slowly added sodium borohydride (140 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 11 (77 mg, 98.5% purity) as a powder. $^1$H-NMR (500 MHz, DMSO): 11.93 (s, 0.4H), 11.43 (s, 0.6H), 9.65 (s, 0.4H), 9.15 (s, 0.6H), 8.13 (s, 0.6H), 8.00 (s, 0.4H), 7.95 (s, 1H), 7.59 (d, 0.6H), 7.42 (m, 0.4H), 7.32 (m, 0.6H), 6.94 (m, 2.3H), 6.77 (s, 0.8H), 6.70 (s, 1.2H), 6.56 (m, 0.6H), 5.70 (m, 0.4H), 4.17 (m, 2H), 3.73 (s, 4H), 3.01 (m, 4H), 2.14 (s, 6H).

Example 12

Synthesis of 5-((4-hydroxy-3,5-dimethylbenzyl) amino)-3-((5-methyl-6-morpholinopyridin-3-yl) amino)-1H-pyrazole-4-carboxamide 12

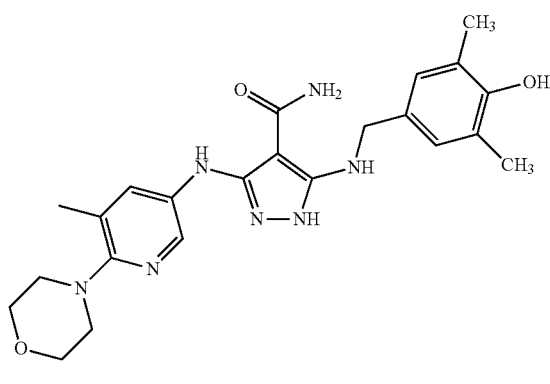

The intermediate 5-amino-3-((5-methyl-6-morpholinopyridin-3-yl)amino)-1H-pyrazole-4-carboxamide was prepared in a manner substantially similar to that described for A2 of Example 1.

5-amino-3-((5-methyl-6-morpholinopyridin-3-yl)amino)-1H-pyrazole-4-carboxamide (0.340 g) was suspended in EtOH (18 mL) and acetic acid (1 mL). The reaction mixture was heated at 80° C. while stirring, and 3,5-dimethyl-4-hydroxybenzaldehyde (0.240 g) was added. After 18 h, the reaction mixture was cooled to room temperature. The separated solids was collected by suction filtration and rinsed with ethanol to give the crude imine product which was used without purification.

To a suspension of imine (73 mg) in DMF (2 mL) and MeOH (1 mL) was slowly added sodium borohydride (12 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 12 (60 mg, 97.6% purity) as a powder. $^1$H-NMR (500 MHz, DMSO): 11.44 (s, 1H), 8.47 (s, 1H), 8.10 (s, 2H), 7.58 (s, 1H), 6.92 (s, 2H), 6.68 (s, 3H), 4.16 (d, J=6 Hz, 2H), 3.71 (t, J=5 Hz, 4H), 2.91 (t, J=5 Hz, 4H), 2.20 (s, 3H), 2.14 (s, 6H).

Example 13

Synthesis of 5-((4-hydroxy-3,5-dimethylbenzyl) amino)-3-((6-(4-isopropylpiperazin-1-yl)-5-methylpyridin-3-yl)amino)-1H-pyrazole-4-carboxamide 13

The intermediate 5-amino-3-((6-(4-isopropylpiperazin-1-yl)-5-methylpyridin-3-yl)amino)-1H-pyrazole-4-carboxamide was prepared in a manner substantially similar to that described for A2 of Example 1.

5-amino-3-((6-(4-isopropylpiperazin-1-yl)-5-methylpyridin-3-yl)amino)-1H-pyrazole-4-carboxamide (0.210 g) was suspended in EtOH (12 mL) and acetic acid (0.5 mL). The reaction mixture was heated at 80° C. while stirring, and 3,5-dimethyl-4-hydroxybenzaldehyde (0.130 g) was added. After 18 h, the reaction mixture was cooled to room temperature. The separated solids was collected by suction filtration and rinsed with ethanol to give the crude imine product which was used without purification.

To a suspension of imine (50 mg) in DMF (3 mL) and MeOH (1.5 mL) was slowly added sodium borohydride (10 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 13 (41 mg, 99.3% purity) as a powder. $^1$H-NMR (500 MHz, DMSO): 11.43 (s, 1H), 8.14 (s, 1H), 8.07 (s, 1H), 7.55 (s, 1H), 6.92 (s, 2H), 6.68 (s, 3H), 4.16 (d, J=6, 2H), 2.90 (m, 4H), 2.66 (m, 1H) 2.56 (m, 4H), 2.18 (s, 3H), 2.14 (s, 6H), 1.00 (d, J=7, 6H).

Example 14

Synthesis of 5-((4-hydroxy-3,5-dimethylbenzyl)amino)-3-((5-methyl-6-(4-methylpiperazin-1-yl)pyridin-3-yl)amino)-1H-pyrazole-4-carboxamide 14

Example 15

Synthesis of 3-((3-chloro-4-(2,6-dimethylmorpholino)phenyl)amino)-5-((4-hydroxy-3,5-dimethylbenzyl)amino)-1H-pyrazole-4-carboxamide 15

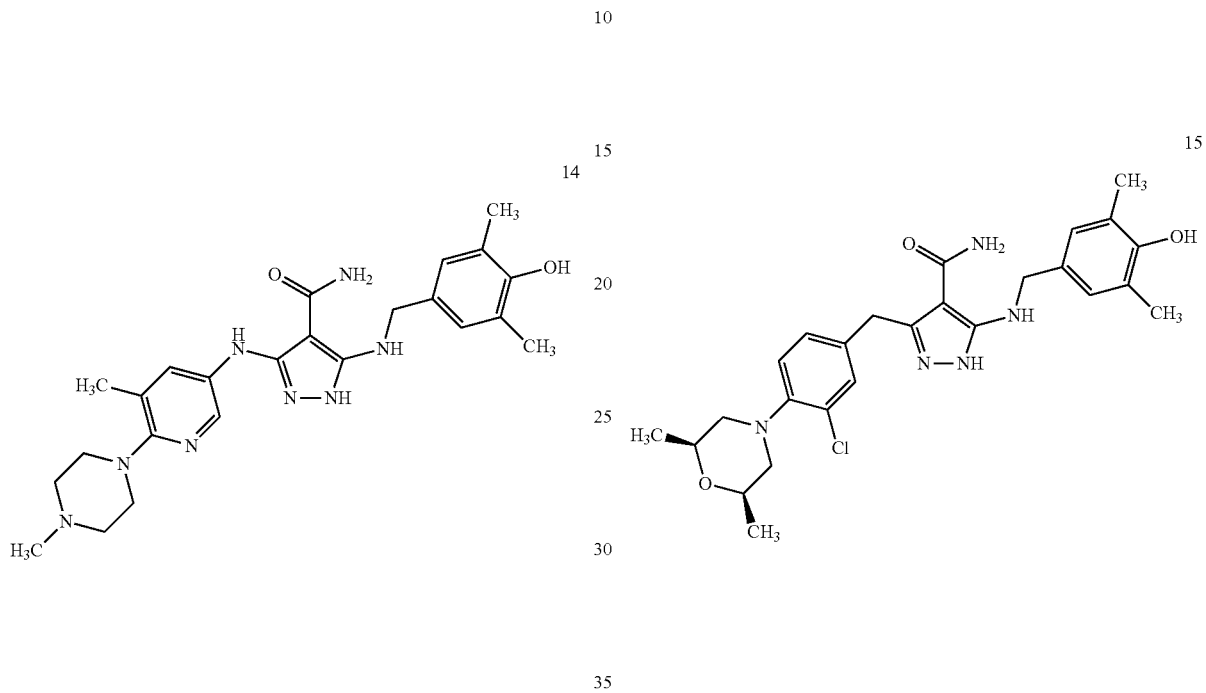

The intermediate 5-amino-3-((5-methyl-6-(4-methylpiperazin-1-yl)pyridin-3-yl)amino)-1H-pyrazole-4-carboxamide was prepared in a manner substantially similar to that described for A2 of Example 1.

5-amino-3-((5-methyl-6-(4-methylpiperazin-1-yl)pyridin-3-yl)amino)-1H-pyrazole-4-carboxamide (0.21 g) was suspended in EtOH (8 mL) and acetic acid (1 mL). The reaction mixture was heated at 80° C. while stirring, and 3,5-dimethyl-4-hydroxybenzaldehyde (0.136 g) was added. After 16 h, the reaction mixture was cooled to room temperature. The separated solids was collected by suction filtration and rinsed with ethanol to give the crude imine product which was used without purification.

To a suspension of imine (153 mg) in DMF (3 mL) and MeOH (1 mL) was slowly added sodium borohydride (25 mg) at room temperature. After the reaction mixture was stirred at room temperature for 1 hr, water was added and the resulting suspension was stirred for 30 min. The solid was collected by suction filtration, washed with water, and dried to yield compound 14 (41 mg, 99.3% purity) as a white powder. $^1$H-NMR (500 MHz, DMSO): 11.43 (s, 1H), 8.51 and 8.44 (s, s, 1H), 8.12 and 8.08 (s, s, 2H), 7.59 and 7.56 (s, s, 1H), 6.92 (s, 2H), 6.69 (d, J=5 Hz, 3H), 4.16 (d, J=6 Hz, 2H), 3.17 (m, 1H), 3.04 (m, 1H), 2.91 (m, 4H), 2.60 (s, 1H), 2.44 (s, 2H), 2.22 (s, 2H), 2.18 (d, J=3 Hz, 3H), 2.14 (s, 6H).

The intermediate 5-amino-3-((3-chloro-4-(2,6-dimethylmorpholino)phenyl)amino)-1H-pyrazole-4-carboxamide was prepared in a manner substantially similar to that described for A2 of Example 1.

5-amino-3-((3-chloro-4-(2,6-dimethylmorpholino)phenyl)amino)-1H-pyrazole-4-carboxamide (0.235 g) was suspended in EtOH (4.7 mL) and piperidine (5 drops). The reaction mixture was heated at 80° C. while stirring, and 3,5-dimethyl-4-hydroxybenzaldehyde (0.145 g) was added. After 18 h, the reaction mixture was cooled to room temperature. The separated solids was collected by suction filtration and rinsed with ethanol to give the crude imine product which was used without purification.

To a suspension of imine (55 mg) in DMF (1 mL) and MeOH (1 mL) was slowly added sodium borohydride (8 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 15 (55 mg, 97.5% purity) as a powder. $^1$H-NMR (500 MHz, DMSO): 11.50 (s, 1H), 8.62 (s, 1H), 8.15 (s, 1H), 7.56 (s, 1H), 7.07 (d, 1H), 7.0 (d, 1H), 6.92 (s, 2H), 6.71 (m, 1H), 6.68 (s, 2H), 4.16 (m, 2H), 3.71 (m, 2H), 3.01 (d, 2H), 2.30 (t, 2H), 2.14 (s, 6H), 1.10 (d, 6H).

Example 16

Synthesis of 5-((4-hydroxy-3,5-dimethylbenzyl)amino)-3-((4-(pyridin-3-yl)phenyl)amino)-1H-pyrazole-4-carboxamide 16

Example 17

Synthesis of 3-((3-chloro-4-(4-isopropylpiperazin-1-yl)phenyl)amino)-5-((4-hydroxy-3,5-dimethylbenzyl)amino)-1H-pyrazole-4-carboxamide 17

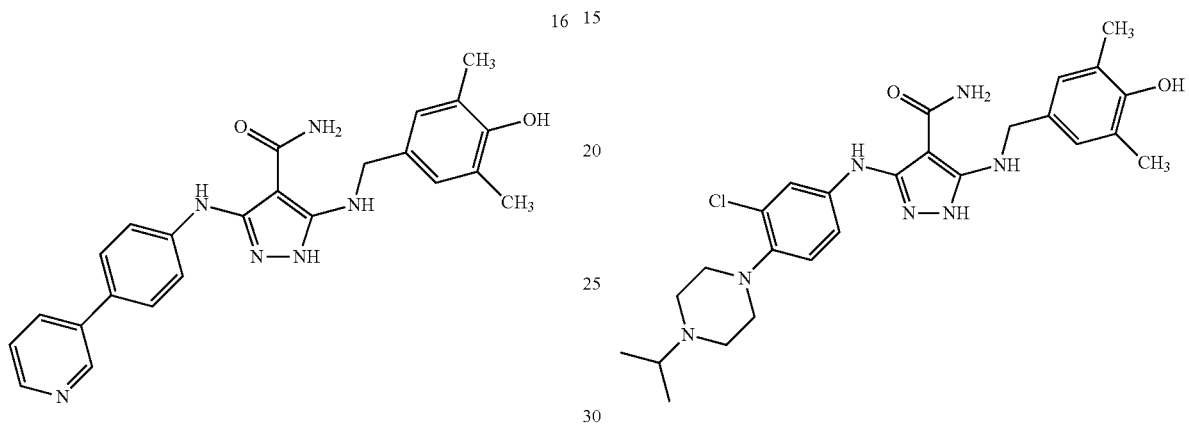

The intermediate 5-amino-3-((4-(pyridin-3-yl)phenyl)amino)-1H-pyrazole-4-carboxamide was prepared in a manner substantially similar to that described for A2 of Example 1.

5-amino-3-((4-(pyridin-3-yl)phenyl)amino)-1H-pyrazole-4-carboxamide (0.330 g) was suspended in EtOH (20 mL) and piperidine (5 drops). The reaction mixture was heated at 80° C. while stirring, and 3,5-dimethyl-4-hydroxybenzaldehyde (0.250 g) was added. After 18 h, the reaction mixture was cooled to room temperature. The separated solids was collected by suction filtration and rinsed with ethanol to give the crude imine product which was used without purification.

To a suspension of imine (64 mg) in DMF (6 mL) and MeOH (3 mL) was slowly added sodium borohydride (10 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 16 (57 mg, 98.4% purity) as a powder.
$^1$H-NMR (500 MHz, DMSO): 11.57 (s, 1H), 8.83 (m, 1H), 8.79 (s, 1H), 8.46 (m, 1H), 8.16 (s, 1H), 7.99 (m, 1H), 7.57 (d, J=9 Hz, 2H), 7.41 (m, 1H), 7.35 (d, J=9 Hz, 2H), 6.93 (2H), 6.71 (m, 3H), 4.19 (d, J=6 Hz, 2H), 2.15 (s, 6H).

The intermediate 5-amino-3-((3-chloro-4-(4-isopropylpiperazin-1-yl)phenyl)amino)-1H-pyrazole-4-carboxamide was prepared in a manner substantially similar to that described for A2 of Example 1.

5-amino-3-((3-chloro-4-(4-isopropylpiperazin-1-yl)phenyl)amino)-1H-pyrazole-4-carboxamide (0.460 g) was suspended in EtOH (8 mL) and piperidine (5 drops). The reaction mixture was heated at 80° C. while stirring, and 3,5-dimethyl-4-hydroxybenzaldehyde (0.270 g) was added. After 18 h, the reaction mixture was cooled to room temperature. The separated solids was collected by suction filtration and rinsed with ethanol to give the crude imine product which was used without purification.

To a suspension of imine (80 mg) in DMF (2 mL) and MeOH (1 mL) was slowly added sodium borohydride (12 mg) at room temperature. After the reaction mixture was stirred at room temperature for 1 hr, water was added and the resulting solid was collected by suction filtration. The recovered precipitate was dissolved in DMSO, filtered through a cotton plug, which was further rinsed with EtOH. The DMSO and EtOH filtrates were combined, and water was added until a precipitate formed. The resulting suspension was chilled in a refrigerator for 3 hours. The resulting precipitate was filtered, washed with water, and dried to yield compound 17 (60 mg, 96.1% purity) as a powder.
$^1$H-NMR (500 MHz, DMSO): 11.95 (s, 1H), 8.57 (s, 1H), 8.14 (s, 1H), 7.54 (s, 1H), 7.01 (m, 2H), 6.92 (s, 2H), 6.67 (m, 3H), 4.16 (d, J=6 Hz, 2H), 2.86 (s, 4H), 2.68 (m, 1H), 2.57 (s, 4H), 2.14 (s, 6H), 1.00 (d, J=7 Hz, 6H).

Example 18

Synthesis of 3-([1,1'-biphenyl]-4-ylamino)-5-((4-hydroxy-3,5-dimethylbenzyl)amino)-1H-pyrazole-4-carboxamide 18

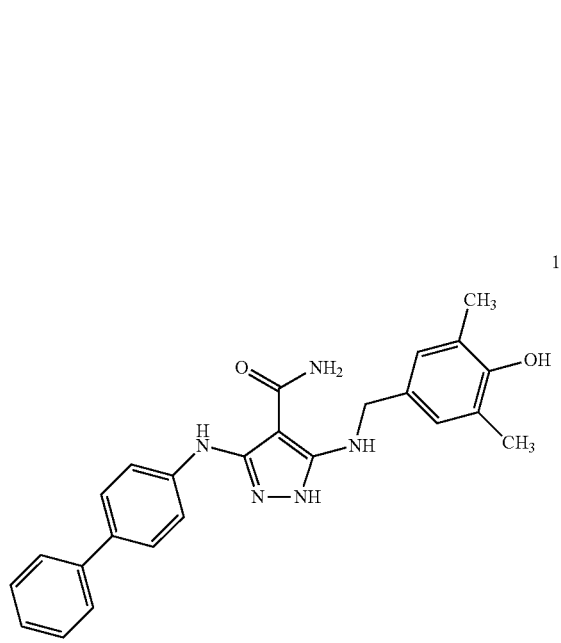

The intermediate 5-amino-3-((3-chloro-4-(4-isopropylpiperazin-1-yl)phenyl)amino)-1H-pyrazole-4-carboxamide was prepared in a manner substantially similar to that described for A2 of Example 1.

3-([1,1'-biphenyl]-4-ylamino)-5-amino-1H-pyrazole-4-carboxamide (0.086 g) was suspended in EtOH (10 mL) and acetic acid (0.5 mL). The reaction mixture was heated at 80° C. while stirring, and 3,5-dimethyl-4-hydroxybenzaldehyde (0.270 g) was added. After 20 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filtration, washed with water, and dried to yield compound 18 (60 mg) as a powder. $^{1}$H-NMR (500 MHz, DMSO): 11.54 (s, 1H), 8.71 (s, 1H), 8.15 (s, 1H), 7.59 (d, 2H), 7.50 (s, 2H), 7.40 (t, 2H), 7.31 (d, 2H), 7.24 (t, 1H), 6.93 (s, 2H), 6.69 (s, 3H), 4.19 (d, 2H), 2.15 (s, 6H).

Example 19

3-((4-(1H-imidazol-1-yl)phenyl)amino)-5-((4-hydroxy-3,5-dimethylbenzyl)amino)-1H-pyrazole-4-carboxamide 19

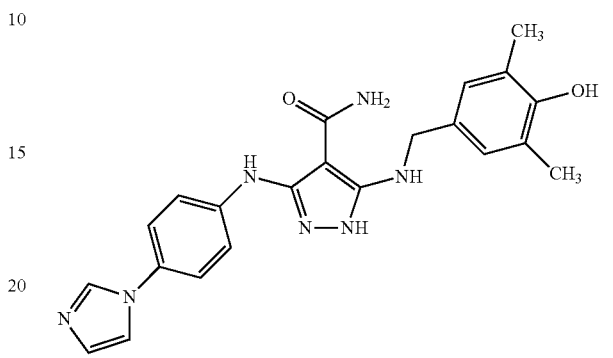

The intermediate 3-((4-(1H-imidazol-1-yl)phenyl)amino)-5-amino-1H-pyrazole-4-carboxamide was prepared in a manner substantially similar to that described for A2 of Example 1.

3-((4-(1H-imidazol-1-yl)phenyl)amino)-5-amino-1H-pyrazole-4-carboxamide (0.246 g) was suspended in EtOH (10 mL) and piperidine (5 drops). The reaction mixture was heated at 80° C. while stirring, and 1.4 equivalents of 3,5-dimethyl-4-hydroxybenzaldehyde was added. After 20 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filtration, washed with water, and dried to yield compound 19 (25 mg) as a powder. $^{1}$H-NMR (500 MHz, DMSO): 2.15 (s, 6H), 4.19 (d, 2H), 6.70 (s, 3H), 6.93 (s, 2H), 7.05 (s, 1H), 7.35 (s, 2H), 7.42 (d, 2H), 7.58 (s, 1H), 8.06 (s, 1H), 8.15 (s, 1H), 8.76 (s, 1H), 11.54 (s, 1H)

Example 20

Synthesis of 5-((4-hydroxy-3,5-dimethylbenzyl)amino)-3-((4-methoxyphenyl)amino)-1H-pyrazole-4-carboxamide 20

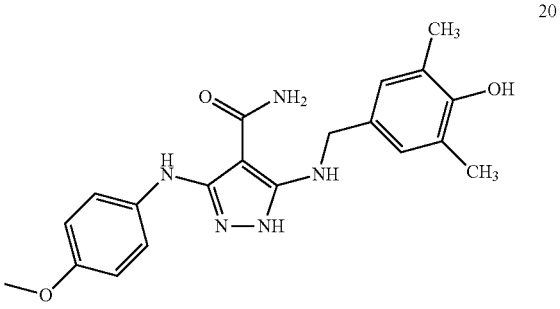 [SMILES: COc1ccc(Nc2n[nH]c(NCc3cc(C)c(O)c(C)c3)c2C(N)=O)cc1]

The intermediate 5-amino-3-((4-methoxyphenyl)amino)-1H-pyrazole-4-carboxamide was prepared in a manner substantially similar to that described for A2 of Example 1.

5-amino-3-((4-methoxyphenyl)amino)-1H-pyrazole-4-carboxamide (160 mg) was suspended in EtOH (10 mL) and piperidine (5 drops). The reaction mixture was heated at 80° C. while stirring, and 1.4 equivalents of 3,5-dimethyl-4-hydroxybenzaldehyde was added. After 24 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filtration, washed with water, and dried to yield compound 20 (20 mg) as a powder. $^1$H-NMR (500 MHz, DMSO): 2.17 (s, 6H), 3.68 (s, 3H), 4.16 (d, 2H), 6.64 (m, 3H), 6.77 (d, 2H), 6.92 (s, 2H), 7.18 (d, 2H), 8.14 (s, 1H), 8.31 (s, 1H), 11.38 (s, 1H).

Example 21

Synthesis of 3-((4-(tert-butyl)phenyl)amino)-5-((4-hydroxy-3,5-dimethylbenzyl)amino)-1H-pyrazole-4-carboxamide 21

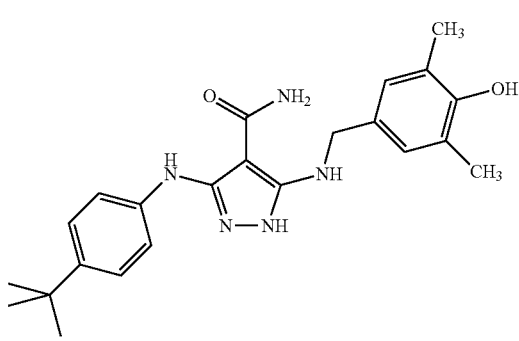

The intermediate 5-amino-3-((4-(tert-butyl)phenyl)amino)-1H-pyrazole-4-carboxamide was prepared in a manner substantially similar to that described for A2 of Example 1.

5-amino-3-((4-(tert-butyl)phenyl)amino)-1H-pyrazole-4-carboxamide (98 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 20 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filtration, washed with water, and dried to yield compound 21 (90 mg) as a powder. $^1$H-NMR (500 MHz, DMSO): 1.23 (s, 9H), 2.14 (s, 6H), 4.17 (d, 2H), 6.64 (m, 3H), 6.92 (s, 2H), 7.10 (m, 2H), 7.20 (d, 2H), 8.13 (s, 1H), 8.40 (s, 1H), 11.53 (s, 1H).

Example 22

Synthesis of 3-((1H-indazol-5-yl)amino)-5-((4-hydroxy-3,5-dimethylbenzyl)amino)-1H-pyrazole-4-carboxamide 22

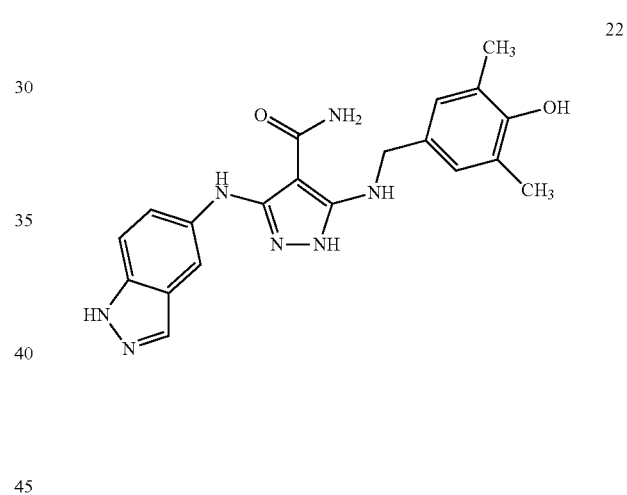

The intermediate 3-((1H-indazol-5-yl)amino)-5-amino-1H-pyrazole-4-carboxamide was prepared in a manner substantially similar to that described for A2 of Example 1.

3-((1H-indazol-5-yl)amino)-5-amino-1H-pyrazole-4-carboxamide (99 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 20 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filtration, washed with water, and dried to yield compound 22 (112 mg) as a powder. $^1$H-NMR (500 MHz, DMSO): 2.15 (s, 6H), 4.18 (d, 2H), 6.66 (m, 3H), 6.93 (s, 2H), 7.12 (d, 1H), 7.37 (d, 2H), 7.66 (m, 1H), 7.86 (s, 1H), 8.14 (m, 1h0, 8.47 (s, 1H), 11.43 (s, 1H), 12.75 (s, 1H).

Example 23

5-((4-hydroxy-3,5-dimethylbenzyl)amino)-3-((4-(4-methyl-[1,4'-bipiperidin]-1'-yl)phenyl)amino)-1H-pyrazole-4-carboxamide 23

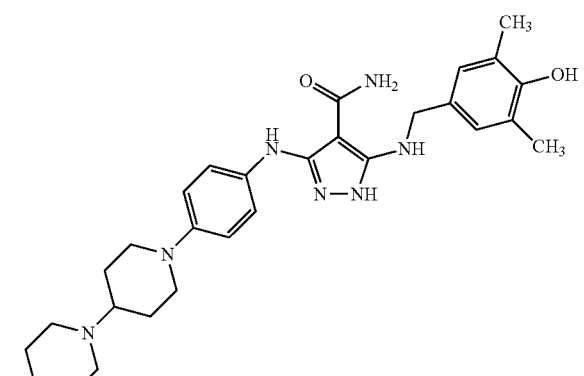

The intermediate 5-amino-3-((4-(4-methyl-[1,4'-bipiperidin]-1'-yl)phenyl)amino)-1H-pyrazole-4-carboxamide was prepared in a manner substantially similar to that described for A2 of Example 1.

5-amino-3-((4-(4-methyl-[1,4'-bipiperidin]-1'-yl)phenyl)amino)-1H-pyrazole-4-carboxamide (99 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 20 h, the reaction mixture was cooled to room temperature. The separated solids was collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filteration, washed with water, and dried to yield compound 23 (112 mg) as a powder. $^1$H-NMR (500 MHz, DMSO): 2.15 (s, 6H), 4.18 (d, 2H), 6.66 (m, 3H), 6.93 (s, 2H), 7.12 (d, 1H), 7.37 (d, 2H), 7.66 (m, 1H), 7.86 (s, 1H), 8.14 (m, 1h0, 8.47 (s, 1H), 11.43 (s, 1H), 12.75 (s, 1H).

Example 24

Synthesis of 5-((4-hydroxy-3,5-dimethylbenzyl)amino)-3-((4-(4-(pyrrolidine-1-carbonyl)piperazin-1-yl)phenyl)amino)-1H-pyrazole-4-carboxamide 24

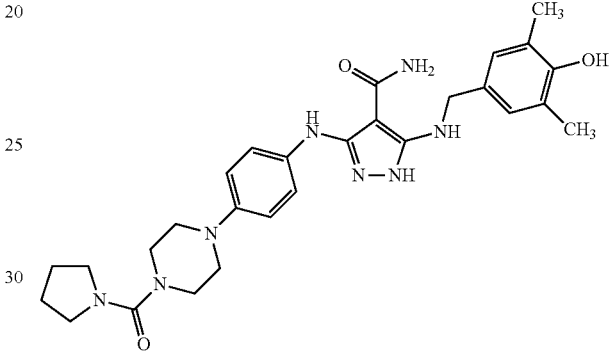

The intermediate 5-amino-3-((4-(4-(pyrrolidine-1-carbonyl)piperazin-1-yl)phenyl)amino)-1H-pyrazole-4-carboxamide was prepared in a manner substantially similar to that described for A2 of Example 1.

5-amino-3-((4-(4-(pyrrolidine-1-carbonyl)piperazin-1-yl)phenyl)amino)-1H-pyrazole-4-carboxamide (60 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 2 days, the reaction mixture was cooled to room temperature. The separated solids was collected by suction filtration and rinsed with ethanol to give the crude imine product which was used without purification. The crude imine was combined with DMF (1 mL) and MeOH (2 mL) and treated with 2 equivalents of sodium borohydride at room temperature. After 6 hours, water was added, and the separated precipitate was collected by suction filteration, washed with water, and dried to yield compound 24 (40 mg) as a powder. $^1$H-NMR (500 MHz, DMSO): 11.38 (s, 1H), 8.28 (s, 1H), 8.14 (s, 1H), 7.14 (d, 2H), 6.92 (s, 2H), 6.82 (d, 2H), 6.64 (s, 3H), 4.16 (d, 2H), 3.28 (m, 8H), 2.97 (m, 4H), 2.14 (s, 6H), 1.75 (m, 4H).

Example 25

3-((4-(4-fluoropiperidin-1-yl)phenyl)amino)-5-((4-hydroxy-3,5-dimethylbenzyl)amino)-1H-pyrazole-4-carboxamide 25

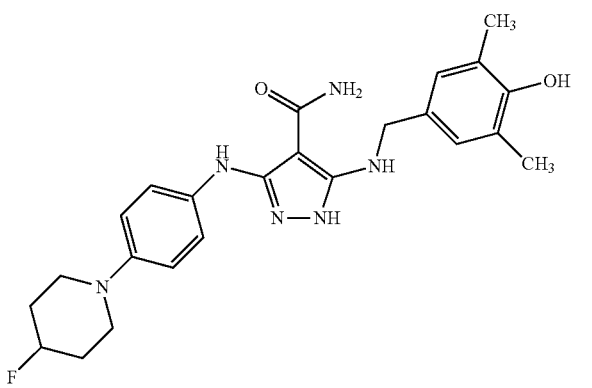

The intermediate 5-amino-3-((4-(4-fluoropiperidin-1-yl)phenyl)amino)-1H-pyrazole-4-carboxamide was prepared in a manner substantially similar to that described for A2 of Example 1.

5-amino-3-((4-(4-fluoropiperidin-1-yl)phenyl)amino)-1H-pyrazole-4-carboxamide (320 mg) was suspended in EtOH (15 mL) and acetic acid (1 mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids was collected by suction filtration and rinsed with ethanol to give the crude imine product which was used without purification. The crude imine was combined with DMF (2 mL) and MeOH (0.5 mL) and treated with 2 equivalents of sodium borohydride at room temperature. After 1 hour, water was added, and the separated precipitate was collected by suction filtration, washed with water, and dried to yield compound 25 (92 mg) as a powder. $^1$H-NMR (500 MHz, DMSO): 11.37 (s, 1H), 8.27 (s, 1H), 8.14 (s, 1H), 7.13 (d, 2H), 6.92 (s, 2H), 6.83 (d, 2H), 6.63 (m, 3H), 4.793 (m, 1H), 4.16 (d, 2H), 3.17 (m, 2H), 2.94 (m, 2H), 2.14 (s, 6H), 1.95 (m, 2H), 7.80 (m, 2H).

Example 26

3-((6-((2R,6S)-2,6-dimethyltetrahydro-2H-pyran-4-yl)pyridin-3-yl)amino)-5-((4-hydroxy-3,5-dimethylbenzyl)amino)-1H-pyrazole-4-carboxamide 26

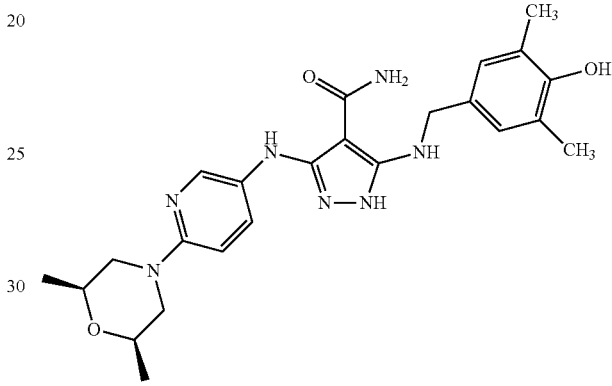

The intermediate 5-amino-3-((6-((2R,6S)-2,6-dimethyltetrahydro-2H-pyran-4-yl)pyridin-3-yl)amino)-1H-pyrazole-4-carboxamide was prepared in a manner substantially similar to that described for A2 of Example 1.

5-amino-3-((6-((2R,6S)-2,6-dimethyltetrahydro-2H-pyran-4-yl)pyridin-3-yl)amino)-1H-pyrazole-4-carboxamide (1.020 g) was suspended in EtOH (3 mL) and acetic acid (0.5 mL). The reaction mixture was heated at 80° C. while stirring, and 1.5 equivalents of 3,5-dimethyl-4-hydroxybenzaldehyde was added. After 12 hours, the reaction mixture was cooled to room temperature. The separated solids were collected by suction filtration and rinsed with ethanol to give the crude imine product which was used without purification (0.955 g). The crude imine (0.056 g) was combined with DMF (2 mL) and MeOH (1 mL) and treated with 2 equivalents of sodium borohydride at room temperature. After 30 minutes, water was added, and the separated precipitate was collected by suction filtration, washed with water, and dried to yield compound 26 (36 mg) as a powder. $^1$H-NMR (500 MHz, DMSO): 11.35 (s, 1H), 8.27 (s, 1H), 8.15 (d, 2H), 7.64 (d, 1H), 6.91 (s, 2H), 6.74 (d, 1H), 6.68 (m, 3H), 4.16 (d, 2H), 3.92 (d, 2H), 3.62 (m, 2H), 2.25 (t, 3H), 2.14 (s, 6H), 1.14 (d, 6H).

Example 27

5-((4-hydroxy-3,5-dimethylbenzyl)amino)-3-((4-(piperidin-1-yl)phenyl)amino)-1H-pyrazole-4-carboxamide 27

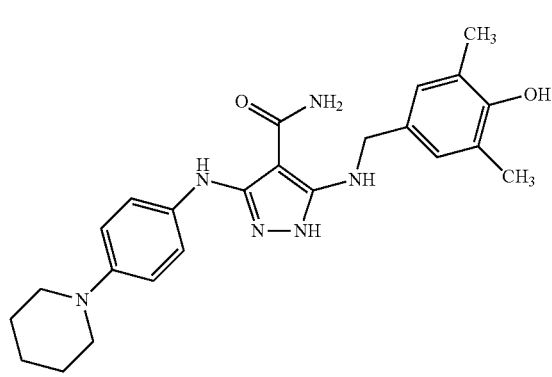

The intermediate 5-amino-3-((4-(piperidin-1-yl)phenyl)amino)-1H-pyrazole-4-carboxamide was prepared in a manner substantially similar to that described for A2 of Example 1.

5-amino-3-((4-(piperidin-1-yl)phenyl)amino)-1H-pyrazole-4-carboxamide (89 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 20 hours, the reaction mixture was cooled to room temperature. The separated solids were collected by suction filtration and rinsed with ethanol to give the crude imine product which was used without purification. The crude imine was combined with DMF (1 mL) and MeOH (1 mL) and treated with 2 equivalents of sodium borohydride at room temperature. After 5 hours, water was added, and the separated precipitate was collected by suction filteration, washed with water, and dried to yield compound 27 (36 mg) as a powder. $^1$H-NMR (500 MHz, DMSO): 11.37 (s, 1H), 8.23 (s, 1H), 8.14 (s, 1H), 7.11 (d, 2H), 6.92 (s, 2H), 6.79 (d, 2H), 6.63 (s, 2H), 4.16 (d, 2H), 2.95 (, 5H), 2.14 (s, 6H), 1.60 (m, 4H), 1.48 (m, 2H).

Example 28

Synthesis of 3-((3-chloro-4-((2S,6R)-2,6-dimethylmorpholino)phenyl)amino)-5-((4-hydroxy-3,5-dimethylbenzyl)amino)-1H-pyrazole-4-carboxamide 28

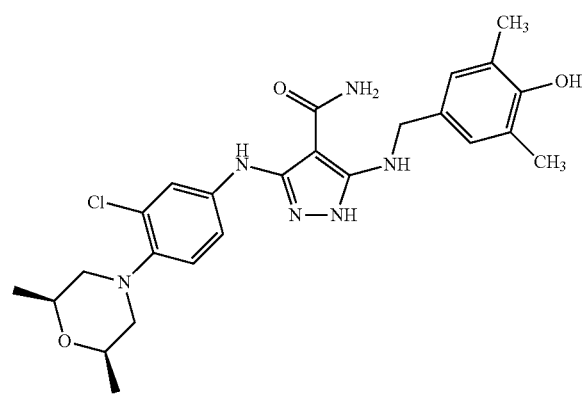

The intermediate 5-amino-3-((3-chloro-4-((2S,6R)-2,6-dimethylmorpholino)phenyl)amino)-1H-pyrazole-4-carboxamide was prepared in a manner substantially similar to that described for A2 of Example 1.

5-amino-3-((3-chloro-4-((2S,6R)-2,6-dimethylmorpholino)phenyl)amino)-1H-pyrazole-4-carboxamide (235 mg) was suspended in EtOH (3 mL) and acetic acid (0.5 mL). The reaction mixture was heated at 80° C. while stirring, and 1.5 equivalents of 3,5-dimethyl-4-hydroxybenzaldehyde was added. After 5 hours, the reaction mixture was cooled to room temperature. The separated solids were collected by suction filtration and rinsed with ethanol to give the crude imine product which was used without purification. The crude imine (55 mg) was combined with DMF (1 mL) and MeOH (0.5 mL) and treated with 2 equivalents of sodium borohydride at room temperature. After 1 hour, water was added, and the separated precipitate was collected by suction filteration, washed with water, and dried to yield compound 28 (55 mg) as a powder. $^1$H-NMR (500 MHz, DMSO): 11.50 (s, 1H), 8.62 (s, 1H), 8.15 (s, 1H), 7.56 (s, 1H), 7.07 (d, 1H), 7.0 (d, 1H), 6.92 (s, 2H), 6.71 (m, 1H), 6.68 (s, 2H), 4.16 (m, 2H), 3.71 (m, 2H), 3.01 (d, 2H), 2.30 (t, 2H), 2.14 (s, 6H), 1.10 (d, 6H).

Example 29

Synthesis of 5-((4-hydroxy-3,5-dimethylbenzyl)amino)-3-((3-methyl-4-(4-methylpiperazin-1-yl)phenyl)amino)-1H-pyrazole-4-carboxamide 29

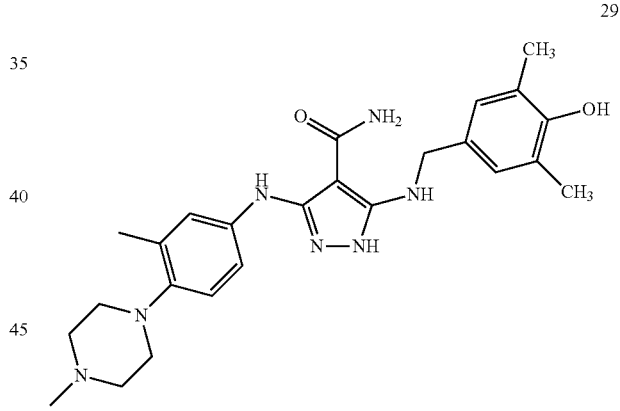

The intermediate 5-amino-3-((3-methyl-4-(4-methylpiperazin-1-yl)phenyl)amino)-1H-pyrazole-4-carboxamide was prepared in a manner substantially similar to that described for A2 of Example 1.

5-amino-3-((3-methyl-4-(4-methylpiperazin-1-yl)phenyl)amino)-1H-pyrazole-4-carboxamide (420 mg) was suspended in EtOH (10 mL) and acetic acid (0.5 mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (0.650 g) which was used without purification. The crude imine (87 mg) was combined with DMF (1 mL) and MeOH (0.5 mL) and treated with 2 equivalents of sodium borohydride at room temperature. After 1 hour, water was added, and the separated precipitate was collected by suction filteration, washed with water, and dried to yield compound 29 (87 mg) as a powder. ¹H-NMR (500 MHz, DMSO): 11.42 (s, 1H), 8.33 (s, 1H), 8.14 (s, 1H), 7.03 (m, 2H), 6.92 (s, 2H), 6.88 (d, 1H), 6.64 (s, 3H), 4.16 (m, 2H), 2.88 (m, 1H), 2.74 (m, 4H), 2.44 (m, 3H), 2.19 (3H), 2.15 (m, 9H).

Example 30

Synthesis of 5-((4-hydroxy-3,5-dimethylbenzyl)amino)-3-((3-methyl-4-(piperidin-1-yl)phenyl)amino)-1H-pyrazole-4-carboxamide 30

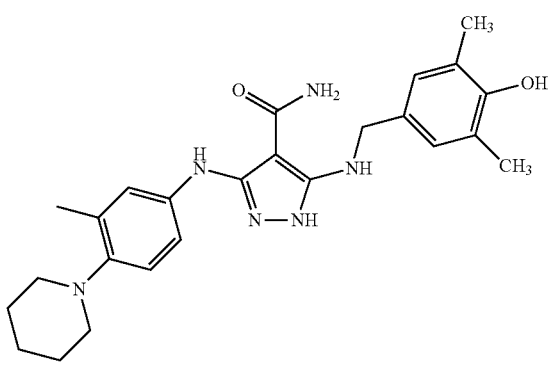

The intermediate 5-amino-3-((3-methyl-4-(piperidin-1-yl)phenyl)amino)-1H-pyrazole-4-carboxamide was prepared in a manner substantially similar to that described for A2 of Example 1.

5-amino-3-((3-methyl-4-(piperidin-1-yl)phenyl)amino)-1H-pyrazole-4-carboxamide (240 mg) was suspended in EtOH (10 mL) and acetic acid (0.5 mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (0.240 g) which was used without purification. The crude imine (51 mg) was combined with DMF (1 mL) and MeOH (0.5 mL) and treated with 2 equivalents of sodium borohydride at room temperature. After 1 hour, water was added, and the separated precipitate was collected by suction filteration, washed with water, and dried to yield compound 30 (51 mg) as a powder. ¹H-NMR (500 MHz, DMSO): 11.41 (s, 1H), 8.302 (s, 1H), 8.14 (s, 1H), 7.05 (s, 1H), 6.94 (m, 1H), 6.92 (s, 2H), 6.86 (m, 1H), 6.64 (s, 3H), 4.16 (m, 2H), 2.68 (m, 4H), 2.15 (m, 9H), 1.61 (m, 4H), 1.49 (m, 2H).

Example 31

Synthesis of 3-((4-(4-benzylpiperazin-1-yl)phenyl)amino)-5-((4-hydroxy-3,5-dimethylbenzyl)amino)-1H-pyrazole-4-carboxamide 31

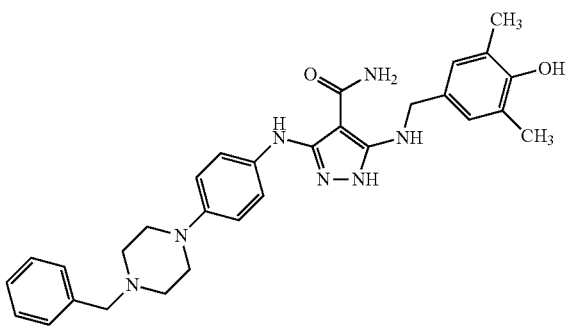

The intermediate 5-amino-3-((4-(4-benzylpiperazin-1-yl)phenyl)amino)-1H-pyrazole-4-carboxamide was prepared in a manner substantially similar to that described for A2 of Example 1.

5-amino-3-((4-(4-benzylpiperazin-1-yl)phenyl)amino)-1H-pyrazole-4-carboxamide (240 mg) was suspended in EtOH (5 mL) and acetic acid (0.5 mL). The reaction mixture was heated at 80° C. while stirring, and 1.4 equivalents of 3,5-dimethyl-4-hydroxybenzaldehyde was added. After 5 hours, the reaction mixture was cooled to room temperature. The separated solids were collected by suction filtration and rinsed with ethanol to give the crude imine product (0.489 g) which was used without purification. The crude imine (116 mg) was combined with DMF (1 mL) and MeOH (1 mL) and treated with 2 equivalents of sodium borohydride at room temperature. After 30 minutes, water was added, and the separated precipitate was collected by suction filteration, washed with water, and dried to yield compound 31 (92 mg) as a powder. ¹H-NMR (500 MHz, DMSO): 11.37 (s, 1H), 8.25 (s, 1H), 8.14 (s, 1H), 7.31 (m, 4H), 7.25 (m, 1H), 7.13 (d, 2H), 6.91 (s, 2H), 6.79 (d, 2H), 6.63 (s, 3H), 4.16 (d, 2H), 3.51 (s, 2H), 2.99 (s, 4H), 2.14 (s, 6H).

Example 32

Synthesis of 3-((4-(1,1-dioxidothiomorpholino)phenyl)amino)-5-((4-hydroxy-3,5-dimethylbenzyl)amino)-1H-pyrazole-4-carboxamide 32

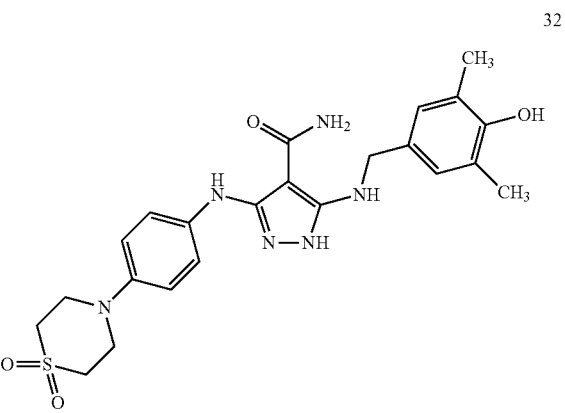 [SMILES: Cc1cc(CNc2[nH]nc(Nc3ccc(N4CCS(=O)(=O)CC4)cc3)c2C(N)=O)cc(C)c1O]

The intermediate 5-amino-3-((4-(1,1-dioxidothiomorpholino)phenyl)amino)-1H-pyrazole-4-carboxamide was prepared in a manner substantially similar to that described for A2 of Example 1.

5-amino-3-((4-(1,1-dioxidothiomorpholino)phenyl)amino)-1H-pyrazole-4-carboxamide (108 mg) was suspended in EtOH (5 mL) and acetic acid (0.5 mL). The reaction mixture was heated at 80° C. while stirring, and 1.4 equivalents of 3,5-dimethyl-4-hydroxybenzaldehyde was added. After 5 hours, the reaction mixture was cooled to room temperature. The separated solids were collected by suction filtration and rinsed with ethanol to give the crude imine product (0.240 g) which was used without purification. The crude imine (51 mg) was combined with DMF (6 mL) and MeOH (3 mL) and treated with 2 equivalents of sodium borohydride at room temperature. After 30 minutes, water was added, and the separated precipitate was collected by suction filteration, washed with water, and dried to yield compound 32 (73 mg) as a powder. $^1$H-NMR (500 MHz, DMSO): 11.40 (s, 1H), 8.34 (s, 1H), 8.16 (s, 1H), 7.17 (s, 1H), 6.90 (m, 4H), 6.65 (s, 2H), 4.16 (d, 2H), 3.58 (s, 4H), 3.12 (m, 4H), 2.14 (s, 6H).

Example 33

Synthesis of 5-((4-hydroxy-3,5-dimethylbenzyl)amino)-3-((5-(piperidin-1-yl)pyridin-2-yl)amino)-1H-pyrazole-4-carboxamide 33

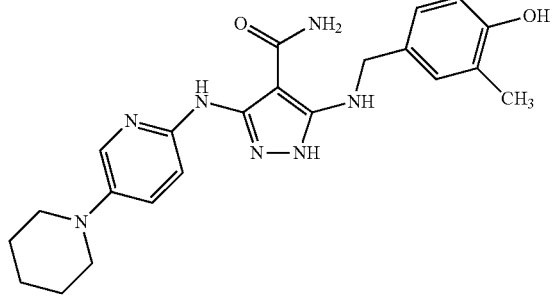

The intermediate 5-amino-3-((5-(piperidin-1-yl)pyridin-2-yl)amino)-1H-pyrazole-4-carboxamide was prepared in a manner substantially similar to that described for A2 of Example 1.

5-amino-3-((5-(piperidin-1-yl)pyridin-2-yl)amino)-1H-pyrazole-4-carboxamide (167 mg) was suspended in EtOH (10 mL) and acetic acid (0.5 mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product, which was used without purification. The crude imine was combined with DMF (1 mL) and MeOH (0.5 mL) and treated with 2 equivalents of sodium borohydride at room temperature. After 1 hour, water was added, and the separated precipitate was collected by suction filteration, washed with water, and dried to yield compound 33 (150 mg) as a powder. $^1$H-NMR (500 MHz, DMSO): 11.66 (m, 1H), 9.35 (m, 1H), 8.13 (s, 1H), 7.81 (m, 1H), 7.55 (d, 1H), 7.29 (m, 1H), 6.91 (s, 2H), 6.68 (s, 2H), 6.41 (m, 1H), 4.15 (m, 2H), 2.98 (m, 4H), 2.13 (s, 6H), 1.61 (m, 4H), 1.48 (m, 2H).

Example 34

Synthesis of 3-((4-(4-chloropiperidin-1-yl)phenyl)amino)-5-((4-hydroxy-3,5-dimethylbenzyl)amino)-1H-pyrazole-4-carboxamide 34

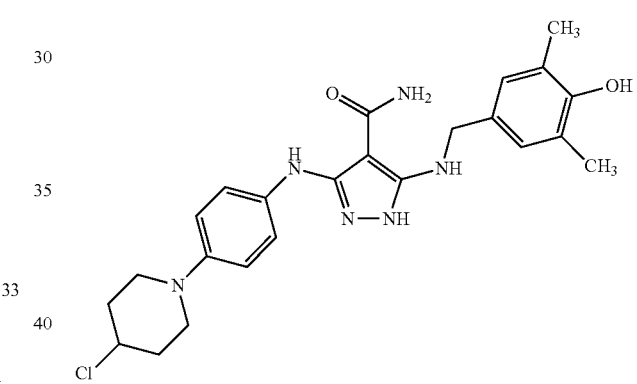

The intermediate 5-amino-3-((4-(4-chloropiperidin-1-yl)phenyl)amino)-1H-pyrazole-4-carboxamide was prepared in a manner substantially similar to that described for A2 of Example 1.

5-amino-3-((4-(4-chloropiperidin-1-yl)phenyl)amino)-1H-pyrazole-4-carboxamide (167 mg) was suspended in EtOH (10 mL) and piperidine (5 drops). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (0.320 g), which was used without purification. The crude imine (52 mg) was combined with DMF (0.5 mL) and MeOH (2 mL) and treated with 2 equivalents of sodium borohydride at room temperature. After 1 hour, water was added, and the separated precipitate was collected by suction filteration, washed with water, and dried to yield compound 34 (52 mg) as a powder. $^1$H-NMR (500 MHz, DMSO): 11.38 (s, 1H), 8.27 (s, 1H), 8.14 (s, 1H), 7.13 (d, 2H), 6.92 (s, 2H), 6.82 (d, 2H), 6.64 (m, 3H), 4.33 (m, 1H), 4.16 (d, 2H), 2.87 (m, 2H), 2.13 (m, 10H), 1.86 (m, 2H).

Example 35

Synthesis of 5-((4-hydroxy-3,5-dimethylbenzyl)amino)-3-((4-(pyrrolidin-1-ylmethyl)phenyl)amino)-1H-pyrazole-4-carboxamide 35

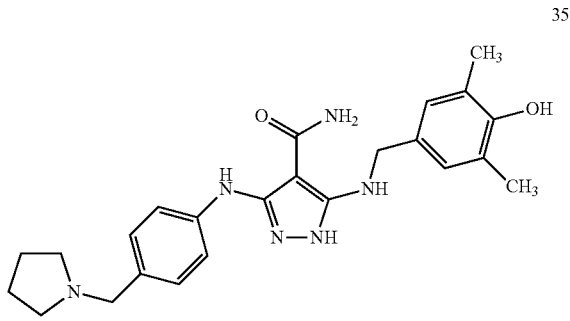 [SMILES: Cc1cc(CNc2[nH]nc(Nc3ccc(CN4CCCC4)cc3)c2C(N)=O)cc(C)c1O]

The intermediate 5-amino-3-((4-(pyrrolidin-1-ylmethyl)phenyl)amino)-1H-pyrazole-4-carboxamide was prepared in a manner substantially similar to that described for A2 of Example 1.

5-amino-3-((4-(pyrrolidin-1-ylmethyl)phenyl)amino)-1H-pyrazole-4-carboxamide (400 mg) was suspended in EtOH (5 mL) and piperidine (5 drops mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (0.420 g), which was used without purification. The crude imine (0.182 g) was combined with DMF (6 mL) and MeOH (3 mL) and treated with 2 equivalents of sodium borohydride at room temperature. After 30 minutes, water was added, and the separated precipitate was collected by suction filtration, washed with water, and dried to yield compound 35 (123 mg) as a powder. $^1$H-NMR (500 MHz, DMSO): 11.48 (s, 1H), 8.50 (s, 1H), 8.14 (s, 1H), 7.10 (m, 4H), 6.92 (s, 2H), 6.65 (s, 2H), 4.17 (d, 2H), 3.43 (s, 2H), 3.38 (m, 4H), 2.15 (s, 6H), 1.66 (m, 4H).

Example 36

Synthesis of 3-((4-(4-(dimethylamino)piperidin-1-yl)phenyl)amino)-5-((4-hydroxy-3,5-dimethylbenzyl)amino)-1H-pyrazole-4-carboxamide 36

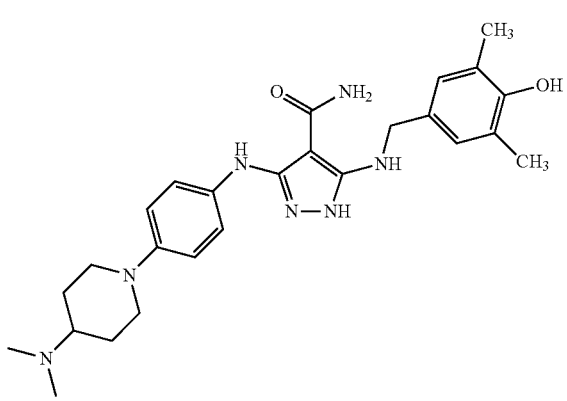

The intermediate 5-amino-3-((4-(4-(dimethylamino)piperidin-1-yl)phenyl)amino)-1H-pyrazole-4-carboxamide was prepared in a manner substantially similar to that described for A2 of Example 1.

5-amino-3-((4-(4-(dimethylamino)piperidin-1-yl)phenyl)amino)-1H-pyrazole-4-carboxamide (300 mg) was suspended in EtOH (8 mL) and piperidine (5 drops). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (0.470 g), which was used without purification. The crude imine (50 mg) was combined with DMF (2 mL) and MeOH (2 mL) and treated with 2 equivalents of sodium borohydride at room temperature. After 2 hours, water was added, and the separated precipitate was collected by suction filteration, washed with water, and dried to yield compound 36 (150 mg) as a powder.

Example 37

Synthesis of 3-((3-fluoro-4-morpholinophenyl)amino)-5-((4-hydroxy-3,5-dimethylbenzyl)amino)-1H-pyrazole-4-carboxamide 37

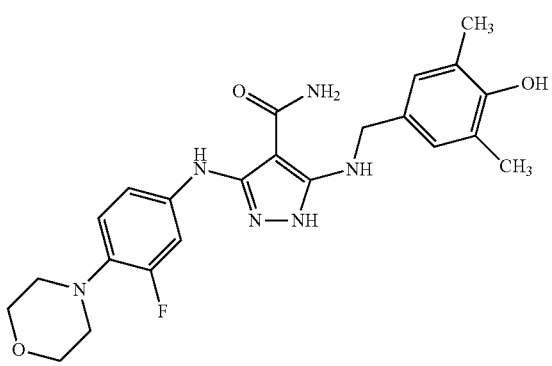

The intermediate 3-((3-fluoro-4-morpholinophenyl)amino)-5-((4-hydroxy-3,5-dimethylbenzyl)amino)-1H-pyrazole-4-carboxamide was prepared in a manner substantially similar to that described for A2 of Example 1.

3-((3-fluoro-4-morpholinophenyl)amino)-5-((4-hydroxy-3,5-dimethylbenzyl)amino)-1H-pyrazole-4-carboxamide (400 mg) was suspended in EtOH (5 mL) and piperidin (5 drops). The reaction mixture was heated at 80° C. while stirring, and 1.4 equivalents of 3,5-dimethyl-4-hydroxybenzaldehyde was added. After 20 hours, the reaction mixture was cooled to room temperature. The separated solids were collected by suction filtration and rinsed with ethanol to give the crude imine product, which was used without purification. Some of the crude imine (97 mg) was combined with DMF (1 mL) and MeOH (4 mL) and treated with 2 equivalents of sodium borohydride at room temperature. After 15 minutes, water was added, and the separated precipitate was collected by suction filteration, washed with water, and dried to yield compound 37 (75 mg) as a powder. $^1$H-NMR (500 MHz, DMSO): 2.14 (s, 6H), 2.88 (t, 4H), 3.70 (t, 4H), 4.17 (d, 2H), 6.68 (m, 3H), 6.90 (m, 4H), 7.28 (d, 1H), 8.15 (s, 1H), 8.61 (s, 1H), 11.47 (s, 1H).

Example 38

Synthesis of 5-((4-hydroxy-3,5-dimethylbenzyl)amino)-3-((4-(oxazol-5-yl)phenyl)amino)-1H-pyrazole-4-carboxamide 38

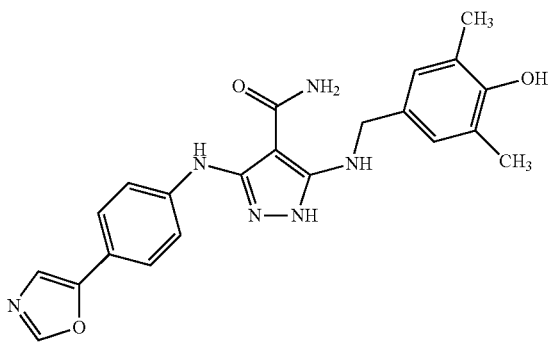

The intermediate 5-amino-3-((4-(oxazol-5-yl)phenyl)amino)-1H-pyrazole-4-carboxamide was prepared in a manner substantially similar to that described for A2 of Example 1.

5-amino-3-((4-(oxazol-5-yl)phenyl)amino)-1H-pyrazole-4-carboxamide (176 mg) was suspended in EtOH (5 mL) and piperidine (5 drops). The reaction mixture was heated at 80° C. while stirring, and 1.4 equivalents of 3,5-dimethyl-4-hydroxybenzaldehyde was added. After 18 hours, the reaction mixture was cooled to room temperature. The separated solids were collected by suction filtration and rinsed with ethanol to give the crude imine product, which was combined with DMF (1 mL) and MeOH (1 mL) and treated with 2 equivalents of sodium borohydride at room temperature. After 1 hour, water was added, and the separated precipitate was collected by suction filteration, washed with water, and dried to yield compound 38 (33 mg) as a powder. $^1$H-NMR (500 MHz, DMSO): 2.15 (s, 6H), 4.18 (d, 2H), 6.70 (m, 3H), 6.93 (s, 2H), 7.33 (d, 2H), 7.43 (s, 1H), 7.54 (d, 2H), 8.15 (s, 1H), 8.31 (s, 1H), 8.88 (s, 1H), 11.57 (s, 1H).

Example 39

Synthesis of 5-((4-hydroxy-3,5-dimethylbenzyl)amino)-3-((4-(4-(morpholine-4-carbonyl)piperazin-1-yl)phenyl)amino)-1H-pyrazole-4-carboxamide 39

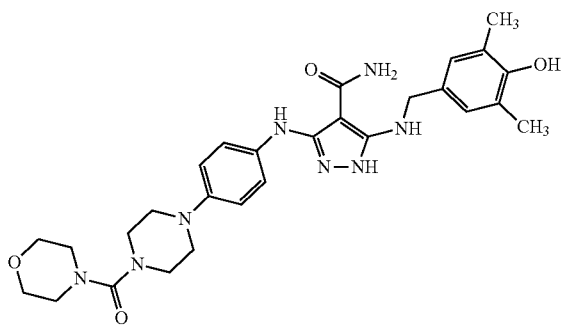

The intermediate 5-amino-3-((4-(4-(morpholine-4-carbonyl)piperazin-1-yl)phenyl)amino)-1H-pyrazole-4-carboxamide was prepared in a manner substantially similar to that described for A2 of Example 1.

5-amino-3-((4-(4-(morpholine-4-carbonyl)piperazin-1-yl)phenyl)amino)-1H-pyrazole-4-carboxamide (210 mg) was suspended in EtOH (15 mL) and piperidine (5 drops). The reaction mixture was heated at 80° C. while stirring, and 1.4 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product, which was used without purification. The crude imine was combined with DMF (1 mL) and MeOH (2 mL) and treated with 2 equivalents of sodium borohydride at room temperature. After 30 minutes, water was added, and the separated precipitate was collected by suction filteration, washed with water, and dried to yield compound 39 (41 mg) as a powder. $^1$H-NMR (500 MHz, DMSO): 11.38 (s, 1H), 8.28 (s, 1H), 8.14 (s, 1H), 7.14 (d, 2H), 6.92 (s, 2H), 6.82 (d, 2H), 6.63 (m, 3H), 4.16 (d, 2H), 3.57 (t, 4H), 3.28 (t, 4H), 3.16 (t, 4H), 2.89 (t, 4H), 2.14 (s, 6H).

Example 40

Synthesis of 3-((3-acetamidophenyl)amino)-5-((4-hydroxy-3,5-dimethylbenzyl)amino)-1H-pyrazole-4-carboxamide 40

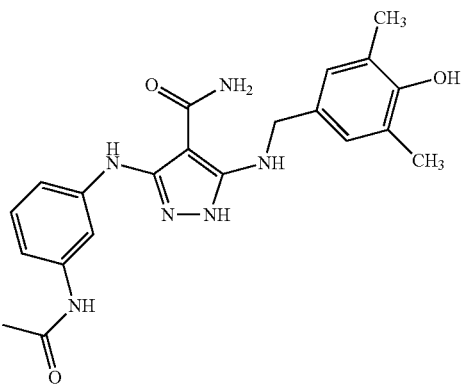

The intermediate 3-((3-acetamidophenyl)amino)-5-amino-1H-pyrazole-4-carboxamide was prepared in a manner substantially similar to that described for A2 of Example 1.

3-((3-acetamidophenyl)amino)-5-amino-1H-pyrazole-4-carboxamide (100 mg) was suspended in EtOH (8 mL) and piperidine (5 drops). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product, which was used without purification. The crude imine was combined with DMF (1 mL) and MeOH (2 mL) and treated with 2 equivalents of sodium borohydride at room temperature. After 1 hour, water was added, and the mixture was extracted with ethyl acetate, washed with water and saturated NaCl solution, dried over anhydrous sodium sulfate and evaporated to give a crude solid. The crude solide was recrystallized from acetone and water to yield compound 40 (68 mg). $^1$H-NMR (500 MHz, DMSO): 11.53 (s, 1H), 9.75 (s, 1H), 8.46 (s, 1H), 8.15 (s, 1H), 7.33 (s, 1H), 7.06 (t, 2H), 6.92 (m, 3H), 6.65 (m, 3H), 4.18 (d, 2H), 2.15 (s, 6H), 2.00 (s, 3H).

Example 41

Synthesis of 3-((3-chloro-4-(4-methylpiperazin-1-yl)phenyl)amino)-5-((4-hydroxy-3,5-dimethylbenzyl)amino)-1H-pyrazole-4-carboxamide 41

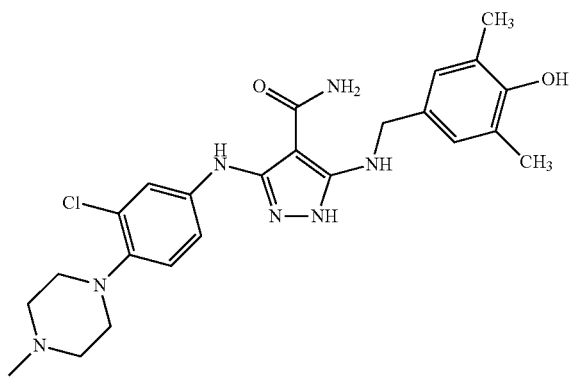

41

The intermediate 5-amino-3-((3-chloro-4-(4-methylpiperazin-1-yl)phenyl)amino)-1H-pyrazole-4-carboxamide was prepared in a manner substantially similar to that described for A2 of Example 1.

5-amino-3-((3-chloro-4-(4-methylpiperazin-1-yl)phenyl)amino)-1H-pyrazole-4-carboxamide (370 mg) was suspended in EtOH (10 mL) and piperidine (3 drops). The reaction mixture was heated at 80° C. while stirring, and 1.4 equivalents of 3,5-dimethyl-4-hydroxybenzaldehyde was added. After 17 hours, the reaction mixture was cooled to room temperature. The separated solids were collected by suction filtration and rinsed with ethanol to give the crude imine product (487 mg), which was used without purification. The crude imine (82 mg) was combined with DMF (2 mL) and MeOH (2 mL) and treated with 2 equivalents of sodium borohydride at room temperature. After 30 minutes, water was added, and the separated precipitate was collected by suction filtration, washed with water, and dried to yield compound 41 (65 mg) as a powder. $^1$H-NMR (500 MHz, DMSO): 11.50 (s, 1H), 8.59 (s, 1H), 8.15 (s, 1H), 7.55 (s, 1H), 7.02 (m, 2H), 6.92 (s, 2H), 6.69 (m, 3H), 4.16 (d, 2H), 2.86 (m, 4H), 2.45 (m, 4H), 2.21 (s, 3H), 2.14 (s, 6H).

Example 42

Synthesis of 3-((4-fluorophenyl)amino)-5-((4-hydroxy-3,5-dimethylbenzyl)amino)-1H-pyrazole-4-carboxamide 42

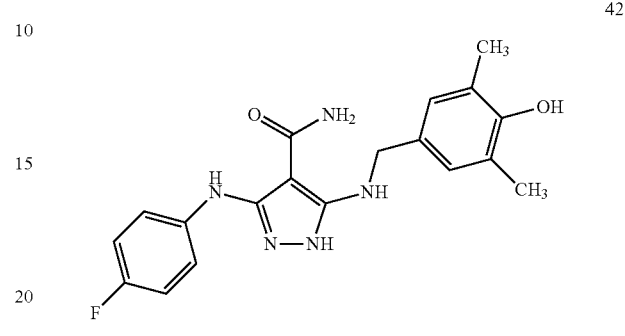

42

The intermediate 5-amino-3-((4-fluorophenyl)amino)-1H-pyrazole-4-carboxamide was prepared in a manner substantially similar to that described for A2 of Example 1.

5-amino-3-((4-fluorophenyl)amino)-1H-pyrazole-4-carboxamide (225 mg) was suspended in EtOH (5 mL) and piperidine (5 drops). The reaction mixture was heated at 80° C. while stirring, and 1.4 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product (342 mg), which was used without purification. The crude imine (70 mg) was combined with DMF (1 mL) and MeOH (1 mL) and treated with 2 equivalents of sodium borohydride at room temperature. After 3 hours, water was added, and the separated precipitate was collected by suction filteration, washed with water, and dried to yield compound 42 (63 mg) as a powder. $^1$H-NMR (500 MHz, DMSO): 11.46 (s, 1H), 8.54 (s, 1H), 8.14 (s, 1H), 7.25 (m, 2H), 7.00 (t, 2H), 6.92 (s, 2H), 6.67 (m, 3H), 4.17 (d, 2H), 2.15 (s, 6H).

Example 43

Synthesis of 3-((3-cyanophenyl)amino)-5-((4-hydroxy-3,5-dimethylbenzyl)amino)-1H-pyrazole-4-carboxamide 43

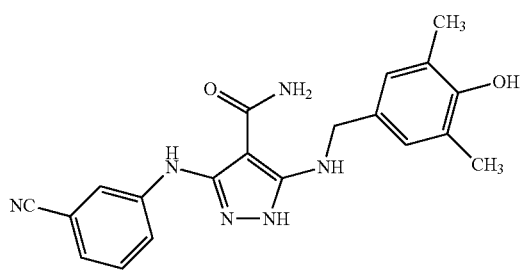

43

The intermediate 5-amino-3-((3-cyanophenyl)amino)-1H-pyrazole-4-carboxamide was prepared in a manner substantially similar to that described for A2 of Example 1.

5-amino-3-((3-cyanophenyl)amino)-1H-pyrazole-4-carboxamide (250 mg) was suspended in EtOH (5 mL) and piperidine (5 drops). The reaction mixture was heated at 80° C. while stirring, and 1.4 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product (342 mg), which was used without purification. The crude imine (64 mg) was combined with DMF (1 mL) and MeOH (1 mL) and treated with 2 equivalents of sodium borohydride at room temperature. After 3 hours, water was added, and the separated precipitate was collected by suction filteration, washed with water, and dried to yield compound 43 (47 mg) as a powder. $^1$H-NMR (500 MHz, DMSO): 9.01 (s, 1H), 8.15 (s, 1H), 7.84 (s, 1H), 7.46 (d, 1H), 7.36 (t, 1H), 7.16 (d, 2H), 6.93 (s, 2H), 6.74 (m, 3H), 4.18 (d, 2H), 2.15 (s, 6H).

Example 44

Synthesis of 5-((4-hydroxy-3,5-dimethylbenzyl)amino)-3-((4-(4-(pyrimidin-2-yl)piperazin-1-yl)phenyl)amino)-1H-pyrazole-4-carboxamide 44

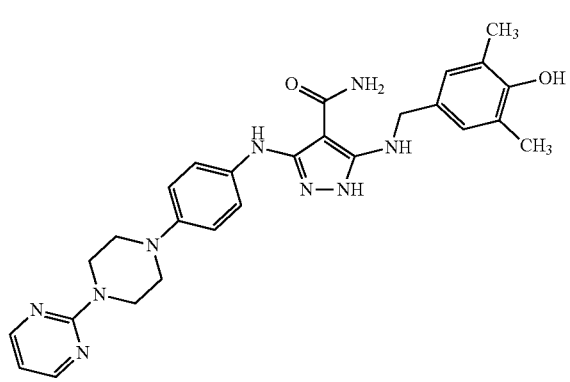

The intermediate 5-amino-3-((4-(4-(pyrimidin-2-yl)piperazin-1-yl)phenyl)amino)-1H-pyrazole-4-carboxamide was prepared in a manner substantially similar to that described for A2 of Example 1.

5-amino-3-((4-(4-(pyrimidin-2-yl)piperazin-1-yl)phenyl)amino)-1H-pyrazole-4-carboxamide (104.4 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product (141 mg), which was used without purification. The crude imine (109 mg) was combined with DMF (1 mL) and MeOH (3 mL) and treated with 2 equivalents of sodium borohydride at room temperature. After 18 hours, water was added, and the separated precipitate was collected by suction filteration, washed with water, and dried to yield compound 44 (109 mg) as a powder. $^1$H-NMR (500 MHz, DMSO): 11.38 (s, 1H), 8.38 (m, 2H), 8.29 (s, 1H), 8.13 (s, 1H), 7.16 (d, 2H), 6.92 (s, 2H), 6.87 (d, 2H), 6.64 (m, 4H), 4.16 (d, 2H), 3.86 (t, 4H), 3.05 (t, 4H), 2.14 (s, 6H).

Example 45

Synthesis of 5-((4-hydroxy-3,5-dimethylbenzyl)amino)-3-((4-(piperidin-1-ylmethyl)phenyl)amino)-1H-pyrazole-4-carboxamide 45

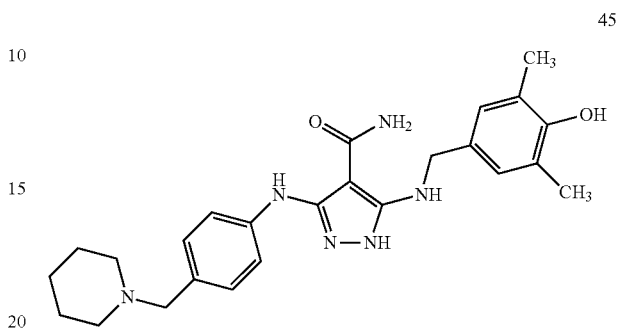

The intermediate 5-amino-3-((4-(piperidin-1-ylmethyl)phenyl)amino)-1H-pyrazole-4-carboxamide was prepared in a manner substantially similar to that described for A2 of Example 1.

5-amino-3-((4-(piperidin-1-ylmethyl)phenyl)amino)-1H-pyrazole-4-carboxamide (150 mg) was suspended in EtOH (3 mL) and piperidine (0.5 mL). The reaction mixture was heated at 80° C. while stirring, and 1.4 equivalents of 3,5-dimethyl-4-hydroxybenzaldehyde was added. After 18 hours, the reaction mixture was cooled to room temperature. The separated solids were collected by suction filtration and rinsed with ethanol to give the crude imine product (145 mg), which was used without purification. The crude imine (100 mg) was combined with DMF (2 mL) and MeOH (1 mL) and treated with 2 equivalents of sodium borohydride at room temperature. After 30 minutes, water was added, and the separated precipitate was collected by suction filteration, washed with water, and dried to yield compound 45 (100 mg) as a powder. $^1$H-NMR (500 MHz, DMSO): 11.48 (s, 1H), 7.14 (s, 2H), 7.06 (d, 2H), 6.92 (s, 2H), 6.65 (s, 3H), 4.17 (s, 2H), 3.28 (s, 4H), 2.27 (s, 4H), 2.14 (s, 6H), 1.46 (m, 4H), 1.36 (m, 2H).

Example 46

Synthesis of 5-((4-hydroxy-3,5-dimethylbenzyl)amino)-3-((4-thiomorpholinophenyl)amino)-1H-pyrazole-4-carboxamide 46

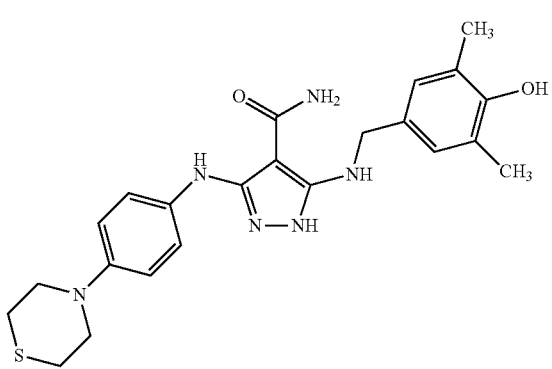

The intermediate 5-amino-3-((4-thiomorpholinophenyl)amino)-1H-pyrazole-4-carboxamide was prepared in a manner substantially similar to that described for A2 of Example 1.

5-amino-3-((4-thiomorpholinophenyl)amino)-1H-pyrazole-4-carboxamide (389 mg) was suspended in EtOH (10 mL) and acetic acid (0.5 mL). The reaction mixture was heated at 80° C. while stirring, and 1.5 equivalents of 3,5-dimethyl-4-hydroxybenzaldehyde was added. After 16 hours, the reaction mixture was cooled to room temperature. The separated solids were collected by suction filtration and rinsed with ethanol to give the crude imine product (497 mg), which was used without purification. The crude imine (135 mg) was combined with DMF (6 mL) and MeOH (2 mL) and treated with 2 equivalents of sodium borohydride at room temperature. After 30 minutes, water was added, and the crude product was titrated with EtOH at 80° C. for 1 hour. The precipitate was collected by suction filteration, washed with EtOH, and dried to yield compound 46 (105 mg) as a powder. $^1$H-NMR (500 MHz, DMSO): 11.38 (s, 1H), 8.29 (s, 1H), 8.14 9 s, 1H), 7.14 (d, 2H), 6.92 (s, 2H), 6.81 (d, 2H), 6.63 (m, 3H), 4.16 (d, 2H), 3.28 (m, 4H), 2.68 (m, 4H), 2.14 (s, 6H).

Example 47

Synthesis of 3-((4-aminophenyl)amino)-5-((4-hydroxy-3,5-dimethylbenzyl)amino)-1H-pyrazole-4-carboxamide 47

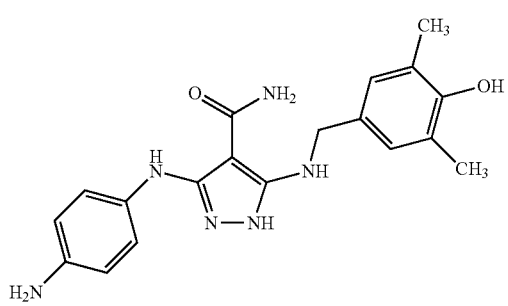

The intermediate 5-amino-3-((4-nitrophenyl)amino)-1H-pyrazole-4-carboxamide was prepared in a manner substantially similar to that described for A2 of Example 1.

5-amino-3-((4-nitrophenyl)amino)-1H-pyrazole-4-carboxamide (1.006 g) was suspended in EtOH (3 mL) and piperidine (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product (1.308 g) which was used without purification. The crude imine (100 mg) was combined with DMF (0.5 mL) and MeOH (1 mL) and treated with 2 equivalents of sodium borohydride at room temperature. After 2 hours, water was added, and the separated precipitate was collected by suction filteration, washed with water. This precipitate was dissolved in MeOH (1 mL) and THF (2 mL), treated with 10% Palladium on Carbon (20 mg) and stirred under a hydrogen atmosphere (30 psi). The suspension was collected by suction and then recrystallized from DMSO and water to yield compound 47 (18 mg). $^1$H-NMR (500 MHz, DMSO): 11.28 (s, 1H), 8.13 (s, 1H), 8.00 (s, 1H), 6.91 (s, 4H), 6.60 (s, 3H), 6.46 (d, J=9, 2H), 4.50 (s, 2H), 4.15 (d, J=6, 2H), 2.14 (s, 6H).

Example 48

Synthesis of 5-((4-hydroxy-3,5-dimethylbenzyl)amino)-3-((4-sulfamoylphenyl)amino)-1H-pyrazole-4-carboxamide 48

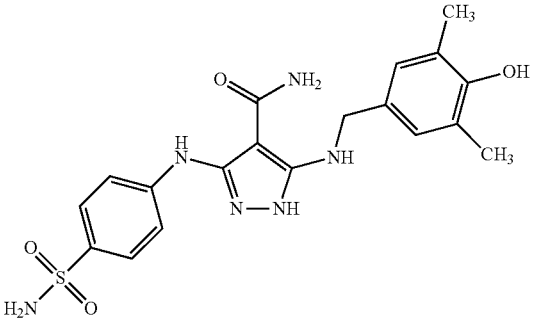

The intermediate 5-amino-3-((4-sulfamoylphenyl)amino)-1H-pyrazole-4-carboxamide was prepared in a manner substantially similar to that described for A2 of Example 1.

5-amino-3-((4-sulfamoylphenyl)amino)-1H-pyrazole-4-carboxamide (230 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 60 hours, the reaction mixture was cooled to room temperature. The separated solids were collected by suction filtration and rinsed with ethanol to give the crude imine, which was combined with DMF (1 mL) and MeOH (3 mL) and treated with 2 equivalents of sodium borohydride at room temperature. After 30 minutes, water was added, and the separated precipitate was collected by suction filteration, washed with water, and dried to yield compound 48 (244 mg) as a powder. $^1$H-NMR (500 MHz, DMSO): 11.65 (s, 1H), 9.08 (s, 1H), 8.16 (s, 1H), 7.62 (d, J=9, 2H), 7.31 (d, J=9, 2H), 7.05 (s, 2H), 6.93 (s, 2H), 6.73 (m, 3H), 4.18 (d, J=6, 2H), 2.15 (s, 6H).

Example 49

Synthesis of 5-((4-hydroxy-3,5-dimethylbenzyl)amino)-3-((6-(4-(pyrrolidin-1-yl)piperidin-1-yl)pyridin-3-yl)amino)-1H-pyrazole-4-carboxamide 49

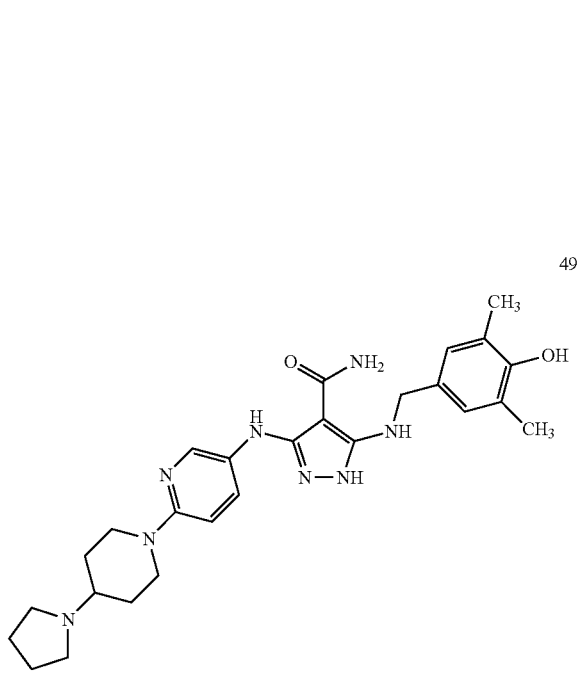 [SMILES: Cc1cc(CNc2[nH]nc(Nc3ccc(N4CCC(N5CCCC5)CC4)nc3)c2C(N)=O)cc(C)c1O]

The intermediate 5-amino-3-((6-(4-(pyrrolidin-1-yl)piperidin-1-yl)pyridin-3-yl)amino)-1H-pyrazole-4-carboxamide was prepared in a manner substantially similar to that described for A2 of Example 1.

5-amino-3-((6-(4-(pyrrolidin-1-yl)piperidin-1-yl)pyridin-3-yl)amino)-1H-pyrazole-4-carboxamide (46 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 36 hours, the reaction mixture was cooled to room temperature. The separated solids were collected by suction filtration and rinsed with ethanol to give the crude imine product, which was combined with DMF (1.5 mL) and MeOH (2.5 mL) and treated with 2 equivalents of sodium borohydride at room temperature. After 48 hours, water was added, and the separated precipitate was collected by suction filteration, washed with water, and dried to yield compound 49 (29 mg) as a powder. $^1$H-NMR (500 MHz, DMSO): 8.21 and 8.15 (s, s, 3H), 7.60 and 7.54 (d, s, 1H), 6.91 (s, 1H), 6.81 and 6.73 (d, J=9 Hz, d, J=9 Hz, 1H), 6.69 and 6.66 (s, s, 3H), 4.16, 4.05 and 3.99 (m, m, m, 4H), 2.74 (m, 3H), 2.14 (s, 6H), 1.87 (d, J=10 Hz, 2H), 1.67 (s, 4H), 1.38 (m, 2H).

Example 50

Synthesis of 3-((4-(dimethylamino)phenyl)amino)-5-((4-hydroxy-3,5-dimethylbenzyl)amino)-1H-pyrazole-4-carboxamide 50

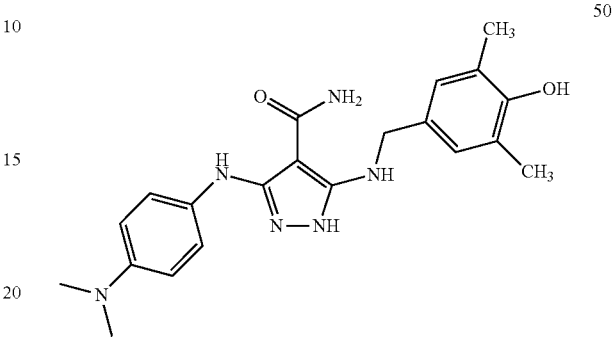

The intermediate 5-amino-3-((4-(dimethylamino)phenyl)amino)-1H-pyrazole-4-carboxamide was prepared in a manner substantially similar to that described for A2 of Example 1.

5-amino-3-((4-(dimethylamino)phenyl)amino)-1H-pyrazole-4-carboxamide (95 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product, which was combined with DMF (0.5 mL) and MeOH (2.5 mL) and treated with 2 equivalents of sodium borohydride at room temperature. After 3 hours, water was added, and the separated precipitate was collected by suction filteration, washed with water, and dried to yield compound 50 (93 mg) as a powder. $^1$H-NMR (500 MHz, DMSO): 11.33 (s, 1H), 8.15 (m, 2H), 7.13 (d, J=7, 2H), 6.92 (s, 2H), 6.65 (m, 5H), 4.16 (d, J=6, 2H), 2.77 (s, 6H), 2.14 (s, 6H).

Example 51

Synthesis of 5-((4-hydroxy-3,5-dimethylbenzyl)amino)-3-((4-(morpholinomethyl)phenyl)amino)-1H-pyrazole-4-carboxamide 51

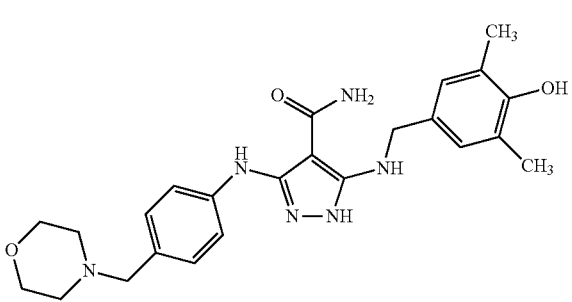

The intermediate 5-amino-3-((4-(morpholinomethyl)phenyl)amino)-1H-pyrazole-4-carboxamide was prepared in a manner substantially similar to that described for A2 of Example 1.

5-amino-3-((4-(morpholinomethyl)phenyl)amino)-1H-pyrazole-4-carboxamide (122 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product, which was combined with DMF (1 mL) and MeOH (3 mL) and treated with 2 equivalents of sodium borohydride at room temperature. After 24 hours, water was added, and the separated precipitate was collected by suction filtration, washed with water, and dried to yield compound 51 (110 mg) as a powder. $^1$H-NMR (500 MHz, DMSO): 11.48 (s, 1H) 8.54 (s, 1H), 8.15 (s, 1H), 7.16 (d, J=8, 2H), 7.08 (d, J=8, 2H), 6.92 (s, 2H), 6.66 (s, 3H), 4.17 (d, J=6, 2H), 3.55 (m, 4H), 2.31 (s, 4H), 2.14 (s, 6H).

Example 52

Synthesis of 5-((4-hydroxy-3,5-dimethylbenzyl)amino)-3-((3-methoxyphenyl)amino)-1H-pyrazole-4-carboxamide 52

The intermediate 5-amino-3-((3-methoxyphenyl)amino)-1H-pyrazole-4-carboxamide was prepared in a manner substantially similar to that described for A2 of Example 1.

5-amino-3-((3-methoxyphenyl)amino)-1H-pyrazole-4-carboxamide (122 mg) was suspended in EtOH (3 mL) and acetic acid (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product, which was then combined with DMF (0.5 mL) and MeOH (2.5 mL) and treated with 2 equivalents of sodium borohydride at room temperature. After 4 hours, water was added, and the separated precipitate was collected by suction filteration, washed with water, and dried to yield compound 52 (35 mg) as a powder. $^1$H-NMR (500 MHz, DMSO): 11.52 (s, 1H), 8.63 (s, 1H), 8.15 (s, 1H), 7.05 (t, J=9 Hz, 1H), 6.95 (s, 1H), 6.92 (s, 2H), 6.69 (m, 4H), 6.33 (d, J=8 Hz, 1H), 4.17 (d, J=6 Hz, 2H), 3.69 (s, 3H), 2.14 (s, 6H).

Example 53

Synthesis of 3-((4-(4-fluorobenzamido)phenyl)amino)-5-((4-hydroxy-3,5-dimethylbenzyl)amino)-1H-pyrazole-4-carboxamide 53

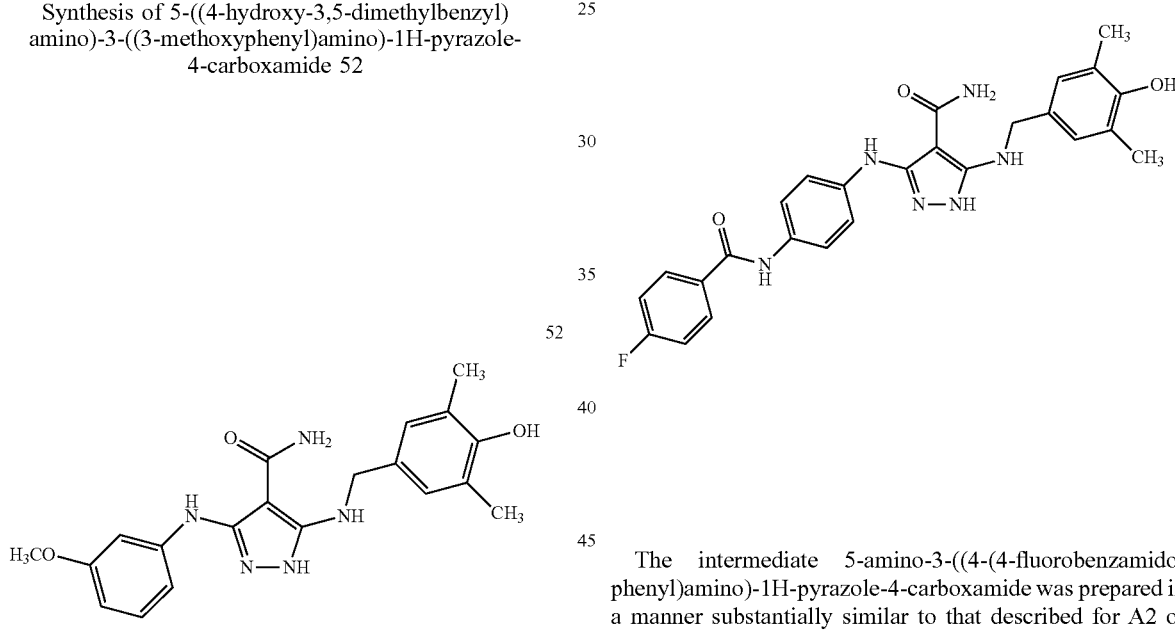

The intermediate 5-amino-3-((4-(4-fluorobenzamido)phenyl)amino)-1H-pyrazole-4-carboxamide was prepared in a manner substantially similar to that described for A2 of Example 1.

5-amino-3-((4-(4-fluorobenzamido)phenyl)amino)-1H-pyrazole-4-carboxamide (84 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 18 hours, the reaction mixture was cooled to room temperature. The separated solids were collected by suction filtration and rinsed with ethanol to give the crude imine product, which was then combined with DMF (1 mL) and MeOH (2 mL) and treated with 2 equivalents of sodium borohydride at room temperature. After 15 minutes, water was added, and the separated precipitate was collected by suction filteration, washed with water, and dried to yield compound 53 (97 mg) as a powder. $^1$H-NMR (500 MHz, DMSO): 11.47 (s, 1H), 10.04 (s, 1H), 8.59 (s, 1H), 8.16 (s, 1H), 8.01 (m, 2H), 7.54 (d, J=9, 2H), 7.34 (t, J=18 Hz, 2H), 7.23 (d, J=9 Hz, 2H), 6.93 (s, 2H), 6.68 (s, 3H), 8.18 (d, J=6 Hz, 2H), 2.15 (s, 6H).

Example 54

Synthesis of 3-((4-(1H-pyrazol-3-yl)phenyl)amino)-5-((4-hydroxy-3,5-dimethylbenzyl)amino)-1H-pyrazole-4-carboxamide 54

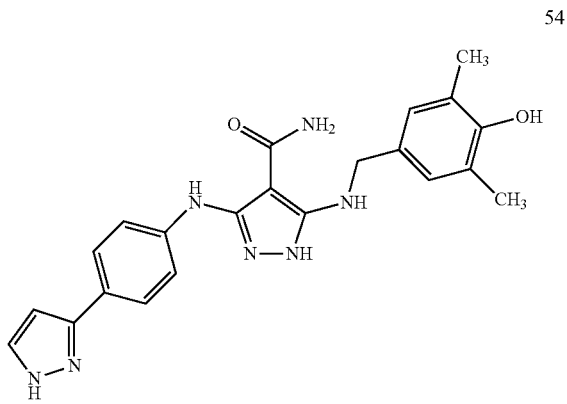 [SMILES: Cc1cc(CNc2[nH]nc(Nc3ccc(-c4cc[nH]n4)cc3)c2C(N)=O)cc(C)c1O]

The intermediate 3-((4-(1H-pyrazol-3-yl)phenyl)amino)-5-amino-1H-pyrazole-4-carboxamide was prepared in a manner substantially similar to that described for A2 of Example 1.

3-((4-(1H-pyrazol-3-yl)phenyl)amino)-5-amino-1H-pyrazole-4-carboxamide (515 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product which then combined with DMF (0.5 mL) and MeOH (1.5 mL) and treated with 2 equivalents of sodium borohydride at room temperature. After 24 hour, water was added, and the separated precipitate was collected by suction filteration, washed with water, and dried to yield compound 54 (19 mg) as a powder. $^1$H-NMR (500 MHz, DMSO): 13.02 (broad s, 0.4H), 12.65 (broad s, 0.6H), 11.52 (s, 1H), 8.90-8.60 (2 broad s, 1H), 8.16 (s, 1H), 7.80-7.18 (m, 5H), 6.93 (s, 2H), 6.69 (s, 3H), 6.53 (m, 1H), 4.18 (d, 2H), 2.15 (s, 6H).

Example 55

Synthesis of 5-((4-hydroxy-3,5-dimethylbenzyl)amino)-3-((4-(2-methoxybenzamido)phenyl)amino)-1H-pyrazole-4-carboxamide 55

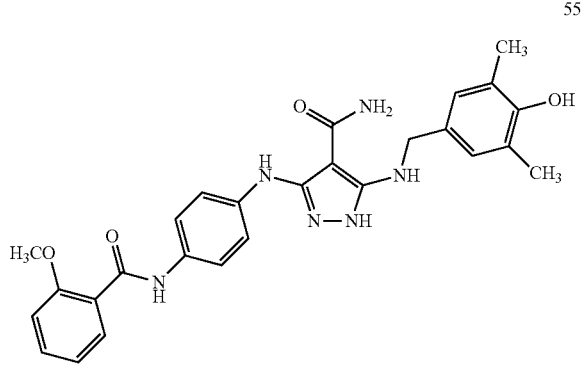 [SMILES: COc1ccccc1C(=O)Nc1ccc(Nc2n[nH]c(NCc3cc(C)c(O)c(C)c3)c2C(N)=O)cc1]

5-amino-3-((4-(2-methoxybenzamido)phenyl)amino)-1H-pyrazole-4-carboxamide was prepared in a manner substantially similar to that described for A2 of Example 1.

5-amino-3-((4-(2-methoxybenzamido)phenyl)amino)-1H-pyrazole-4-carboxamide (49 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product which then combined with DMF (0.5 mL) and MeOH (2.5 mL) and treated with 2 equivalents of sodium borohydride at room temperature. After 3 hours, water was added, and the separated precipitate was collected by suction filteration, washed with water, and dried to yield compound 54 (34 mg) as a powder. $^1$H-NMR (500 MHz, DMSO): 11.46 (s, 1H), 9.88 (s, 1H), 8.59 (s, 1H), 8.16 (s, 1H), 7.65 (d, J=7 Hz, 1H), 7.54 (d, J=9 Hz, 2H), 7.48 (t, J=8 Hz, 1H), 7.23 (d, J=9 Hz, 2H), 7.16 (d, J=8 Hz, 1H), 7.05 (t, J=8 Hz, 1H), 6.93 (s, 2H), 6.68 (s, 3H), 4.18 (d, J=6 Hz, 2H), 3.90 (s, 3H), 2.15 (s, 6H).

Example 56

Synthesis of 5-((4-hydroxy-3,5-dimethylbenzyl)amino)-3-((4-(3-methoxybenzamido)phenyl)amino)-1H-pyrazole-4-carboxamide 56

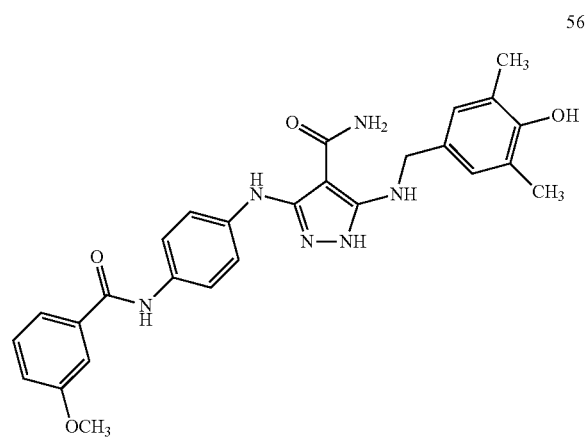 [SMILES: COc1cccc(C(=O)Nc2ccc(Nc3n[nH]c(NCc4cc(C)c(O)c(C)c4)c3C(N)=O)cc2)c1]

The intermediate 5-amino-3-((4-(3-methoxybenzamido)phenyl)amino)-1H-pyrazole-4-carboxamide was prepared in a manner substantially similar to that described for A2 of Example 1.

5-amino-3-((4-(3-methoxybenzamido)phenyl)amino)-1H-pyrazole-4-carboxamide (85 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product which was then combined with DMF (0.5 mL) and MeOH (2.5 mL) and treated with 2 equivalents of sodium borohydride at room temperature. After 6 hours, water was added, and the separated precipitate was collected by suction filteration, washed with water, and dried to yield compound 56 (75 mg) as a powder. $^1$H-NMR (500 MHz, DMSO): 11.82 (s, 1H), 10.00 (s, 1H), 8.59 (s, 1H), 8.16 (s, 1H), 7.54 (m, 3H), 7.47 (m, 1H), 7.42 (t, J=8 Hz, 1H), 7.23 (d, J=8 Hz, 2H), 7.13 (dd, 1H), 6.93 (s, 2H), 6.68 (s, 3H), 4.18 (d, J=6 Hz, 2H), 3.83 (s, 3H), 2.15 (s, 6H).

Example 57

Synthesis of 5-((4-hydroxy-3,5-dimethylbenzyl)amino)-3-((4-(4-methoxybenzamido)phenyl)amino)-1H-pyrazole-4-carboxamide 57

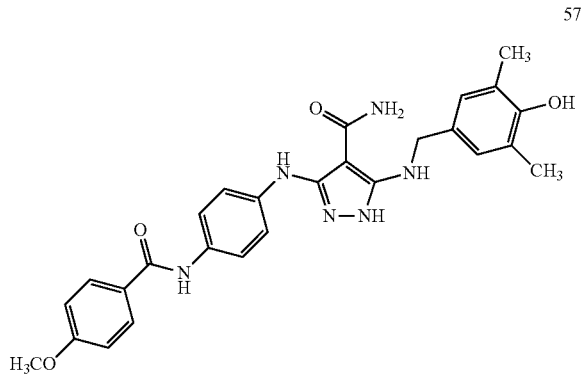 [SMILES: COc1ccc(C(=O)Nc2ccc(Nc3n[nH]c(NCc4cc(C)c(O)c(C)c4)c3C(N)=O)cc2)cc1]

The intermediate 5-amino-3-((4-(4-methoxybenzamido)phenyl)amino)-1H-pyrazole-4-carboxamide was prepared in a manner substantially similar to that described for A2 of Example 1.

5-amino-3-((4-(4-methoxybenzamido)phenyl)amino)-1H-pyrazole-4-carboxamide (73 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product which was then combined with DMF (0.5 mL) and MeOH (2.5 mL) and treated with 2 equivalents of sodium borohydride at room temperature. After 1 hour, water was added, and the separated precipitate was collected by suction filteration, washed with water, and dried to yield compound 57 (69 mg) as a powder. $^1$H-NMR (500 MHz, DMSO): 11.80 (s, 1H), 9.87 (s, 1H), 8.56 (s, 1H), 8.16 (s, 1H), 7.94 (m, 2H), 7.54 (d, J=9 Hz, 2H), 7.22 (d, J=8 Hz, 2H), 7.05 (m, 2H), 6.93 (s, 2H), 6.68 (s, 3H), 4.18 (d, J=6 Hz, 2H), 3.84 (m, 3H), 2.15 (s, 1H).

Example 58

Synthesis of 5-((4-hydroxy-3,5-dimethylbenzyl)amino)-3-((4-(4-isopropylpiperidin-1-yl)phenyl)amino)-1H-pyrazole-4-carboxamide 58

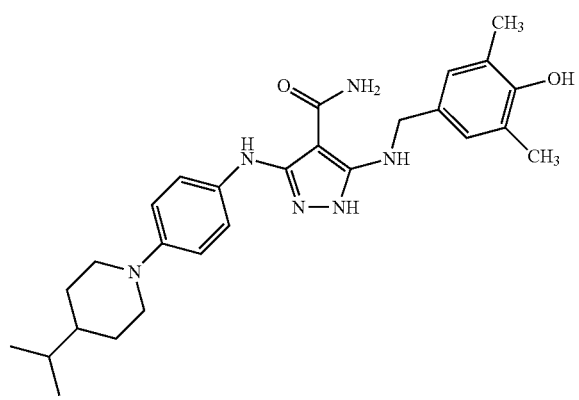

The intermediate 5-amino-3-((4-(4-isopropylpiperidin-1-yl)phenyl)amino)-1H-pyrazole-4-carboxamide was prepared in a manner substantially similar to that described for A2 of Example 1.

5-amino-3-((4-(4-isopropylpiperidin-1-yl)phenyl)amino)-1H-pyrazole-4-carboxamide (151 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 22 hours, the reaction mixture was cooled to room temperature. The separated solids were collected by suction filtration and rinsed with ethanol to give the crude imine product which was then combined with DMF (1 mL) and MeOH (3 mL) and treated with 2 equivalents of sodium borohydride at room temperature. After 24 hours, water was added, and the separated precipitate was collected by suction filteration, washed with water, and dried to yield compound 58 (142 mg) as a powder. $^1$H-NMR (500 MHz, DMSO): 11.36 (s, 1H), 8.22 (s, 1H), 8.13 (s, 1H), 7.12 (d, J=9 Hz, 2H), 6.92 (s, 2H), 8.79 (d, J=9 Hz, 2H), 6.63 (m, 3H), 4.16 (d, J=6 Hz, 2H), 5.50 (d, J=12 Hz, 2H), 2.46 (m, 2H), 2.14 (s, 6H), 1.71 (d, 2H), 1.44 (m, 1H), 1.28 (m, 2H), 1.08 (m, 1H), 0.88 (d, J=7 Hz, 6H).

Example 59

Synthesis of 5-((4-hydroxy-3,5-dimethylbenzyl)amino)-3-((4-(3-oxomorpholino)phenyl)amino)-1H-pyrazole-4-carboxamide 59

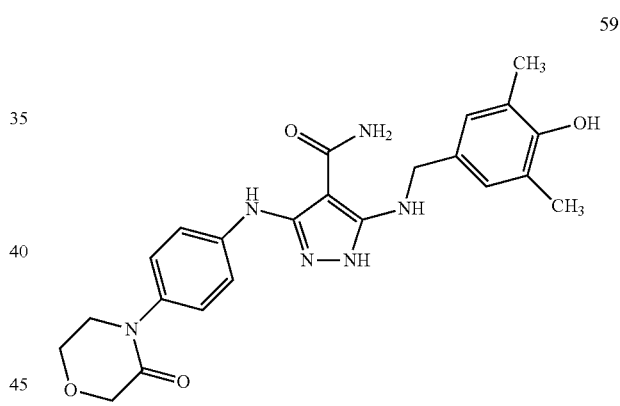

The intermediate 5-amino-3-((4-(3-oxomorpholino)phenyl)amino)-1H-pyrazole-4-carboxamide was prepared in a manner substantially similar to that described for A2 of Example 1.

5-amino-3-((4-(3-oxomorpholino)phenyl)amino)-1H-pyrazole-4-carboxamide (400 mg) was suspended in EtOH (8 mL) and piperidine (5 drops). The reaction mixture was heated at 80° C. while stirring, and 1.4 equivalents of 3,5-dimethyl-4-hydroxybenzaldehyde was added. After 20 hours, the reaction mixture was cooled to room temperature. The separated solids were collected by suction filtration and rinsed with ethanol to give the crude imine product. Some of the crude imine (50 mg) was combined with DMF (1 mL) and MeOH (1 mL) and treated with 2 equivalents of sodium borohydride at room temperature. After 18 hours, water was added, and the separated precipitate was collected by suction filteration, washed with water, and dried to yield compound 59 (36 mg) as a powder. $^1$H-NMR (500 MHz, DMSO): 2.15 (s, 6H), 3.64 (t, 2H), 3.94 (t, 2H), 4.15 (s, 2H), 4.18 (d, 2H), 6.68 (m, 3H), 6.93 (s, 2H), 7.15 (t, 2H), 7.22 (d, 2H), 8.15 (s, 1H), 8.63 (s, 1H), 11.53 (s, 1H).

Example 61

Synthesis of 3-((4-(cyanomethyl)phenyl)amino)-5-((4-hydroxy-3,5-dimethylbenzyl)amino)-1H-pyrazole-4-carboxamide 61

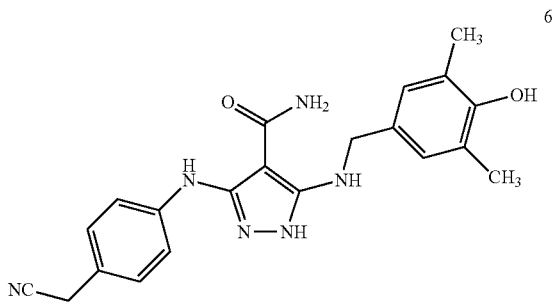

61

The intermediate 5-amino-3-((4-(cyanomethyl)phenyl)amino)-1H-pyrazole-4-carboxamide was prepared in a manner substantially similar to that described for A2 of Example 1.

5-amino-3-((4-(cyanomethyl)phenyl)amino)-1H-pyrazole-4-carboxamide (86 mg) was suspended in EtOH (5 mL) and acetic acid (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product. A portion of the crude imine product was then combined with DMF (0.5 mL) and MeOH (1.5 mL) and treated with 2 equivalents of sodium borohydride at room temperature. After 2 hours, water was added, and the separated precipitate was collected by suction filtration, washed with water, and dried to yield compound 61 (62 mg) as a powder. $^1$H-NMR (500 MHz, DMSO): 11.51 (s, 1H), 8.65 (s, 1H), 8.14 (s, 1H), 7.24 (d, J=9 Hz, 2H), 7.14 (d, J=9 Hz, 2H), 6.92 (s, 2H), 6.67 (m, 3H), 4.18 (d, J=6 Hz, 2H), 3.87 (s, 2H), 2.15 (s, 6H).

Example 62

Synthesis of 5-((4-hydroxy-3,5-dimethylbenzyl)amino)-3-((4-(4-(trifluoromethyl)benzamido)phenyl)amino)-1H-pyrazole-4-carboxamide 62

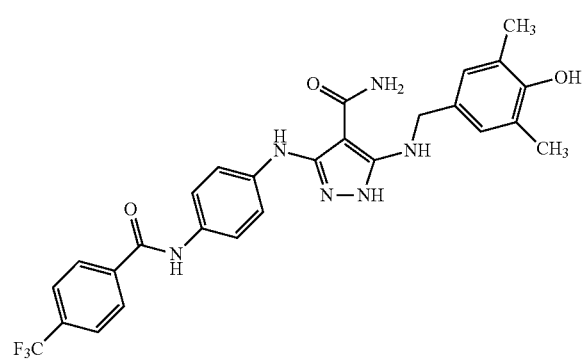

62

The intermediate 5-amino-3-((4-(4-(trifluoromethyl)benzamido)phenyl)amino)-1H-pyrazole-4-carboxamide was prepared in a manner substantially similar to that described for A2 of Example 1.

5-amino-3-((4-(4-(trifluoromethyl)benzamido)phenyl)amino)-1H-pyrazole-4-carboxamide (101 mg) was suspended in EtOH (5 mL) and acetic acid (5 drops). The reaction mixture was heated at 80° C. while stirring, and 1.5 equivalents of 3,5-dimethyl-4-hydroxybenzaldehyde was added. After 24 hours, the reaction mixture was cooled to room temperature. The separated solids were collected by suction filtration and rinsed with ethanol to give the crude imine product which was then combined with DMF (1 mL) and MeOH (3 mL) and treated with 2 equivalents of sodium borohydride at room temperature. After 2 hours, water was added, and the separated precipitate was collected by suction filteration, washed with water, and dried to yield compound 62 (15 mg) as a powder. $^1$H-NMR (500 MHz, DMSO): 11.48 (s, 1H), 10.26 (s, 1H), 8.63 (s, 1H), 8.16 (s, 1H), 8.13 (d, J=8 Hz, 2H), 7.90 (d, J=9 Hz, 2H), 7.58 (d, 2H), 7.25 (d, J=7 Hz, 2H), 6.93 (s, 2H), 6.69 (s, 3H), 4.18 (d, J=7 Hz, 2H), 2.15 (s, 6H).

Example 63

Synthesis of 5-((4-hydroxy-3,5-dimethylbenzyl)amino)-3-((4-(4-methylpiperidin-1-yl)phenyl)amino)-1H-pyrazole-4-carboxamide 63

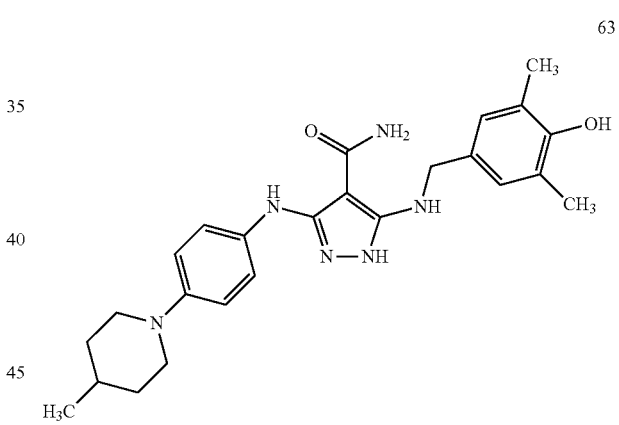

63

The intermediate 5-amino-3-((4-(4-methylpiperidin-1-yl)phenyl)amino)-1H-pyrazole-4-carboxamide was prepared in a manner substantially similar to that described for A2 of Example 1.

5-amino-3-((4-(4-methylpiperidin-1-yl)phenyl)amino)-1H-pyrazole-4-carboxamide (114 mg) was suspended in EtOH (5 mL) and piperidine (5 drops). The reaction mixture was heated at 80° C. while stirring, and 1.5 equivalents of 3,5-dimethyl-4-hydroxybenzaldehyde was added. After 21 hours, the reaction mixture was cooled to room temperature. The separated solids were collected by suction filtration and rinsed with ethanol to give the crude imine product, which was then combined with DMF (0.5 mL) and MeOH (2 mL) and treated with 2 equivalents of sodium borohydride at room temperature. After 30 minutes, water was added, and the separated precipitate was collected by suction filteration, washed with water, and dried to yield compound 63 (30 mg) as a powder. $^1$H-NMR (500 MHz, DMSO): 11.36 (s, 1H), 8.21 (s, 2H), 8.12 (s, 2H), 7.10 (s, 2H), 6.92 (s, 2H), 6.79 (d, 2H), 6.62 (s, 2H), 4.16 (d, 2H), 3.43 (d, 2H), 2.54 (s, 1H), 2.14 (s, 6H), 1.67 (d, 2H), 1.43 (m, 1H), 1.26 (m, 2H), 0.93 (d, 3H).

Example I

Mass Spectrometry Data for Kinase Inhibitors

Mass spectrometry data for the kinase inhibitors are summarized in Table 1 below.

TABLE 1

| Compound | MS positive ion mode (m/z) |
|---|---|
| 1 | 478 |
| 2 | 471 |
| 3 | 437 |
| 4 | 465 |
| 5 | 472 |
| 6 | 417 |
| 7 | 438 |
| 8 | 451 |
| 9 | 429 |
| 10 | 450 |
| 11 | 439 |
| 12 | 452 |
| 13 | 493 |
| 14 | 465 |
| 15 | 499 |
| 16 | 429 |
| 17 | 512 |
| 18 | 428 |
| 19 | 418 |
| 20 | 382 |
| 21 | 408 |
| 22 | 392 |
| 23 | 532 |
| 24 | 533 |
| 25 | 453 |
| 26 | 466 |
| 27 | 435 |
| 28 | 499 |
| 29 | 464 |
| 30 | 449 |
| 31 | 526 |
| 32 | 485 |
| 33 | 436 |
| 34 | 469 |
| 35 | 364 |
| 36 | 478 |
| 37 | 427 |
| 38 | 391 |
| 39 | 521 |
| 40 | 381 |
| 41 | 456 |
| 42 | 341 |
| 43 | 349 |
| 44 | 514 |
| 45 | 449 |
| 46 | 453 |
| 47 | 367 |
| 48 | 461 |
| 49 | 505 |
| 50 | 395 |
| 51 | 450 |
| 52 | 382 |
| 53 | 489 |
| 54 | 418 |
| 55 | 501 |
| 56 | 499 |
| 57 | 499 |
| 58 | 477 |
| 59 | 451 |
| 61 | 391 |
| 62 | 539 |
| 63 | 449 |

Example II

Enzymatic Assays for Kinase Inhibitory Activity

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for quantitative PCR (qPCR) detection.

Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Most $K_d$ values were determined using a compound top concentration=30,000 nM. If the initial $K_d$ determined was <0.5 nM, (the lowest concentration tested), the measurement was repeated with a serial dilution starting at a lower top concentration. A more detailed description of this assay may be found in Fabian, M. A. et al. *Nat. Biotechnol.* 2005, 23, 329-336, which is incorporated herein in its entirety.

The biological results of inhibition of the kinase domain protein of RC kinase (RCK) and JAK2 and JAK3 are summarized in Tables 2 and 3, wherein A represents a $K_d$ of <50 nM; B represents 50 nM<$K_d$<100 nM; C represents 100 nM<$K_d$<1000 nM; and D represents a $K_d$>1000 nM.

Additionally, RCK:JAK2 selectivity, as measured by the ratio $K_d$ (JAK2): $K_d$(RCK) is represented as follows: A represents $K_d$ (JAK2): $K_d$ (RCK)>100; B represents 10<$K_d$ (JAK2): $K_d$ (RCK)<100; C represents 1<$K_d$ (JAK2): $K_d$ (RCK)<10; and D represents $K_d$(JAK2): $K_d$ (RCK)<1.

Similarly, RCK:JAK3 selectivity, as measured by the ratio $K_d$ (JAK3): $K_d$ (RCK) is represented as follows: A represents $K_d$ (JAK3): $K_d$ (RCK)>100; B represents 10<$K_d$ (JAK3): $K_d$ (RCK)<100; C represents 1<$K_d$ (JAK3): $K_d$ (RCK)<10; and D represents $K_d$ (JAK3): $K_d$(RCK)<1.

TABLE 2

| Compound | RCK Activity Level | JAK2 Activity Level | JAK3 Activity Level | RCK: JAK2 selectivity ratio | RCK: JAK3 selectivity ratio |
|---|---|---|---|---|---|
| 1 | A | C | C | A | A |
| 2 | A | C | D | B | A |
| 3 | A | C | D | B | A |

TABLE 2-continued
| Compound | RCK Activity Level | JAK2 Activity Level | JAK3 Activity Level | RCK: JAK2 selectivity ratio | RCK: JAK3 selectivity ratio |
| --- | --- | --- | --- | --- | --- |
| 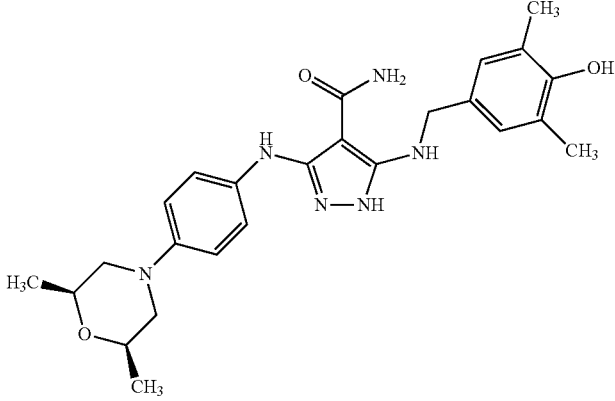 [SMILES: Cc1cc(CNc2[nH]nc(Nc3ccc(N4C[C@@H](C)O[C@@H](C)C4)cc3)c2C(N)=O)cc(C)c1O]<br>4 | C | D | D | B | B |
| 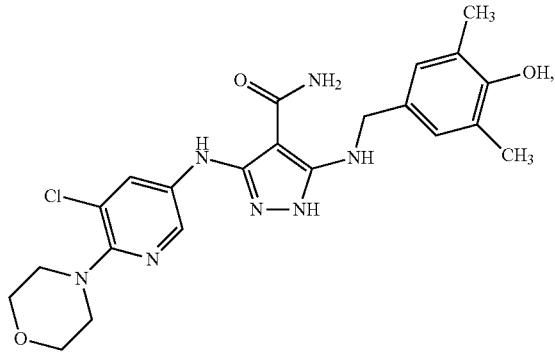 [SMILES: Cc1cc(CNc2[nH]nc(Nc3cnc(N4CCOCC4)c(Cl)c3)c2C(N)=O)cc(C)c1O]<br>5 | C | D | D | B | B |
| 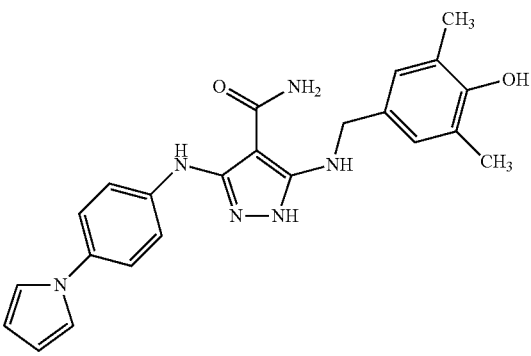 [SMILES: Cc1cc(CNc2[nH]nc(Nc3ccc(-n4cccc4)cc3)c2C(N)=O)cc(C)c1O]<br>6 | A | D | D | A | A |

TABLE 2-continued
| Compound | RCK Activity Level | JAK2 Activity Level | JAK3 Activity Level | RCK:JAK2 selectivity ratio | RCK:JAK3 selectivity ratio |
|---|---|---|---|---|---|
| 7 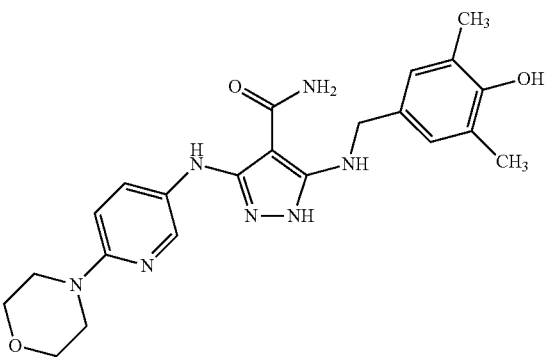 [SMILES: Cc1cc(CNc2[nH]nc(Nc3ccc(N4CCOCC4)nc3)c2C(N)=O)cc(C)c1O] | B | C | D | C | B |
| 8 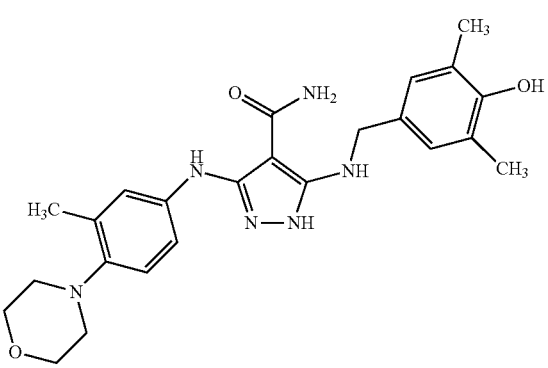 [SMILES: Cc1cc(Nc2n[nH]c(NCc3cc(C)c(O)c(C)c3)c2C(N)=O)ccc1N1CCOCC1] | B | D | D | B | B |
| 9 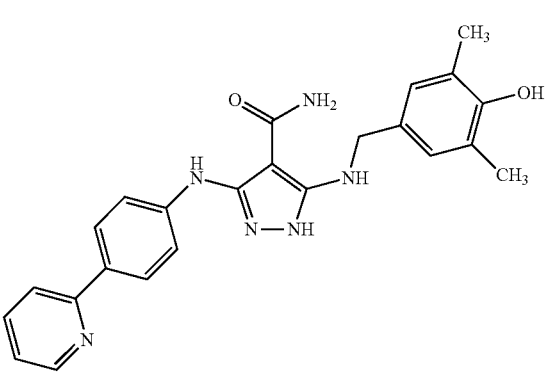 [SMILES: Cc1cc(CNc2[nH]nc(Nc3ccc(-c4ccccn4)cc3)c2C(N)=O)cc(C)c1O] | B | D | D | B | A |

TABLE 2-continued
| Compound | RCK Activity Level | JAK2 Activity Level | JAK3 Activity Level | RCK:JAK2 selectivity ratio | RCK:JAK3 selectivity ratio |
| --- | --- | --- | --- | --- | --- |
| 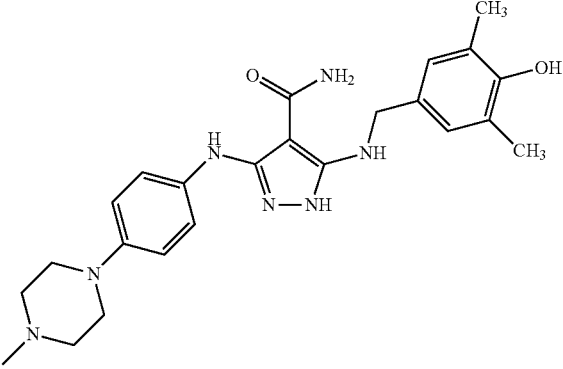 [SMILES: Cc1cc(CNc2[nH]nc(Nc3ccc(N4CCN(C)CC4)cc3)c2C(N)=O)cc(C)c1O]<br>10 | B | D | D | B | A |
| 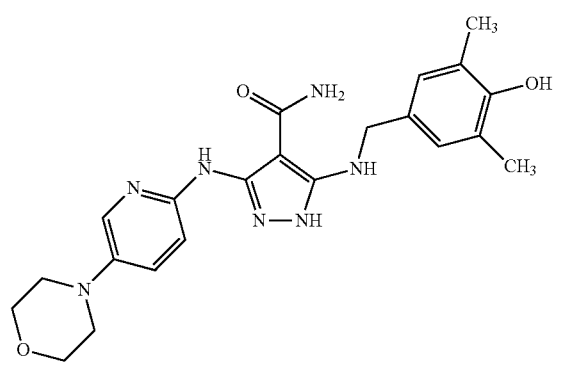 [SMILES: Cc1cc(CNc2[nH]nc(Nc3ccc(N4CCOCC4)cn3)c2C(N)=O)cc(C)c1O]<br>11 | B | C | D | C | B |
| 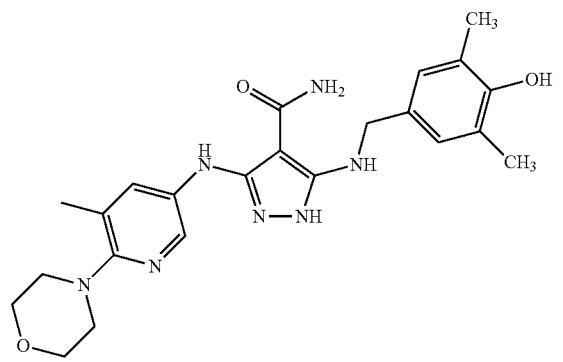 [SMILES: Cc1cc(Nc2n[nH]c(NCc3cc(C)c(O)c(C)c3)c2C(N)=O)cnc1N1CCOCC1]<br>12 | C | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
| --- | --- | --- | --- | --- | --- |
| 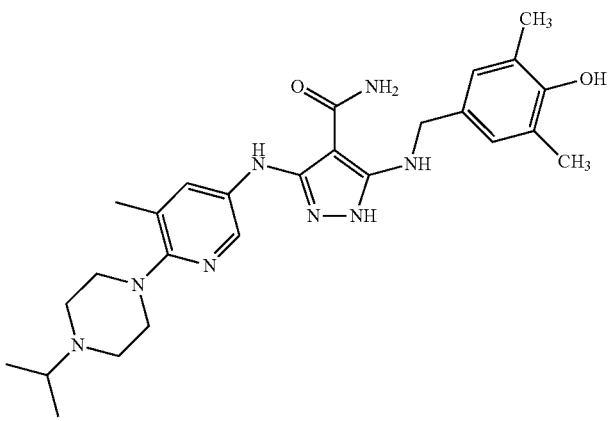 [SMILES: Cc1cc(Nc2n[nH]c(NCc3cc(C)c(O)c(C)c3)c2C(N)=O)cnc1N1CCN(C(C)C)CC1]<br>13 | D | D | D | B | B |
| 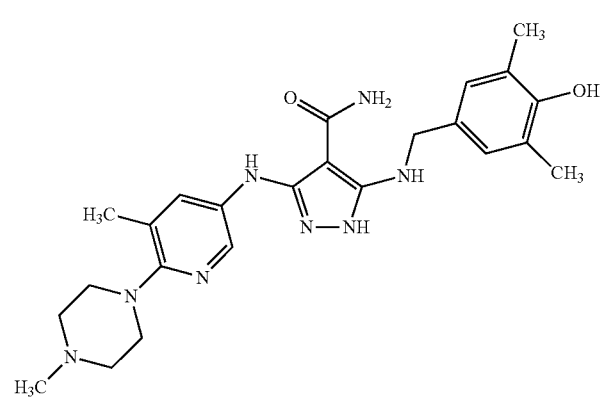 [SMILES: Cc1cc(Nc2n[nH]c(NCc3cc(C)c(O)c(C)c3)c2C(N)=O)cnc1N1CCN(C)CC1]<br>14 | D | D | D | C | B |
| 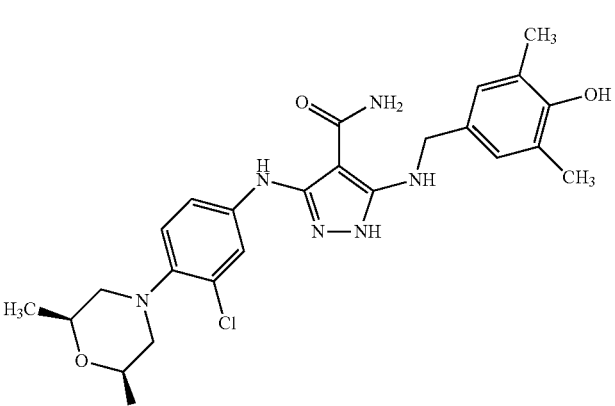<br>15 | B | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 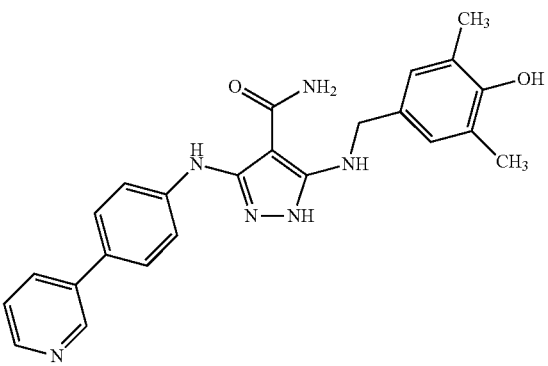 [SMILES: Cc1cc(CNc2[nH]nc(Nc3ccc(-c4cccnc4)cc3)c2C(N)=O)cc(C)c1O]<br>16 | B | D | D | B | B |
| 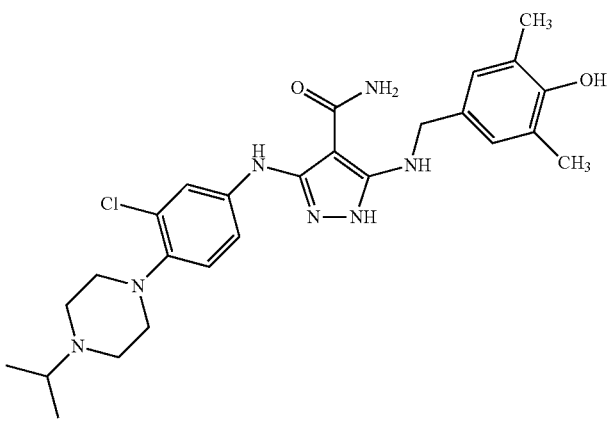 [SMILES: Cc1cc(CNc2[nH]nc(Nc3ccc(N4CCN(C(C)C)CC4)c(Cl)c3)c2C(N)=O)cc(C)c1O]<br>17 | A | C | C | A | A |
| 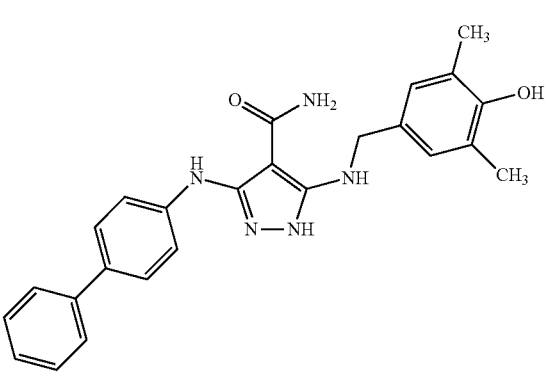 [SMILES: Cc1cc(CNc2[nH]nc(Nc3ccc(-c4ccccc4)cc3)c2C(N)=O)cc(C)c1O]<br>18 | D | D | D | C | C |

TABLE 2-continued
| Compound | RCK Activity Level | JAK2 Activity Level | JAK3 Activity Level | RCK:JAK2 selectivity ratio | RCK:JAK3 selectivity ratio |
|---|---|---|---|---|---|
| 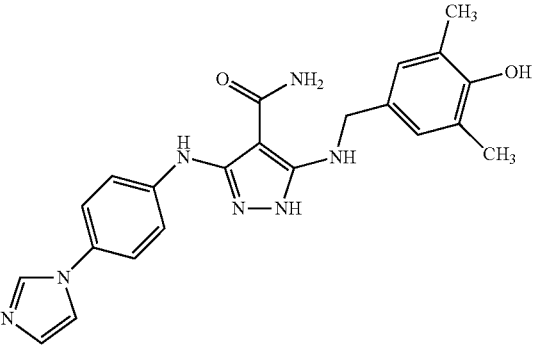 [SMILES: Cc1cc(CNc2[nH]nc(Nc3ccc(-n4ccnc4)cc3)c2C(N)=O)cc(C)c1O] 19 | C | D | D | A | A |
| 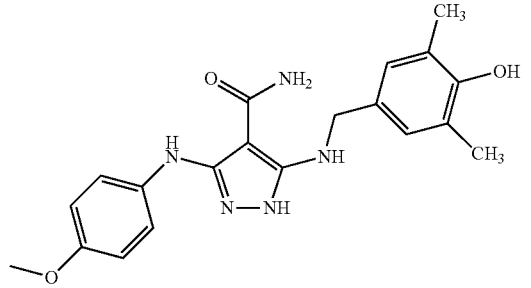 [SMILES: COc1ccc(Nc2n[nH]c(NCc3cc(C)c(O)c(C)c3)c2C(N)=O)cc1] 20 | C | D | D | C | B |
| 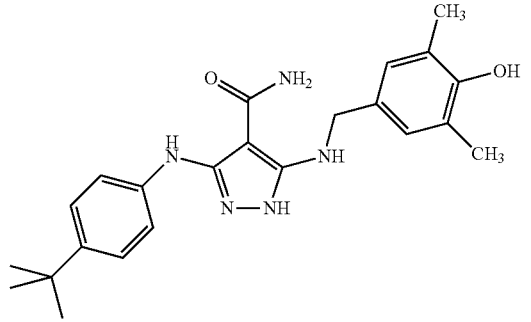 [SMILES: Cc1cc(CNc2[nH]nc(Nc3ccc(C(C)(C)C)cc3)c2C(N)=O)cc(C)c1O] 21 | D | D | D | C | — |
| 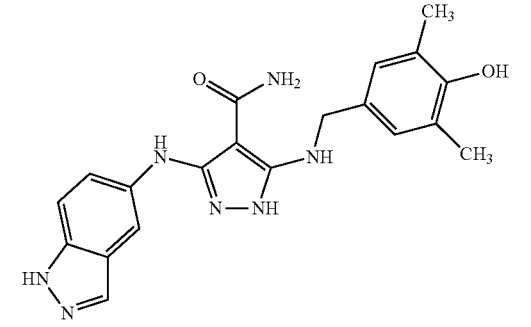 [SMILES: Cc1cc(CNc2[nH]nc(Nc3ccc4[nH]ncc4c3)c2C(N)=O)cc(C)c1O] 22 | C | D | D | C | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 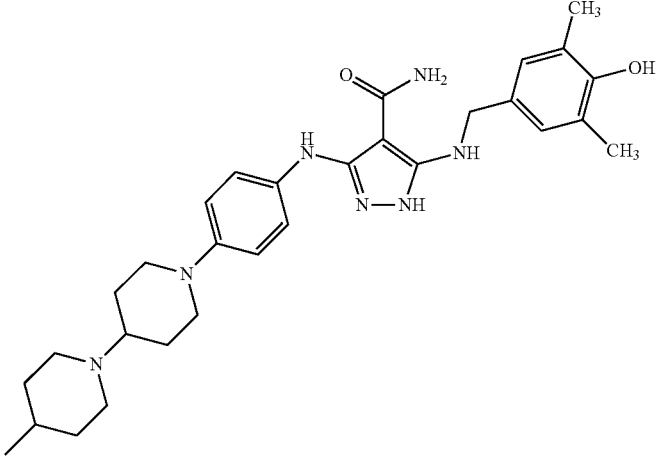 [SMILES: Cc1cc(CNc2[nH]nc(Nc3ccc(N4CCC(N5CCC(C)CC5)CC4)cc3)c2C(N)=O)cc(C)c1O]<br>23 | A | D | D | B | B |
| 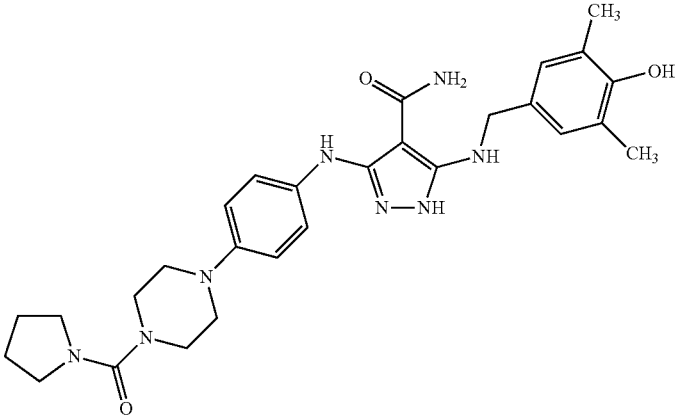 [SMILES: Cc1cc(CNc2[nH]nc(Nc3ccc(N4CCN(C(=O)N5CCCC5)CC4)cc3)c2C(N)=O)cc(C)c1O]<br>24 | A | D | D | B | A |
| 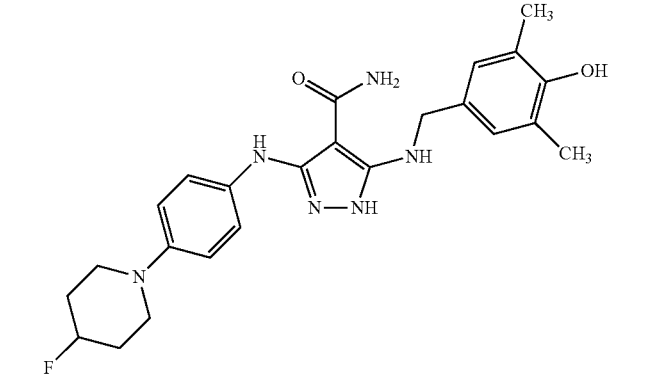 [SMILES: Cc1cc(CNc2[nH]nc(Nc3ccc(N4CCC(F)CC4)cc3)c2C(N)=O)cc(C)c1O]<br>25 | C | D | D | C | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 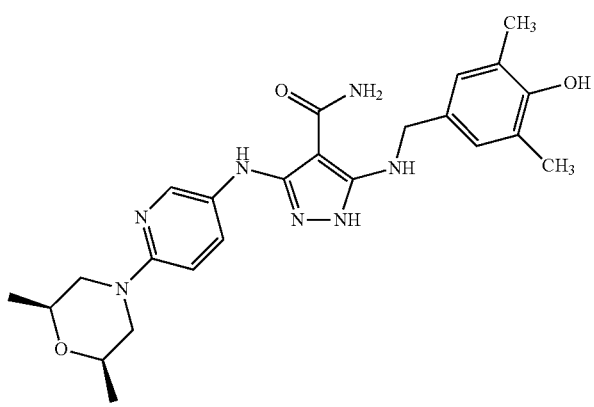 [SMILES: Cc1cc(CNc2[nH]nc(Nc3ccc(N4C[C@@H](C)O[C@@H](C)C4)nc3)c2C(N)=O)cc(C)c1O]<br>26 | C | D | D | B | B |
| 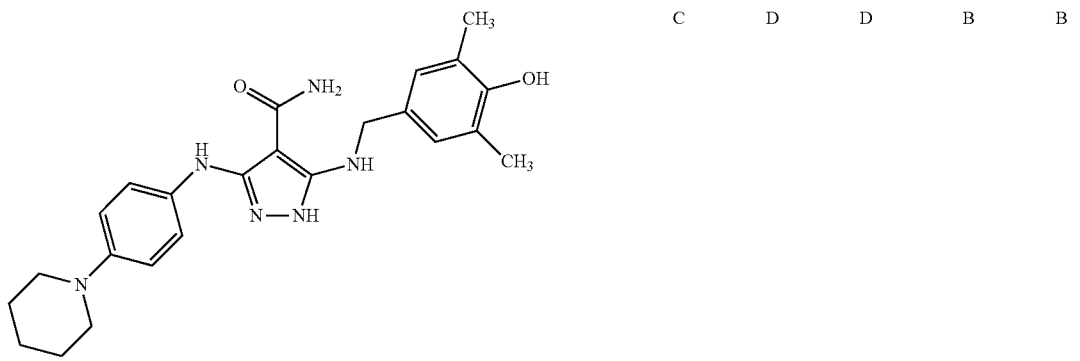<br>27 | C | D | D | B | B |
| 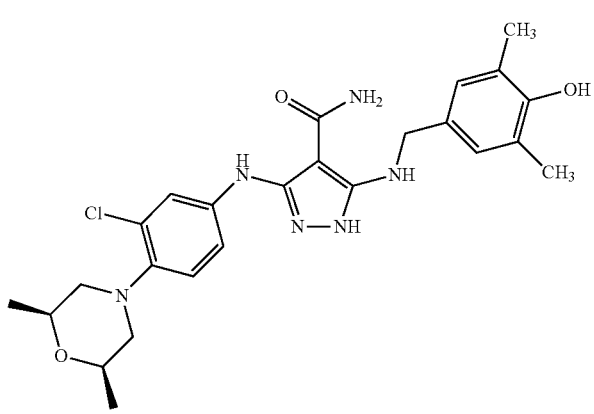 [SMILES: Cc1cc(CNc2[nH]nc(Nc3ccc(N4C[C@@H](C)O[C@@H](C)C4)c(Cl)c3)c2C(N)=O)cc(C)c1O]<br>28 | B | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 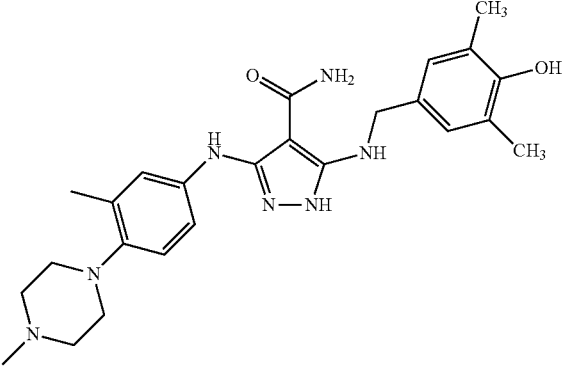 [SMILES: Cc1cc(Nc2n[nH]c(NCc3cc(C)c(O)c(C)c3)c2C(N)=O)ccc1N1CCN(C)CC1] 29 | A | C | D | B | B |
| 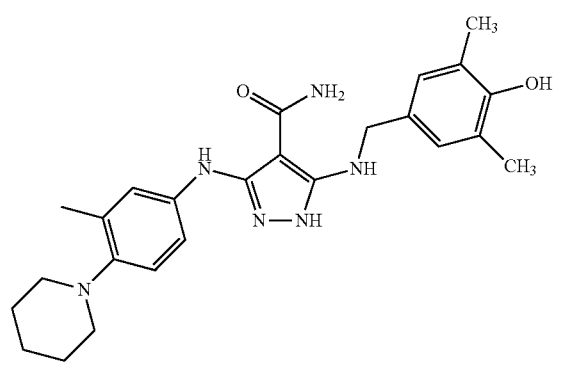 [SMILES: Cc1cc(Nc2n[nH]c(NCc3cc(C)c(O)c(C)c3)c2C(N)=O)ccc1N1CCCCC1] 30 | B | D | D | B | B |
| 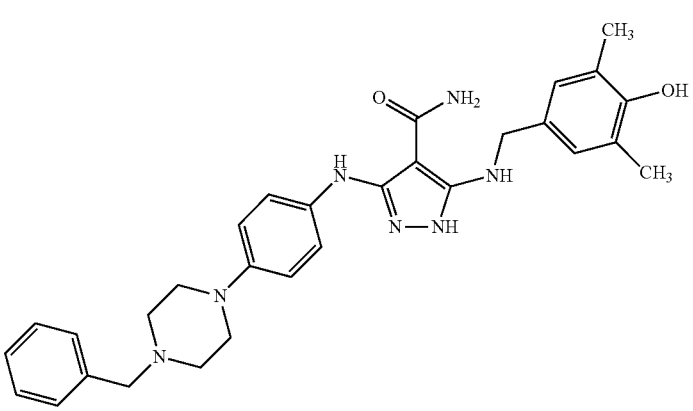 [SMILES: Cc1cc(CNc2[nH]nc(Nc3ccc(N4CCN(Cc5ccccc5)CC4)cc3)c2C(N)=O)cc(C)c1O] 31 | A | D | D | B | B |

TABLE 2-continued

| Compound | RCK Activity Level | JAK2 Activity Level | JAK3 Activity Level | RCK:JAK2 selectivity ratio | RCK:JAK3 selectivity ratio |
|---|---|---|---|---|---|
| 32 | A | C | C | C | B |
| 33 | B | C | D | C | B |
| 34 | B | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 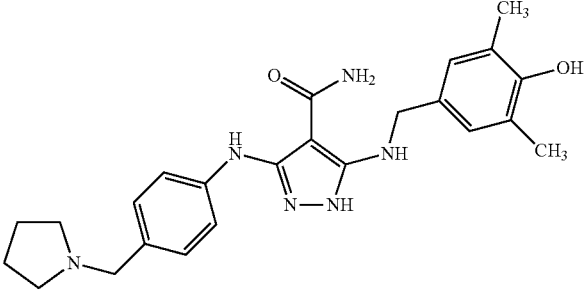 [SMILES: Cc1cc(CNc2[nH]nc(Nc3ccc(CN4CCCC4)cc3)c2C(N)=O)cc(C)c1O]<br>35 | B | C | D | C | B |
| 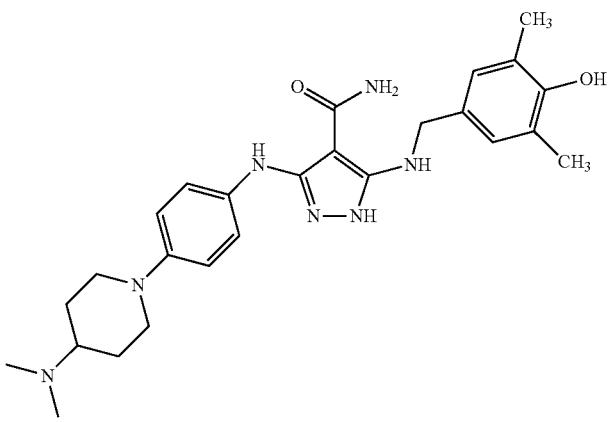 [SMILES: Cc1cc(CNc2[nH]nc(Nc3ccc(N4CCC(N(C)C)CC4)cc3)c2C(N)=O)cc(C)c1O]<br>36 | A | C | D | B | A |
| 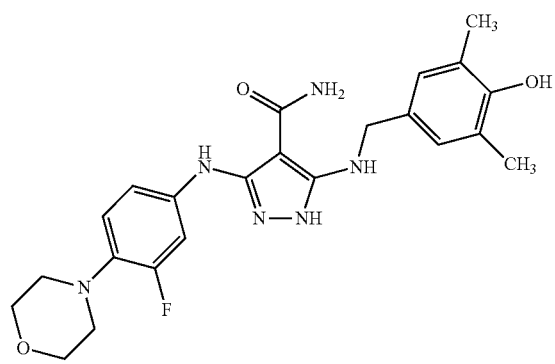 [SMILES: Cc1cc(CNc2[nH]nc(Nc3ccc(N4CCOCC4)c(F)c3)c2C(N)=O)cc(C)c1O]<br>37 | A | D | D | B | A |

TABLE 2-continued
| Compound | RCK Activity Level | JAK2 Activity Level | JAK3 Activity Level | RCK:JAK2 selectivity ratio | RCK:JAK3 selectivity ratio |
|---|---|---|---|---|---|
| 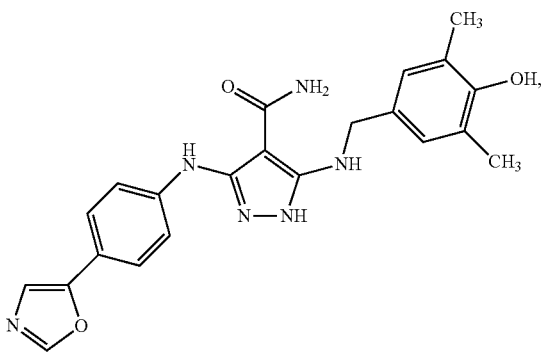 [SMILES: Cc1cc(CNc2[nH]nc(Nc3ccc(-c4cnco4)cc3)c2C(N)=O)cc(C)c1O]<br>38 | C | D | D | A | A |
| 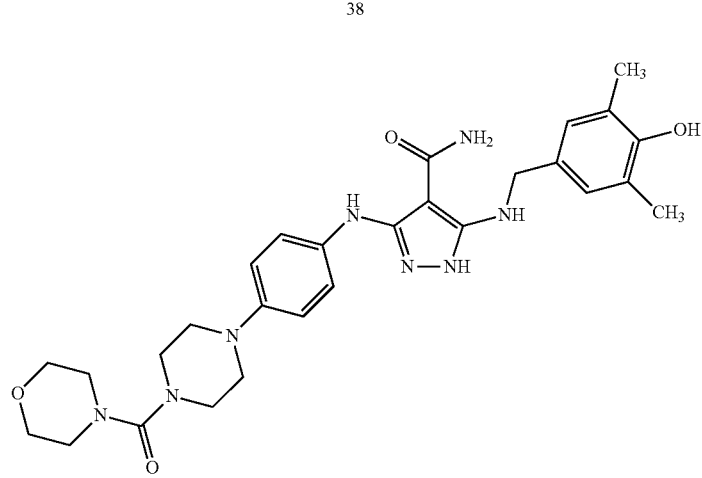<br>39 | B | A | A | B | B |
| 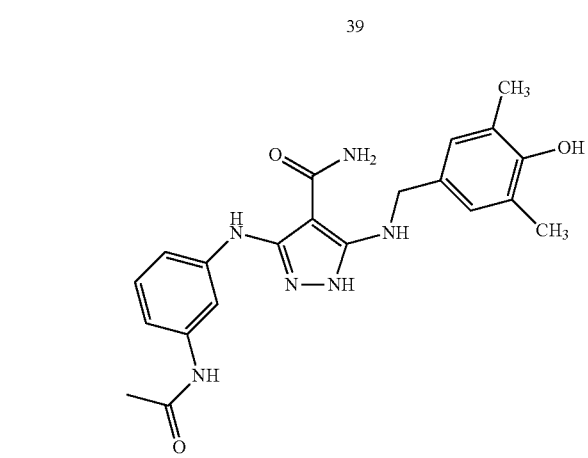<br>40 | D | D | D | C | C |

TABLE 2-continued

| Compound | RCK Activity Level | JAK2 Activity Level | JAK3 Activity Level | RCK:JAK2 selectivity ratio | RCK:JAK3 selectivity ratio |
| --- | --- | --- | --- | --- | --- |
| 41 | A | C | D | B | A |
| 42 | D | D | D | B | B |
| 43 | D | D | D | D | C |
| 44 | C | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 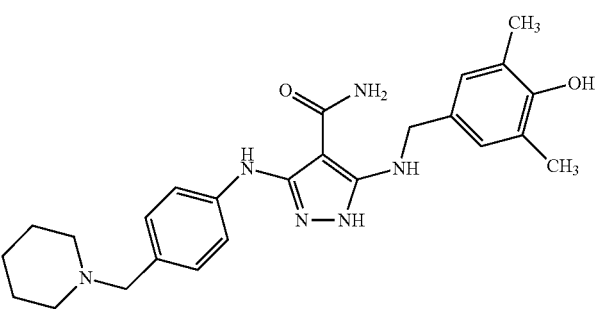 [SMILES: Cc1cc(CNc2[nH]nc(Nc3ccc(CN4CCCCC4)cc3)c2C(N)=O)cc(C)c1O] 45 | A | C | C | C | B |
| 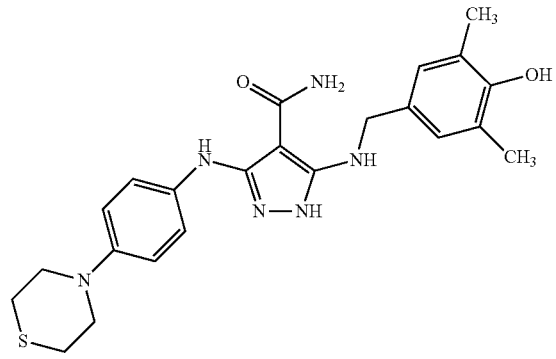 [SMILES: Cc1cc(CNc2[nH]nc(Nc3ccc(N4CCSCC4)cc3)c2C(N)=O)cc(C)c1O] 46 | A | C | D | B | B |
| 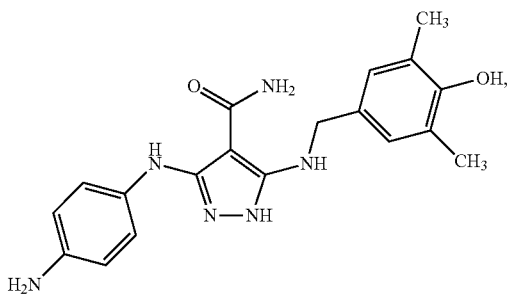 [SMILES: Cc1cc(CNc2[nH]nc(Nc3ccc(N)cc3)c2C(N)=O)cc(C)c1O] 47 | D | D | D | C | C |
| 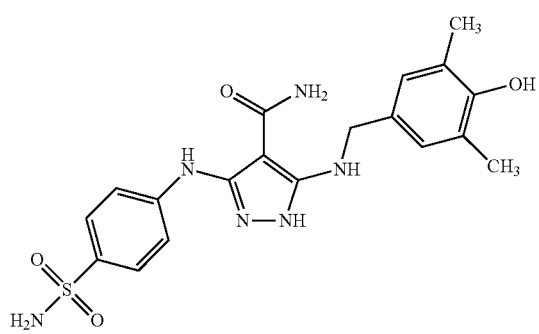 [SMILES: Cc1cc(CNc2[nH]nc(Nc3ccc(S(N)(=O)=O)cc3)c2C(N)=O)cc(C)c1O] 48 | C | C | D | C | B |

TABLE 2-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| 49 | A | C | C | A | A |
| 50 | C | D | D | C | C |
| 51 | A | C | D | B | B |
| 52 | D | D | D | C | C |

TABLE 2-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| 53 | C | D | D | A | A |
| 54 | C | D | D | B | B |
| 55 | C | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 56 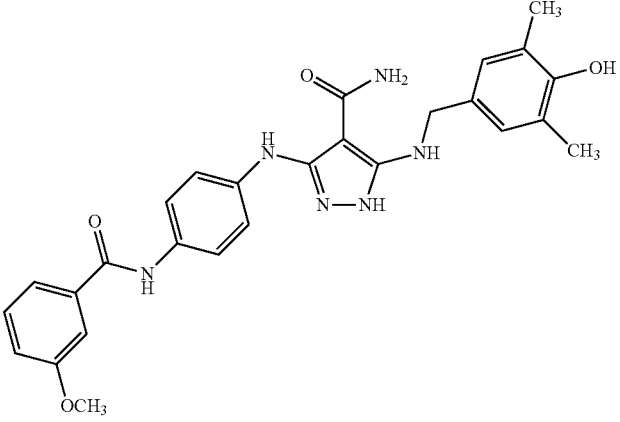 [SMILES: COc1cccc(C(=O)Nc2ccc(Nc3n[nH]c(NCc4cc(C)c(O)c(C)c4)c3C(N)=O)cc2)c1] | C | D | D | B | A |
| 57 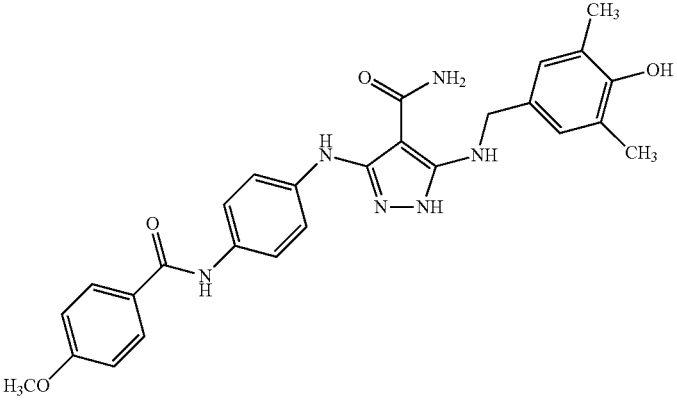 [SMILES: COc1ccc(C(=O)Nc2ccc(Nc3n[nH]c(NCc4cc(C)c(O)c(C)c4)c3C(N)=O)cc2)cc1] | B | D | D | A | A |
| 58 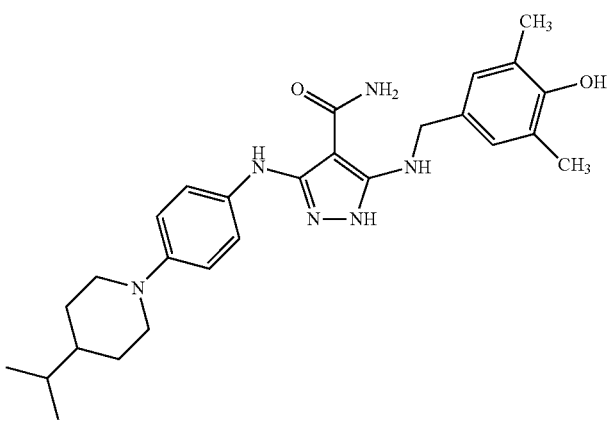 [SMILES: Cc1cc(CNc2[nH]nc(Nc3ccc(N4CCC(C(C)C)CC4)cc3)c2C(N)=O)cc(C)c1O] | C | D | D | B | B |

TABLE 2-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 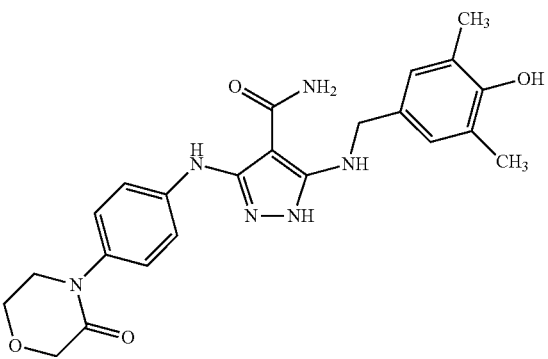 [SMILES: Cc1cc(CNc2[nH]nc(Nc3ccc(N4CCOCC4=O)cc3)c2C(N)=O)cc(C)c1O]<br>59 | C | D | D | B | B |
| 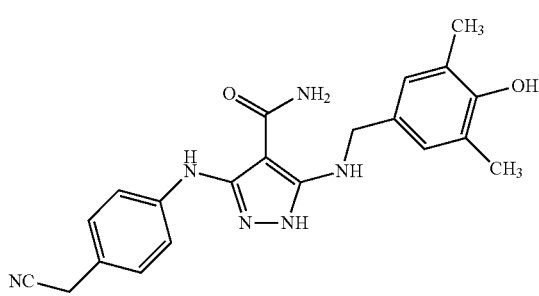 [SMILES: Cc1cc(CNc2[nH]nc(Nc3ccc(CC#N)cc3)c2C(N)=O)cc(C)c1O]<br>61 | D | D | D | C | C |
| 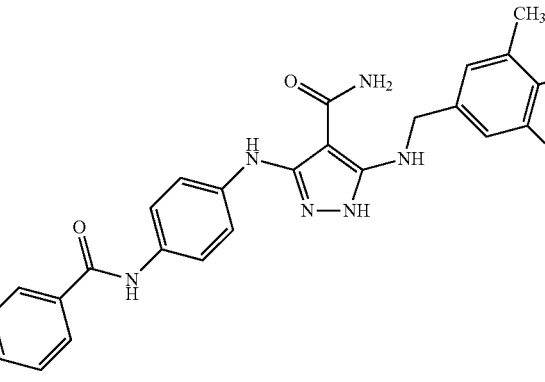<br>62 | C | D | D | B | B |

TABLE 2-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | C | D | D | B | B |
| 63 (structure) | D | D | D | C | C |

TABLE 3

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | A | A | B | C | B |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (3-chloro-4-morpholinophenyl)amino / (4-hydroxybenzyl)amino pyrazole carboxamide | A | A | A | D | C |
| (4-morpholinophenyl)amino / (4-hydroxybenzyl)amino pyrazole carboxamide | A | A | A | D | C |
| (4-((2S,6R)-2,6-dimethylmorpholino)phenyl)amino / (4-hydroxybenzyl)amino pyrazole carboxamide | A | A | A | D | C |
| (5-chloro-6-morpholinopyridin-3-yl)amino / (4-hydroxybenzyl)amino pyrazole carboxamide | A | A | B | C | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | A | A | A | D | C |
| (structure) | A | A | A | D | C |
| (structure) | A | N/A | N/A | N/A | N/A |
| (structure) | A | A | A | D | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| *(structure: 3-[(4-(4-methylpiperazin-1-yl)phenyl)amino]-5-[(4-hydroxybenzyl)amino]-1H-pyrazole-4-carboxamide)* | A | A | A | C | C |
| *(structure: 3-[(5-morpholinopyridin-2-yl)amino]-5-[(4-hydroxybenzyl)amino]-1H-pyrazole-4-carboxamide)* | A | A | A | D | D |
| *(structure: 3-[(5-methyl-6-morpholinopyridin-3-yl)amino]-5-[(4-hydroxybenzyl)amino]-1H-pyrazole-4-carboxamide)* | A | A | A | D | C |
| *(structure: 3-[(5-methyl-6-(4-isopropylpiperazin-1-yl)pyridin-3-yl)amino]-5-[(4-hydroxybenzyl)amino]-1H-pyrazole-4-carboxamide)* | A | A | A | D | C |

TABLE 3-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 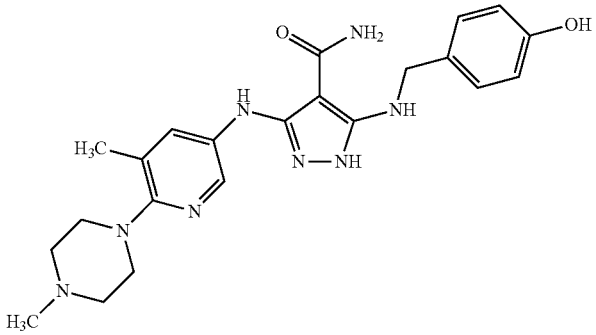 [SMILES: Cc1cc(Nc2n[nH]c(NCc3ccc(O)cc3)c2C(N)=O)cnc1N1CCN(C)CC1] | A | A | A | D | C |
| 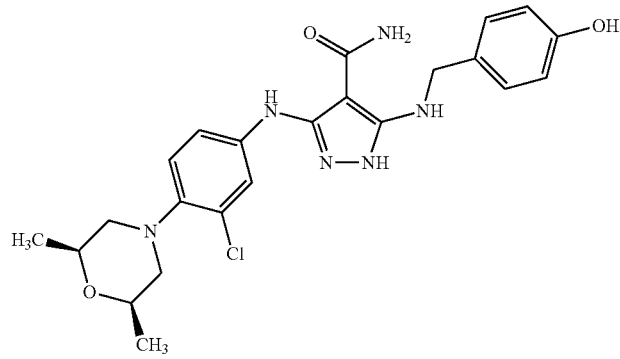 [SMILES: C[C@@H]1CN(c2ccc(Nc3n[nH]c(NCc4ccc(O)cc4)c3C(N)=O)cc2Cl)C[C@H](C)O1] | A | A | A | D | C |
| 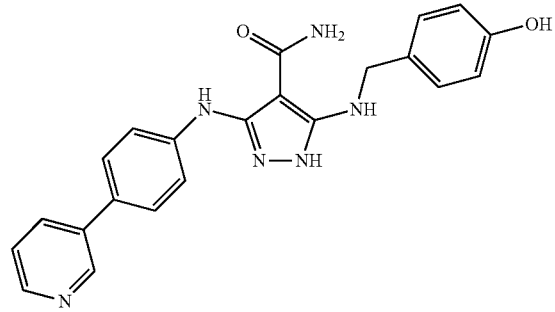 [SMILES: NC(=O)c1c(Nc2ccc(-c3cccnc3)cc2)n[nH]c1NCc1ccc(O)cc1] | A | A | A | C | C |
| 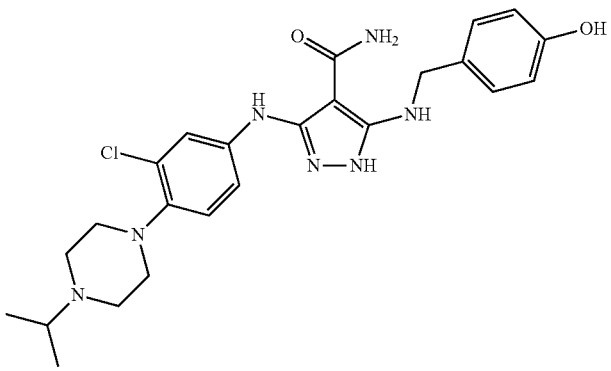 [SMILES: CC(C)N1CCN(c2ccc(Nc3n[nH]c(NCc4ccc(O)cc4)c3C(N)=O)cc2Cl)CC1] | A | A | A | C | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | B | A | B | D | C |
| (structure) | A | A | A | D | C |
| (structure) | A | A | A | D | C |
| (structure) | A | A | B | D | C |
| (structure) | B | A | A | D | D |

TABLE 3-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 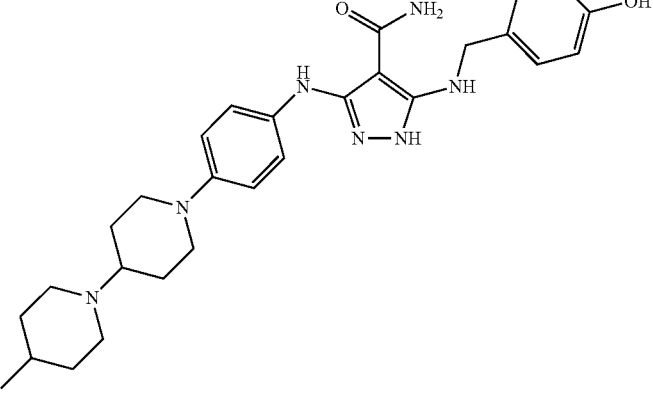 | A | A | A | C | D |
| 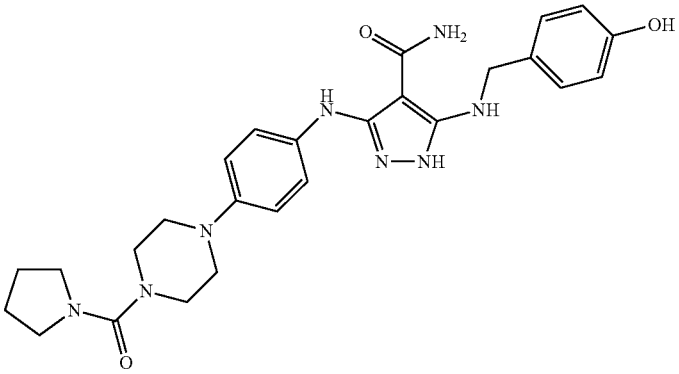 [SMILES: NC(=O)c1c(Nc2ccc(N3CCN(C(=O)N4CCCC4)CC3)cc2)n[nH]c1NCc1ccc(O)cc1] | A | A | A | D | C |
| 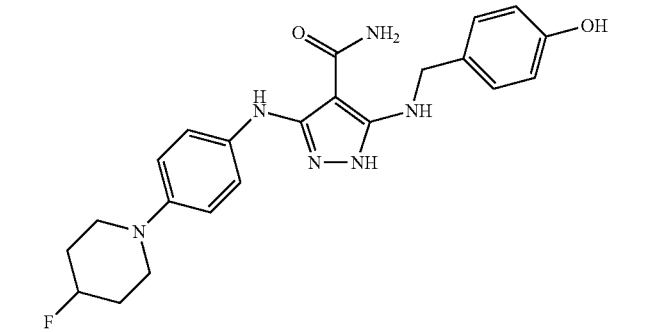 [SMILES: NC(=O)c1c(Nc2ccc(N3CCC(F)CC3)cc2)n[nH]c1NCc1ccc(O)cc1] | A | A | A | D | D |
| 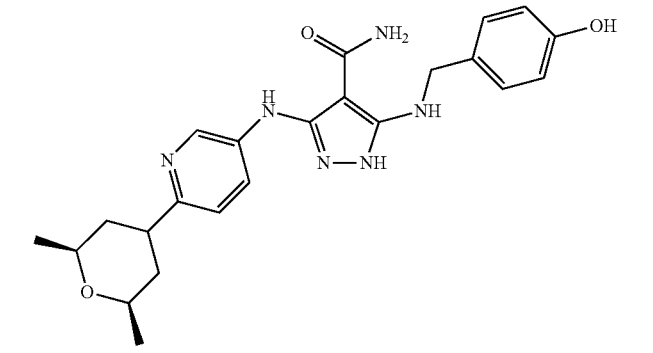 [SMILES: C[C@@H]1CC(c2ccc(Nc3n[nH]c(NCc4ccc(O)cc4)c3C(N)=O)cn2)C[C@H](C)O1] | A | A | A | C | C |

TABLE 3-continued
| Compound | RCK Activity Level | JAK2 Activity Level | JAK3 Activity Level | RCK: JAK2 selectivity ratio | RCK: JAK3 selectivity ratio |
|---|---|---|---|---|---|
| 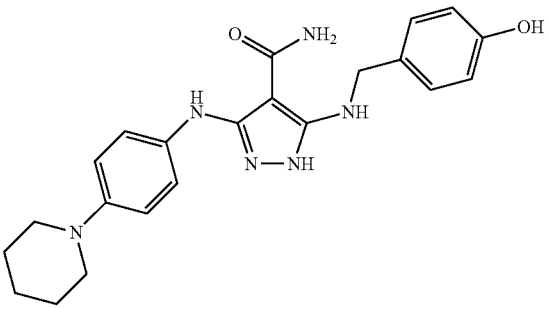 [SMILES: NC(=O)c1c(Nc2ccc(N3CCCCC3)cc2)n[nH]c1NCc1ccc(O)cc1] | A | A | A | C | C |
| 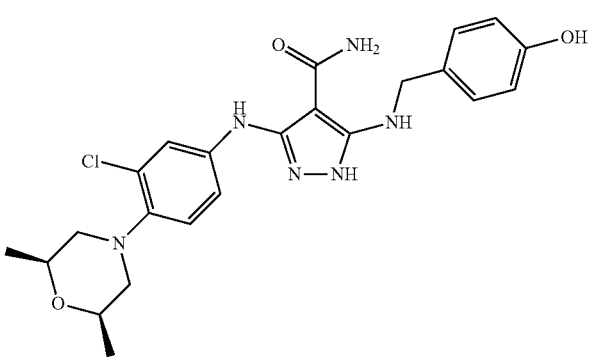 [SMILES: C[C@@H]1CN(c2ccc(Nc3n[nH]c(NCc4ccc(O)cc4)c3C(N)=O)cc2Cl)C[C@H](C)O1] | A | A | A | D | C |
| 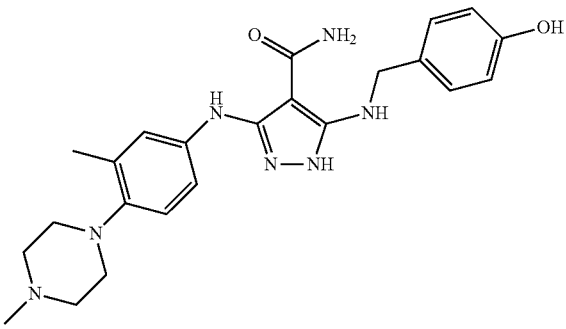 [SMILES: Cc1cc(Nc2n[nH]c(NCc3ccc(O)cc3)c2C(N)=O)ccc1N1CCN(C)CC1] | A | A | A | C | C |
| 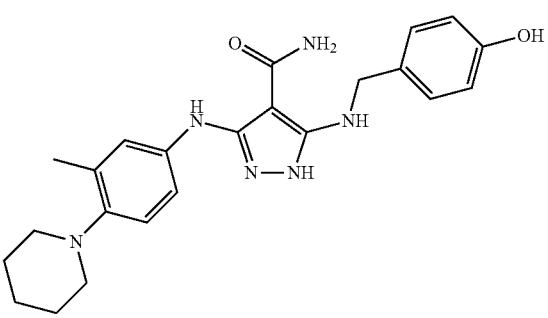 [SMILES: Cc1cc(Nc2n[nH]c(NCc3ccc(O)cc3)c2C(N)=O)ccc1N1CCCCC1] | A | A | B | C | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| *(structure: 3-[4-(4-benzylpiperazin-1-yl)phenylamino]-5-[(4-hydroxybenzyl)amino]-1H-pyrazole-4-carboxamide)* | A | A | A | D | C |
| *(structure: 3-[4-(1,1-dioxo-thiomorpholin-4-yl)phenylamino]-5-[(4-hydroxybenzyl)amino]-1H-pyrazole-4-carboxamide)* | A | A | A | D | D |
| *(structure: 3-[(5-piperidin-1-yl-pyridin-2-yl)amino]-5-[(4-hydroxybenzyl)amino]-1H-pyrazole-4-carboxamide)* | A | A | A | D | D |
| *(structure: 3-[4-(4-chloropiperidin-1-yl)phenylamino]-5-[(4-hydroxybenzyl)amino]-1H-pyrazole-4-carboxamide)* | A | A | A | D | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure with pyrrolidinylmethyl-phenylamino pyrazole carboxamide and hydroxybenzyl) | A | A | A | D | D |
| (structure with 4-(dimethylamino)piperidinyl-phenylamino pyrazole carboxamide and hydroxybenzyl) | A | A | A | D | D |
| (structure with morpholino-fluorophenylamino pyrazole carboxamide and hydroxybenzyl) | A | A | A | — | — |
| (structure with oxazolyl-phenylamino pyrazole carboxamide and hydroxybenzyl) | A | A | A | C | C |

TABLE 3-continued

| Compound | RCK Activity Level | JAK2 Activity Level | JAK3 Activity Level | RCK: JAK2 selectivity ratio | RCK: JAK3 selectivity ratio |
| --- | --- | --- | --- | --- | --- |
| (structure: pyrazole carboxamide with 4-hydroxybenzylamino and phenyl-piperazine-morpholine carbonyl substituent) | A | A | A | D | C |
| (structure: pyrazole carboxamide with 4-hydroxybenzylamino and 3-acetamidophenylamino substituent) | A | A | A | D | D |
| (structure: pyrazole carboxamide with 4-hydroxybenzylamino and 3-chloro-4-(4-methylpiperazin-1-yl)phenylamino substituent) | A | A | A | D | C |
| (structure: pyrazole carboxamide with 4-hydroxybenzylamino and 4-fluorophenylamino substituent) | A | A | A | D | D |
| (structure: pyrazole carboxamide with 4-hydroxybenzylamino and 3-cyanophenylamino substituent) | B | A | A | D | D |

TABLE 3-continued

| Compound | RCK Activity Level | JAK2 Activity Level | JAK3 Activity Level | RCK:JAK2 selectivity ratio | RCK:JAK3 selectivity ratio |
|---|---|---|---|---|---|
| (pyrimidinyl-piperazinyl-phenyl-NH / pyrazole-CONH2 / NH-CH2-phenyl-OH) | A | A | A | C | C |
| (piperidinyl-methyl-phenyl-NH / pyrazole-CONH2 / NH-CH2-phenyl-OH) | A | A | A | D | D |
| (thiomorpholinyl-phenyl-NH / pyrazole-CONH2 / NH-CH2-phenyl-OH) | A | A | A | D | C |
| (aminophenyl-NH / pyrazole-CONH2 / NH-CH2-phenyl-OH) | C | B | C | D | D |
| (sulfamoylphenyl-NH / pyrazole-CONH2 / NH-CH2-phenyl-OH) | A | A | A | D | D |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (pyrrolidinyl-piperidinyl-pyridinyl-NH-pyrazole-carboxamide with 4-hydroxybenzyl-NH) | A | A | A | D | C |
| (4-dimethylaminophenyl-NH-pyrazole-carboxamide with 4-hydroxybenzyl-NH) | C | A | C | D | C |
| (4-(morpholinomethyl)phenyl-NH-pyrazole-carboxamide with 4-hydroxybenzyl-NH) | A | A | A | D | D |
| (3-methoxyphenyl-NH-pyrazole-carboxamide with 4-hydroxybenzyl-NH) | A | A | A | D | D |
| (4-(4-fluorobenzamido)phenyl-NH-pyrazole-carboxamide with 4-hydroxybenzyl-NH) | A | A | A | C | C |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | A | A | A | D | C |
| (structure) | A | A | A | B | B |
| (structure) | A | A | A | C | B |
| (structure) | A | A | A | B | B |

TABLE 3-continued

| Compound | RCK Activity Level | JAK2 Activity Level | JAK3 Activity Level | RCK: JAK2 selectivity ratio | RCK: JAK3 selectivity ratio |
|---|---|---|---|---|---|
| (structure) | B | C | C | C | C |
| (structure) | A | A | A | D | C |
| (structure) | A | A | A | D | C |
| (structure) | B | C | C | C | C |

TABLE 3-continued

| Compound | RCK Activity Level | JAK2 Activity Level | JAK3 Activity Level | RCK:JAK2 selectivity ratio | RCK:JAK3 selectivity ratio |
|---|---|---|---|---|---|
| 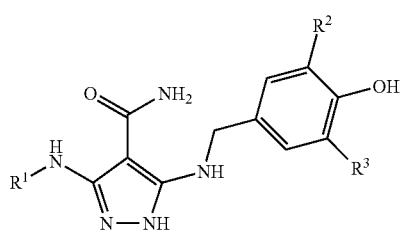 | A | A | B | D | C |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for treating or ameliorating one or more symptoms of an RC-kinase-mediated disorder, disease, or condition in a subject, which comprises administering to the subject a compound of Formula I:

(I)

or a stereoisomer, enantiomer, mixture of enantiomers, or mixture of diastereomers; or a pharmaceutically acceptable salt thereof; wherein:
  $R^1$ is $C_{6-14}$ aryl, heteroaryl, or heterocyclyl;
  $R^2$ and $R^3$ are each independently $C_{1-6}$ alkyl or $C_{3-10}$ cycloalkyl;
  wherein each alkyl, cycloalkyl, aryl, heteroaryl or heterocyclyl is optionally substituted with one or more substituents q, where each q is independently selected from halo, $c_{1-6}$ alkyl, heteroaryl, and heterocyclyl, each of which is further optionally substituted with one or more $c_{1-6}$ alkyl;
with the proviso that the compound is not 3-((3-chlorophenyl)amino)-5-((4-hydroxy-3,5-dimethylbenzyl)amino)-1h-pyrazole-4-carboxamide wherein the disorder, disease, or condition is asthma, exercise induced asthma, allergic rhinitis, atopic dermatitis, chronic obstructive pulmonary disease, allergic conjunctivitis, or fibrosis.

2. The method of claim 1, wherein $R^1$ is $C_{6-14}$ aryl or heteroaryl, each of which is optionally substituted with one or more substituents Q.

3. The method of claim 1, wherein $R^1$ is $C_{6-14}$ aryl, optionally substituted with one or more substituents Q.

4. The method of claim 1, wherein $R^1$ is phenyl, optionally substituted with one or more substituents Q.

5. The method of claim 4, wherein Q is independently selected from fluoro, chloro, bromo, iodo, methyl, morpholinyl, dimethylmorpholinyl, pyrrolyl, isopropylpiperazinyl, methylpiperazinyl, pyridinyl, and benzylpiperazinyl.

6. The method of claim 3, wherein $R^1$ is 3-methyl-4-morpholinophenyl, 3-chloro-4-morpholinophenyl, 4-morpholinophenyl, 4-(2,6-dimethylmorpholino)phenyl, 4-(1H-pyrrol-1-yl)phenyl, 4-(4-isopropylpiperazin-1-yl)phenyl, 4-(pyridin-2-yl)phenyl, 4-(4-methylpiperazin-1-yl)phenyl, 3-chloro-4-(2,6-dimethylmorpholino)phenyl, 4-(pyridin-3-yl)phenyl, or 3-chloro-4-(4-isopropylpiperazin-1-yl)phenyl.

7. The method of claim 1, wherein $R^1$ is heteroaryl, optionally substituted with one or more substituents Q.

8. The method of claim 7, wherein $R^1$ is 5- or 6-membered heteroaryl, each of which is optionally substituted with one or more substituents Q.

9. The method of claim 8, wherein $R^1$ is pyridinyl, optionally substituted with one or more substituents Q.

10. The method of claim 9, wherein $R^1$ is 2-morpholino-3-chloropyridin-5-yl, 2-morpholinopyridin-5-yl, 5-morpholinopyridin-2-yl, 2-morpholino-3-methylpyridin-5-yl, 2-(4-isopropylpiperazin-1-yl)-3-methylpyridin-5-yl, or 2-(4-methylpiperazin-1-yl)-3-methylpyridin-5-yl.

11. The method of claim 1, wherein $R^2$ is $C_{1-6}$ alkyl.

12. The method of claim 1, wherein $R^2$ is methyl.

13. The method of claim 1, wherein $R^3$ is $C_{1-6}$ alkyl.

14. The method of claim 1, wherein $R^3$ is methyl.

15. The method of claim 1, wherein the compound is selected from the group consisting of:
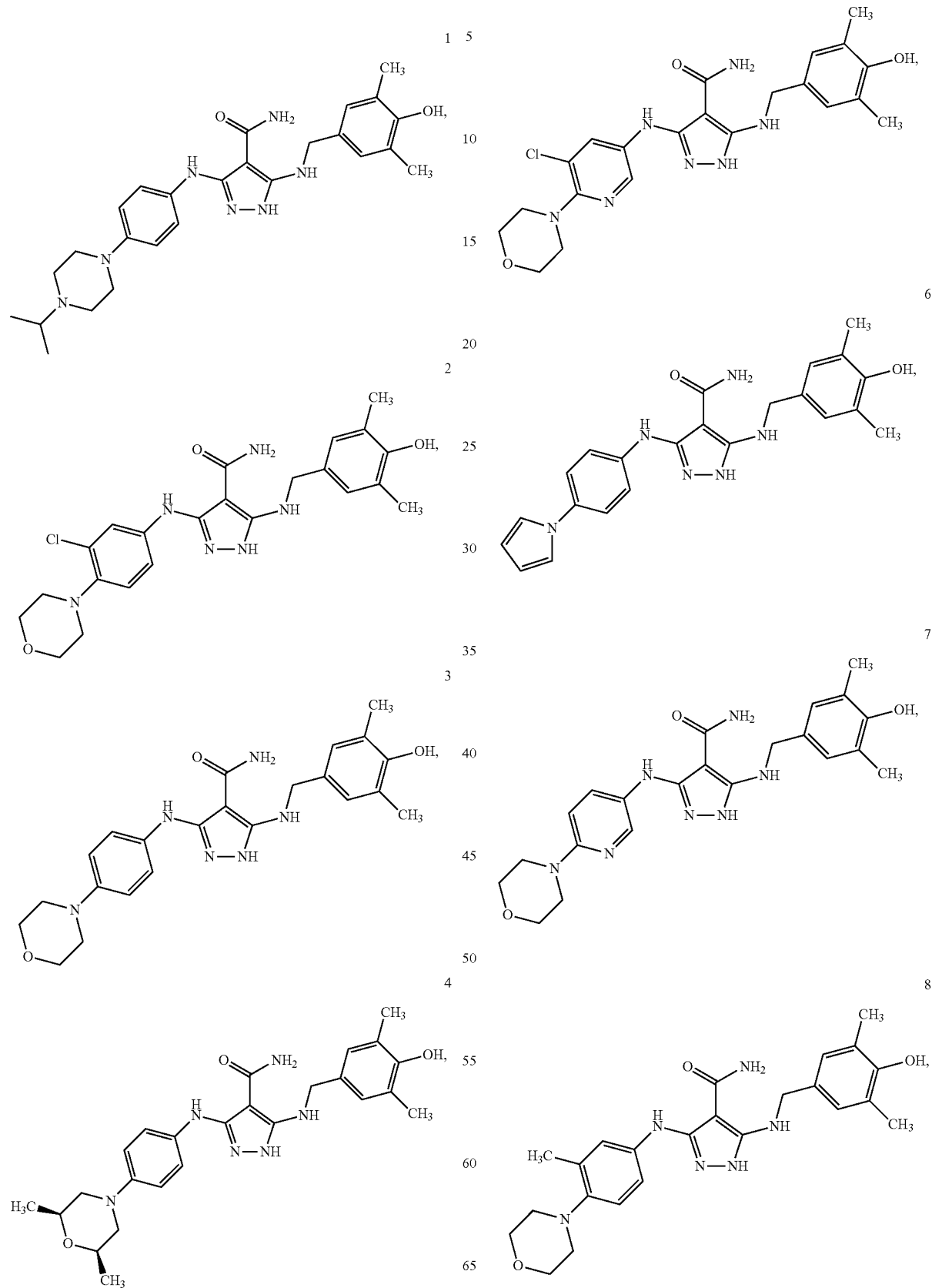

-continued
9
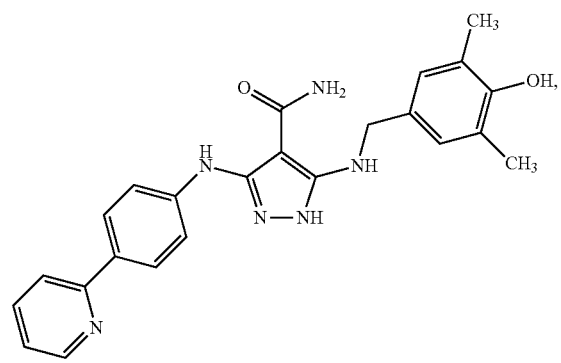
10
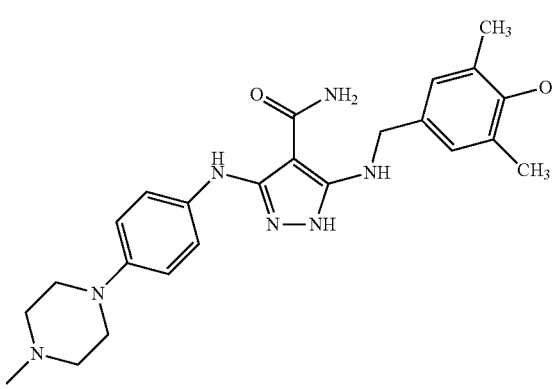
11
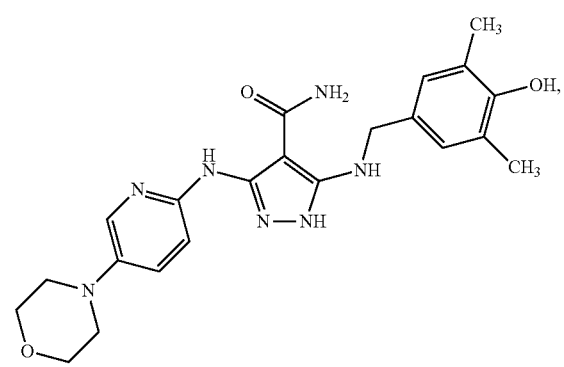
12
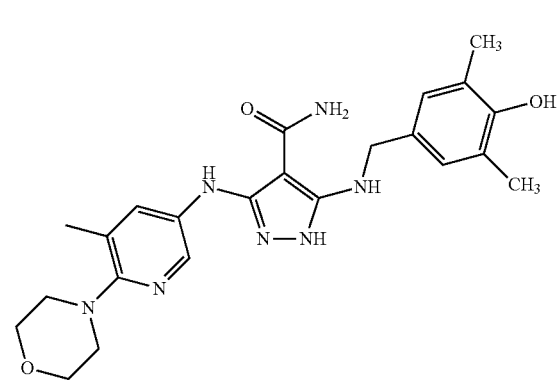
-continued
13
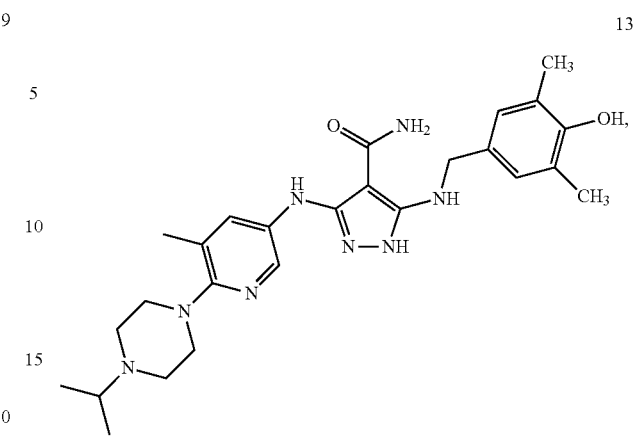
14
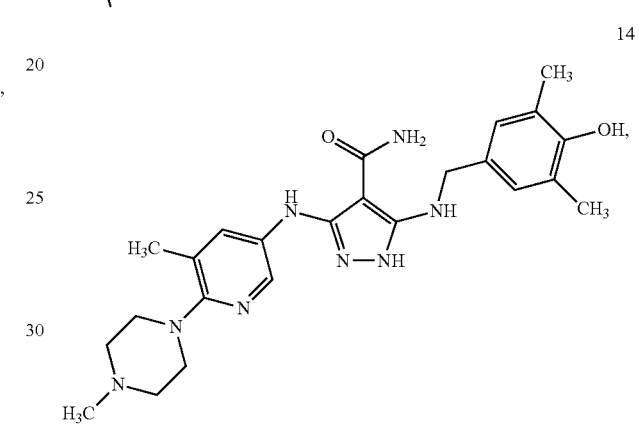
15
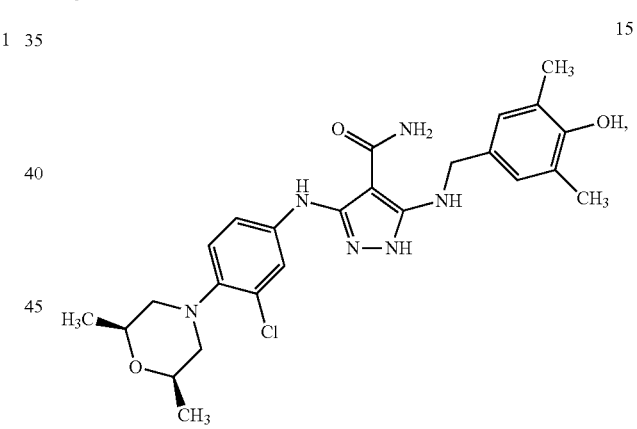
16
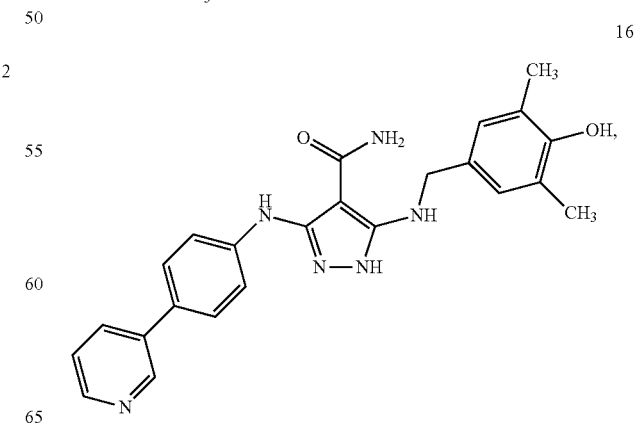

-continued

17

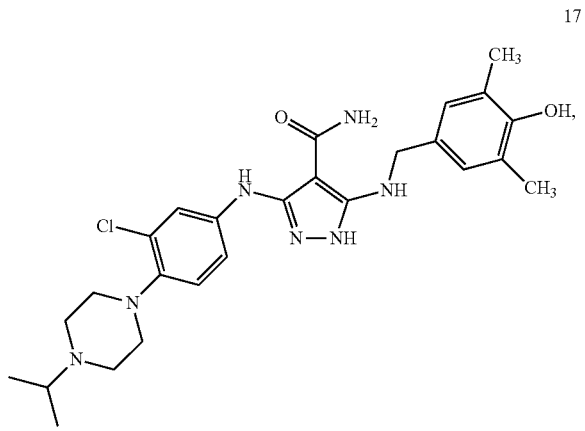

and stereoisomers, enantiomers, mixtures of enantiomers, and mixtures of diastereomers thereof; and pharmaceutically acceptable salts thereof.

16. The method of claim 1, wherein the compound is administered in combination with a second therapeutic agent.

17. A method for inhibiting RC kinase activity, comprising contacting a RC kinase with a compound of Formula I:

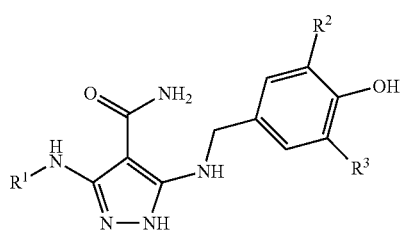

(I)

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents q, where each q is independently selected from halo, $c_{1-6}$ alkyl, heteroaryl, and heterocyclyl, each of which is further optionally substituted with one or more $c_{1-6}$ alkyl;

with the proviso that the compound is not 3-((3-chlorophenyl)amino)-5-((4-hydroxy-3,5-dimethylbenzyl)amino)-1H-pyrazole-4-carboxamide.

18. A method for treating or ameliorating one or more symptoms of an RC-kinase-mediated disorder, disease, or condition in a subject, which comprises administering to the subject a compound of Formula I:

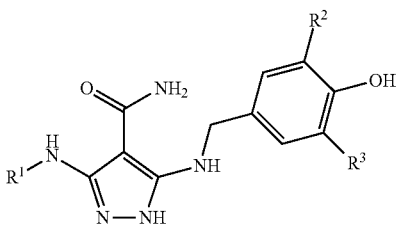

(I)

or a stereoisomer, enantiomer, mixture of enantiomers, or mixture of diastereomers; or a pharmaceutically acceptable salt thereof;
wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents q, where each q is independently selected from halo, $c_{1-6}$ alkyl, $c_{1-6}$ alkoxy, aryl, heteroaryl, and heterocyclyl, each of which is further optionally substituted with one or more $c_{1-6}$ alkyl, halo, aralkyl, dialkylamino, heterocyclyl, heterocyclylalkyl, and heterocyclylcarbonyl;

with the proviso that the compound is not 3-((3-chlorophenyl)amino)-5-((4-hydroxy-3,5-dimethylbenzyl) amino)-1 h-pyrazole-4-carboxamide wherein the disorder, disease, or condition is asthma, exercise induced asthma, allergic rhinitis, atopic dermatitis, chronic obstructive pulmonary disease, allergic conjunctivitis, or fibrosis.

19. The method of claim 18, wherein $R^1$ is $C_{6-14}$ aryl or heteroaryl, each of which is optionally substituted with one or more substituents Q.

20. The method of claim 18, wherein $R^1$ is $C_{6-14}$ aryl, optionally substituted with one or more substituents Q.

21. The method of claim 18, wherein $R^1$ is phenyl, optionally substituted with one or more substituents Q.

22. The method of claim 21, wherein Q is independently selected from fluoro, chloro, bromo, iodo, methyl, morpholinyl, dimethylmorpholinyl, pyrrolyl, isopropylpiperazinyl, methylpiperazinyl, pyridinyl, benzylpiperazinyl, phenyl, imidazolyl, methoxy, tert-butyl, indazolyl, methylpipiperidinyl, (pyrrolidinecarbonyl)piperazinyl, flouropiperidinyl, dimethylpyranyl, piperidinyl, benzyl, 1,1-dioxidothiomorpholino, pyrrolidinylmethyl, dimethylamino, oxazolyl, (piperidinecarbonyl)piperazinyl, acetamido, (pyrimidinyl)piperizinyl, piperidinylmethyl, thiomorpholinyl fluorophenylamido, methoxyphenylamido, isopropylpiperidinyl, cyanomethyl, (trifluoromethyl)phenylamido, and oxomorpholinyl.

23. The method of claim 20, wherein $R^1$ is 3-methyl-4-morpholinophenyl, 3-chloro-4-morpholinophenyl, 4-morpholinophenyl, 4-(2,6-dimethylmorpholino)phenyl, 4-(1H-pyrrol-1-yl)phenyl, 4-(4-isopropylpiperazin-1-yl)phenyl, 4-(pyridin-2-yl)phenyl, 4-(4-methylpiperazin-1-yl)phenyl, 3-chloro-4-(2,6-dimethylmorpholino)phenyl, 4-(pyridin-3-yl)phenyl, 3-chloro-4-(4-isopropylpiperazin-1-yl)phenyl, 1,1'-biphenyl, 4-(1H-imidazol-1-yl)phenyl, 4-methoxyphenyl, 4-tert-butylphenyl, 4-(4-methyl-[1,4'-bipiperidin]-1'-yl) phenyl, 4-(4-(morpholine-4-carbonyl)piperazin-1-yl)phenyl, 4-(4-fluoropiperidin-1-yl)phenyl, 4-(piperidin-1-yl) phenyl, 3-chloro-4-(2,6-dimethylmorpholino)phenyl, 3-methyl-4-(4-methylpiperazin-1-yl)phenyl, 3-methyl-4-

(piperidin-1-yl)phenyl, 4-(4-benzylpiperazin-1-yl)-3-methylphenyl, 4-(1,1-dioxidothiomorpholino)phenyl, (5-(piperidin-1-yl)pyridine-2-yl)phenyl, 4-(4-chloropiperidin-1-yl)phenyl, 4-(pyrrolidin-1-ylmethyl)phenyl, 4-(4-(dimethylamino)piperidin-1-yl)phenyl, 3-fluoro-4-morpholinophenyl, 4-(oxazol-5-yl)phenyl, 4-(4-(piperidine-1-carbonyl)piperazin-1-yl)phenyl, 3-acetamidophenyl, 3-chloro-4-(4-methylpiperazin-1-yl)phenyl, 4-fluorophenyl, 3-cyanophenyl, 4-(4-(pyrimidin-2-yl)piperazin-1-yl)phenyl, 4-(piperidin-1-ylmethyl)phenyl, 4-thiomorpholinophenyl, 4-aminophenyl, 4-(aminosulfonyl)phenyl, 4-(dimethylamino)phenyl, 4-(morpholinomethyl)phenyl, 2-methoxyphenyl, 4-(4-fluorophenylamido)phenyl, 4-(4,5-dihydro-1H-pyrazol-3-yl)phenyl, 4-(2-methoxyphenylamido)phenyl, 4-(3-methoxyphenylamido)phenyl, 4-(4-methoxyphenylamido)phenyl, 4-(4-isopropylpiperidin-1-yl)phenyl 4-(3-oxomorpholinyl)phenyl, 4-(2-cyanomethyl)phenyl, 4-((4-trifluoromethyl)phenylamido)phenyl, or 4-(4-methylpiperidin-1-yl)phenyl.

24. The method of claim 18, wherein $R^1$ is heteroaryl, optionally substituted with one or more substituents Q.

25. The method of claim 24, wherein $R^1$ is 5- or 6-membered heteroaryl, each of which is optionally substituted with one or more substituents Q.

26. The method of claim 24, wherein $R^1$ is indazolyl, optionally substituted with one or more substituents Q.

27. The method of claim 25, wherein $R^1$ is pyridinyl, optionally substituted with one or more substituents Q.

28. The method of claim 27, wherein $R^1$ is 2-morpholino-3-chloropyridin-5-yl, 2-morpholinopyridin-5-yl, 5-morpholinopyridin-2-yl, 2-morpholino-3-methylpyridin-5-yl, 2-(4-isopropylpiperazin-1-yl)-3-methylpyridin-5-yl, 2-(4-methylpiperazin-1-yl)-3-methylpyridin-5-yl, 6-(2,6-dimethyltetrahydro-2H-pyran-4-yl)pyridin-3-yl, or 2-(4-(pyrrolidin-1-yl)piperidin-1-yl)pyridin-5-yl.

29. The method of claim 18, wherein $R^2$ is $C_{1-6}$ alkyl.

30. The method of claim 18, wherein $R^2$ is methyl.

31. The method of claim 18, wherein $R^3$ is $C_{1-6}$ alkyl.

32. The method of claim 18, wherein $R^3$ is methyl.

33. The method of claim 18, wherein the compound is selected from the group consisting of:

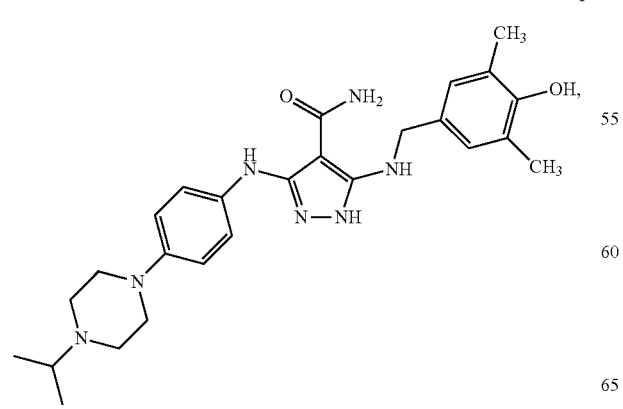

1

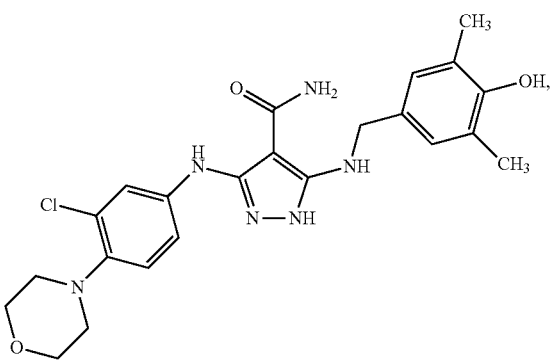

2

3

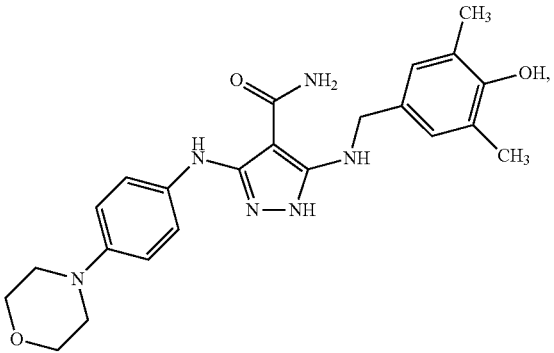

4

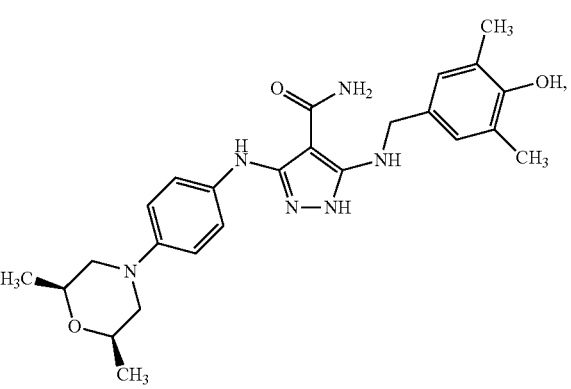

5

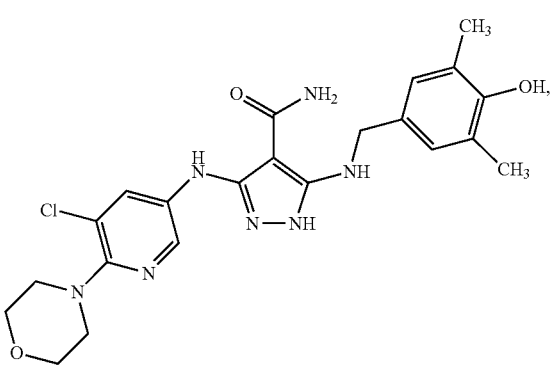

6
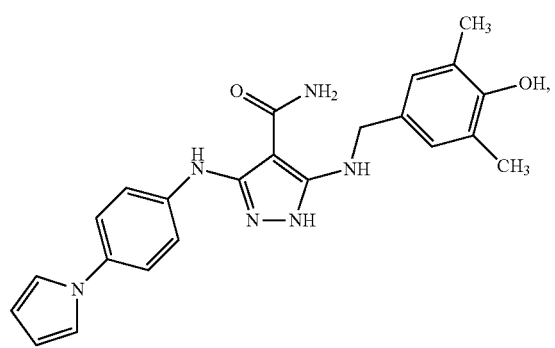
7
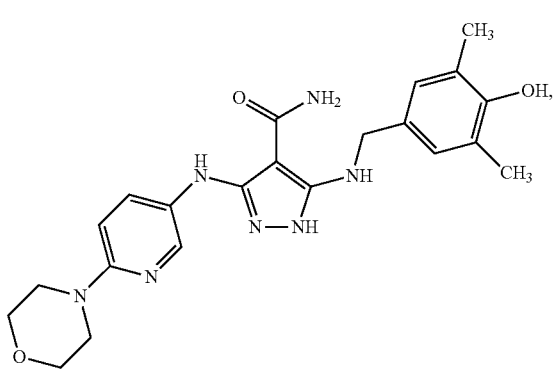
8
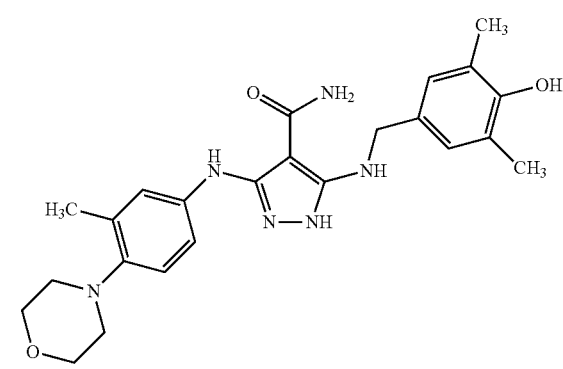
9
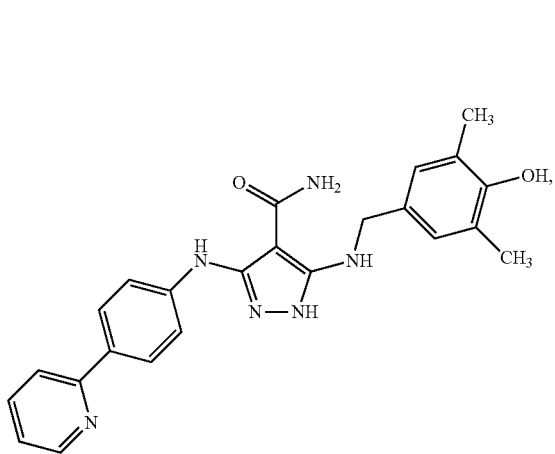
10
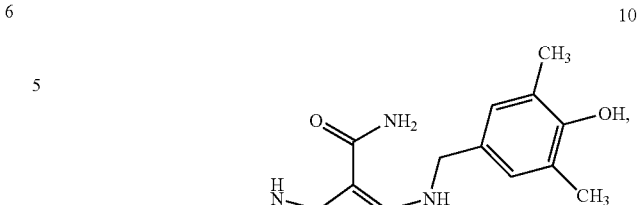
11
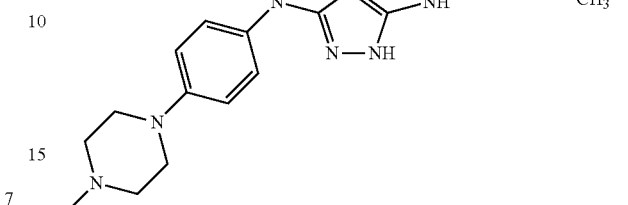
12
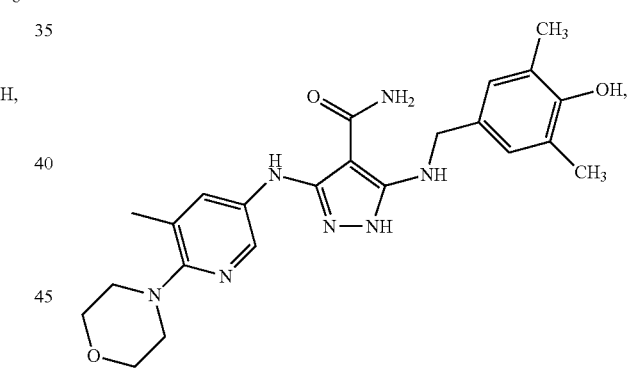
13
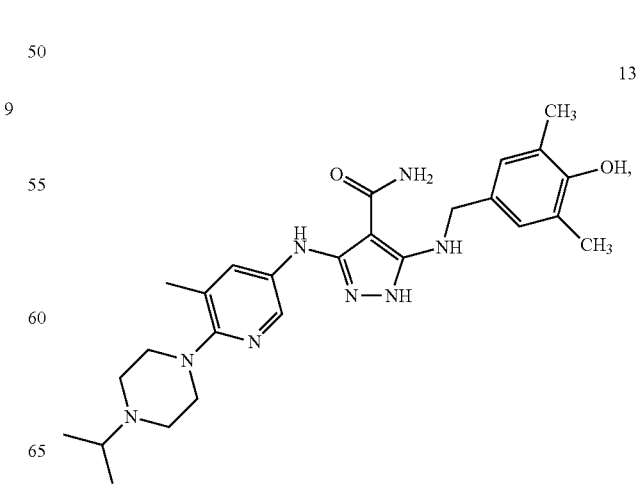

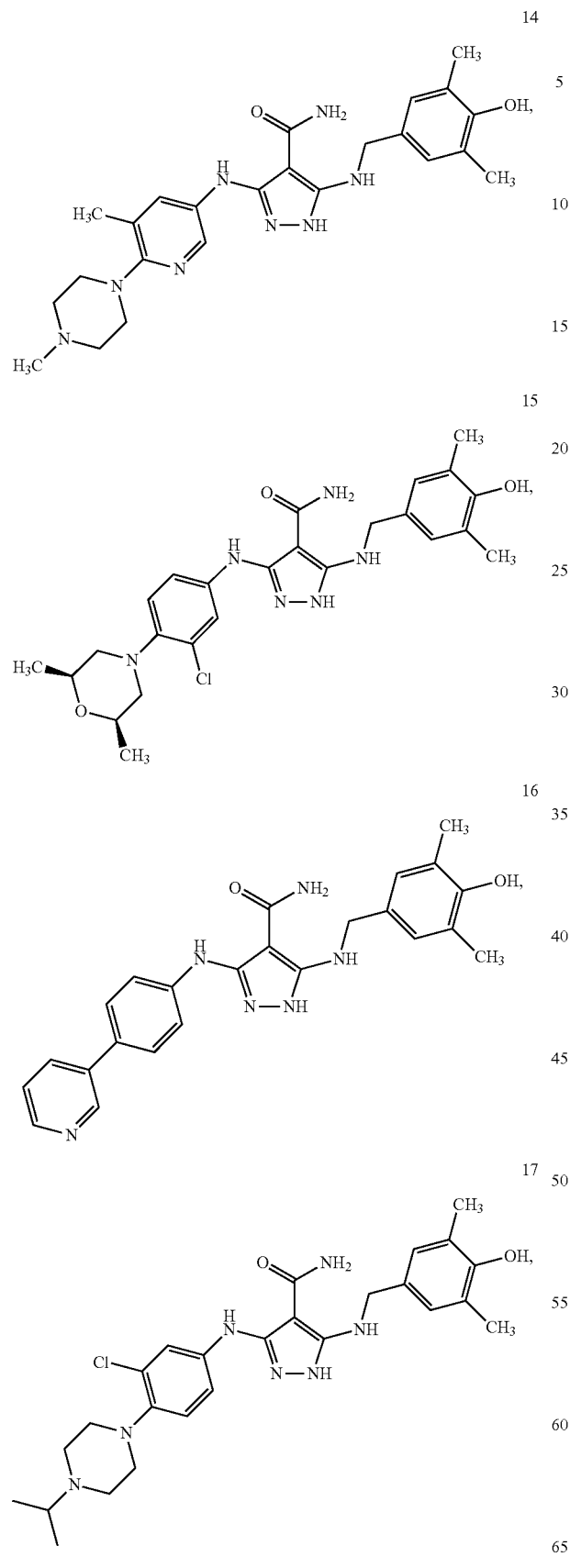
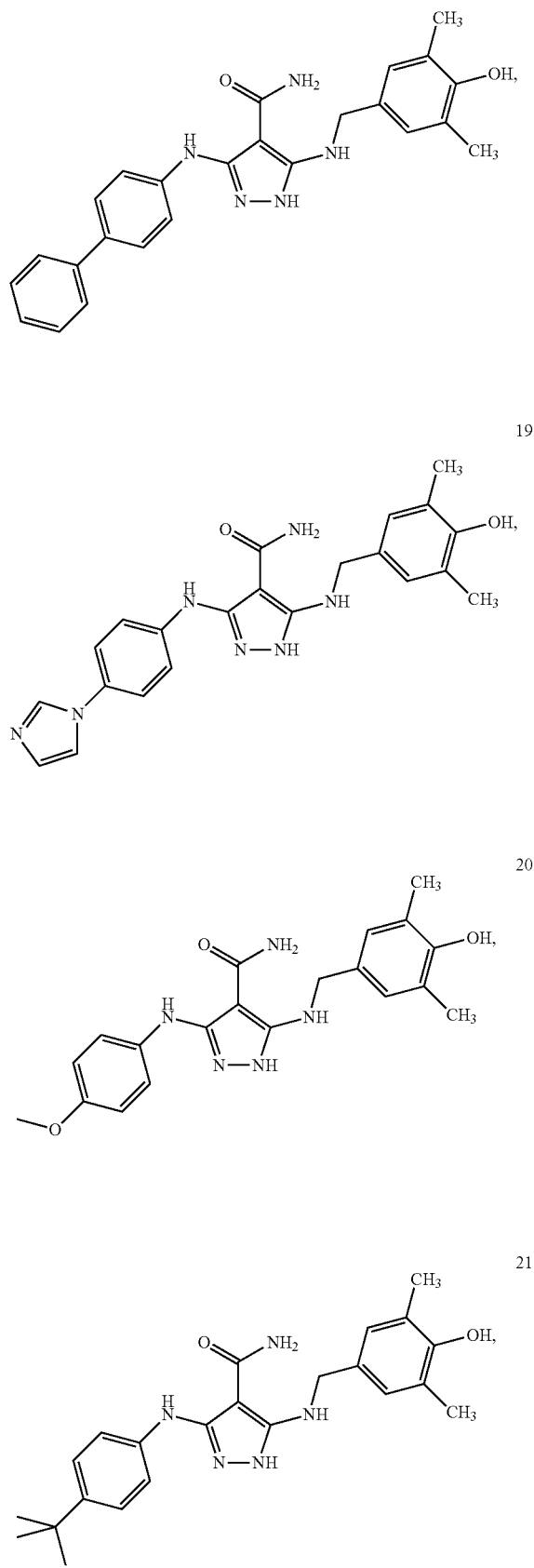

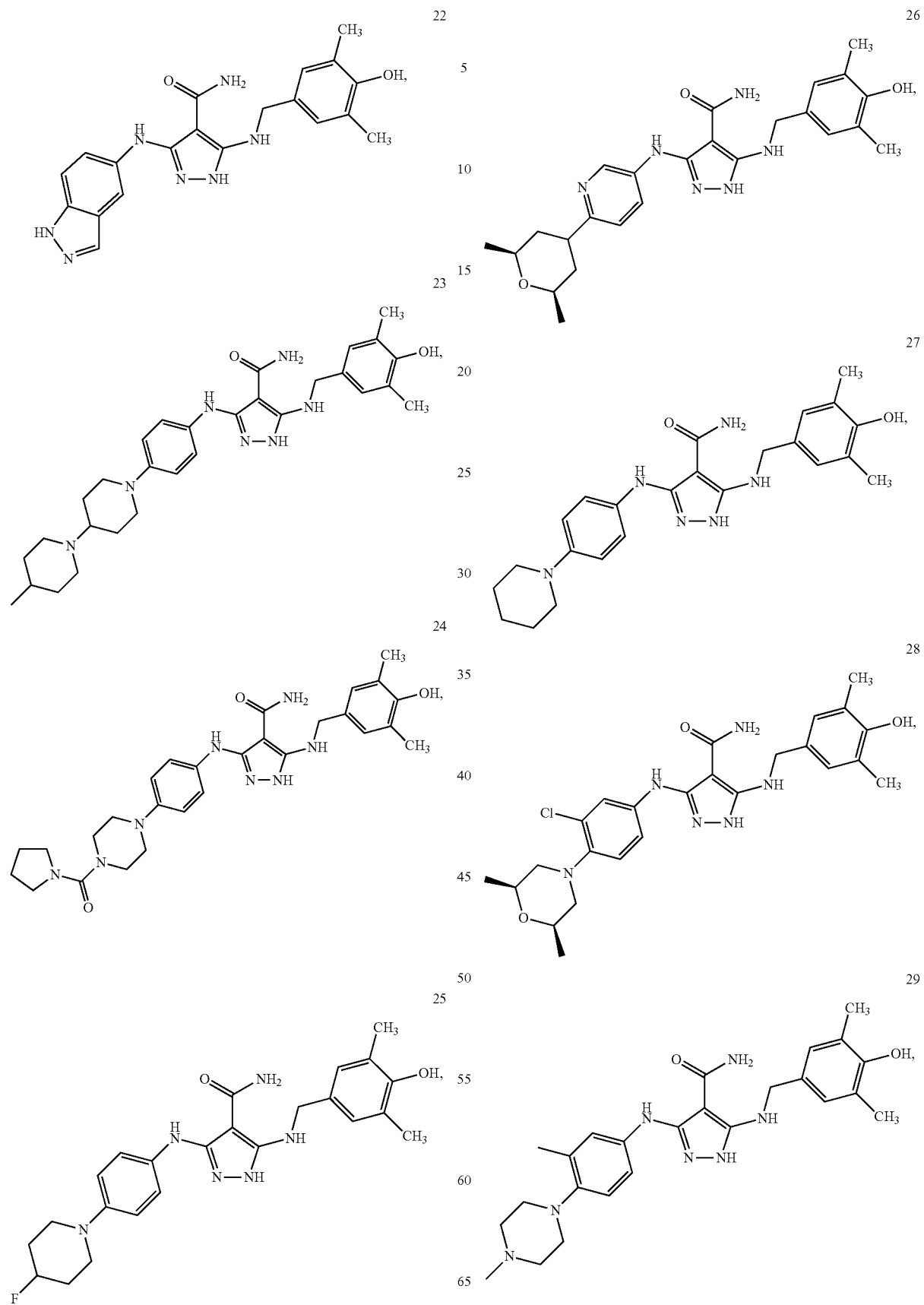

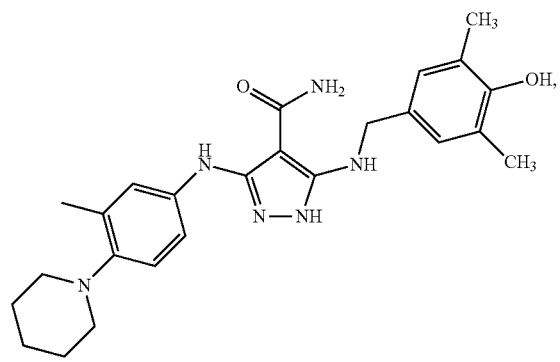
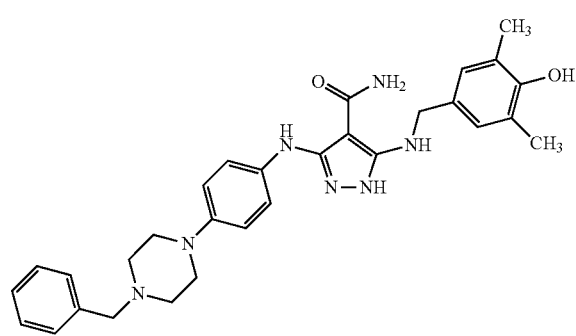
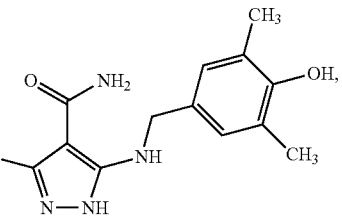
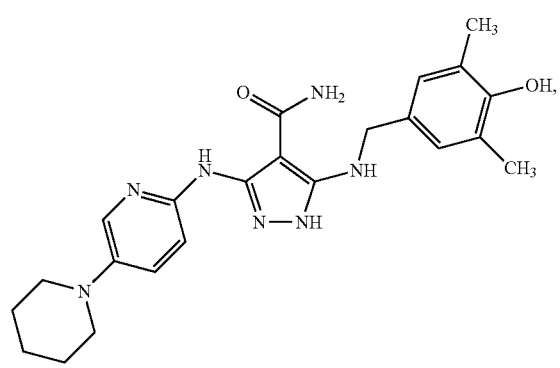

-continued
38
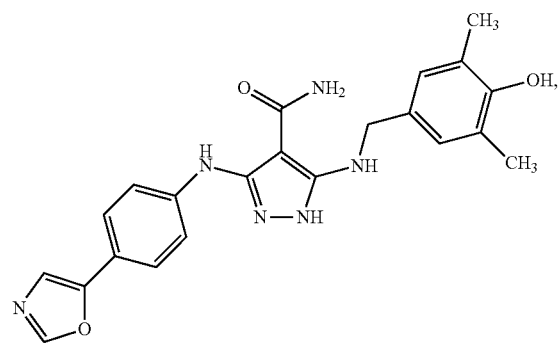
39
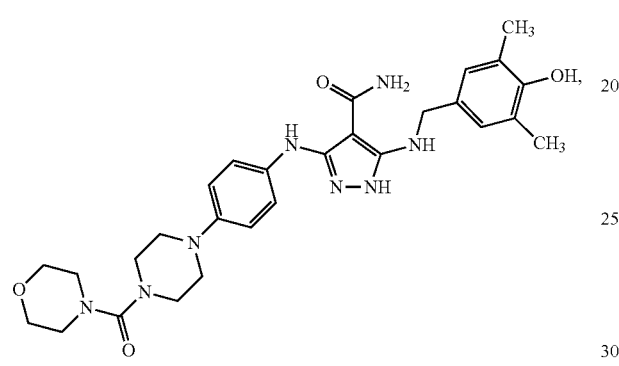
41
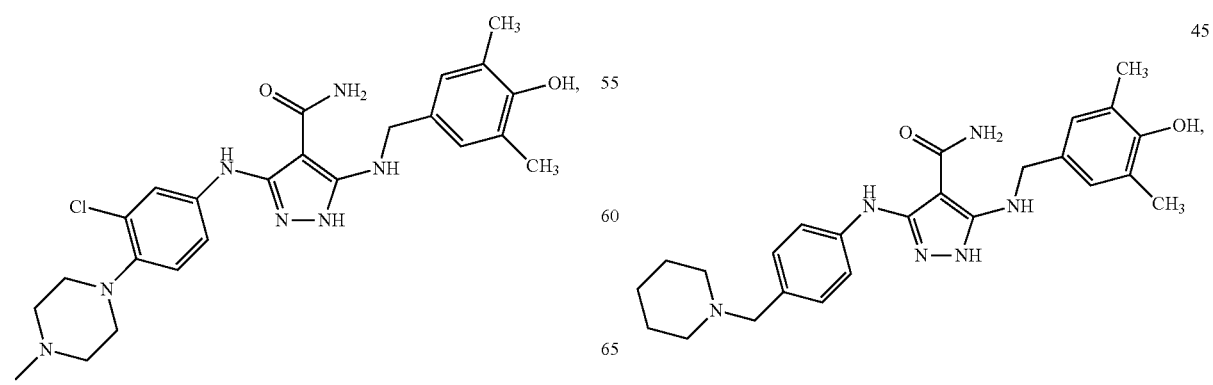
-continued
42
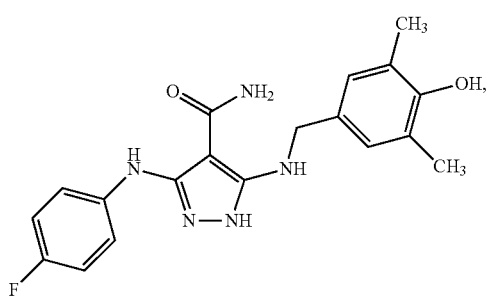
43
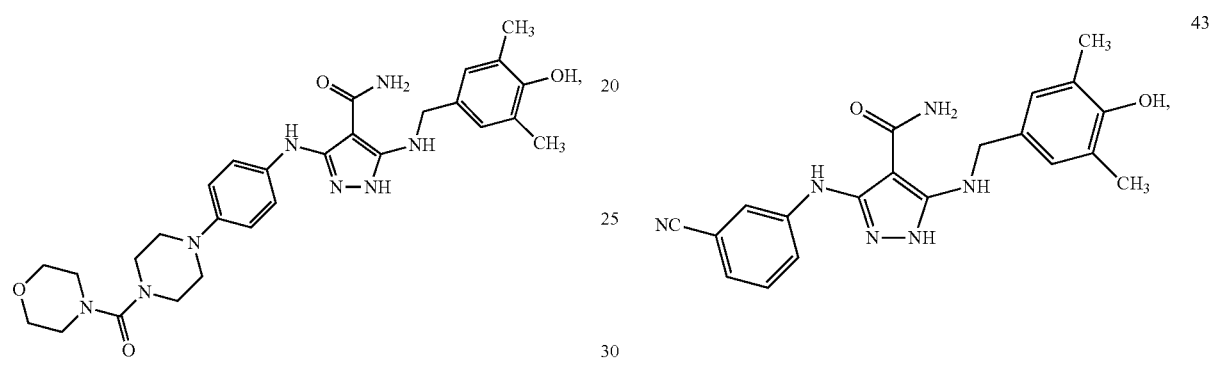
44
45
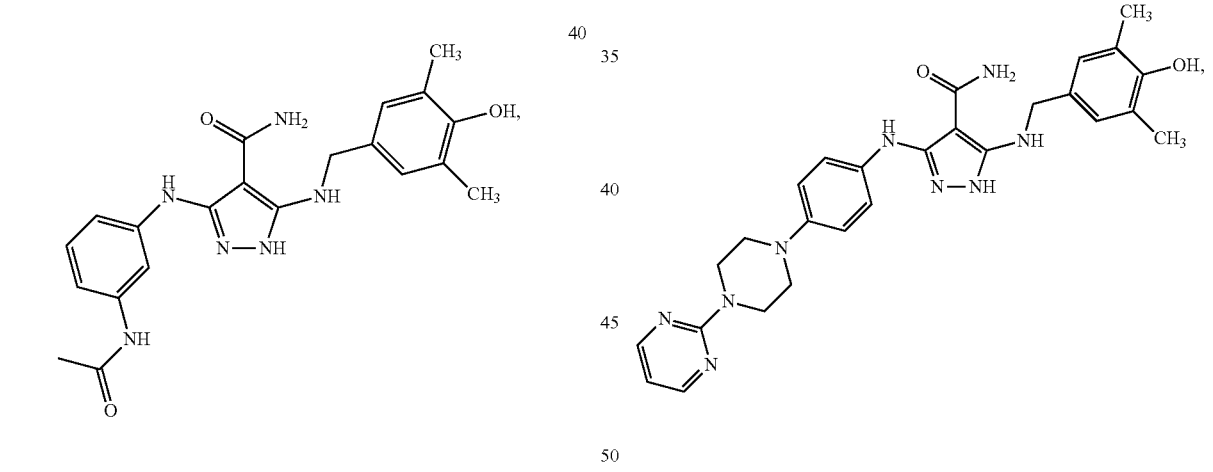

46
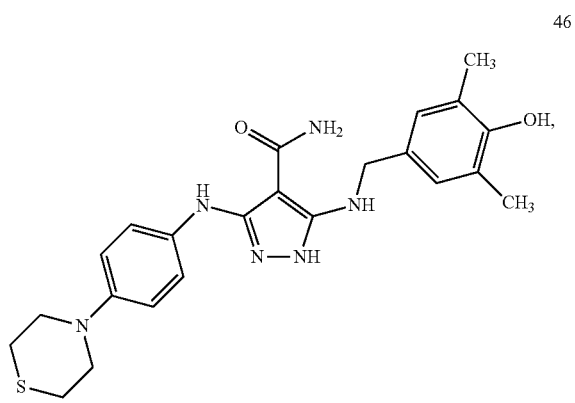
47
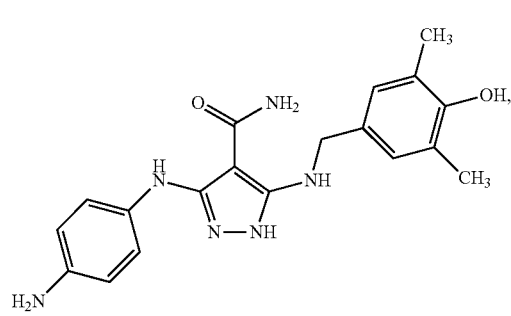
48
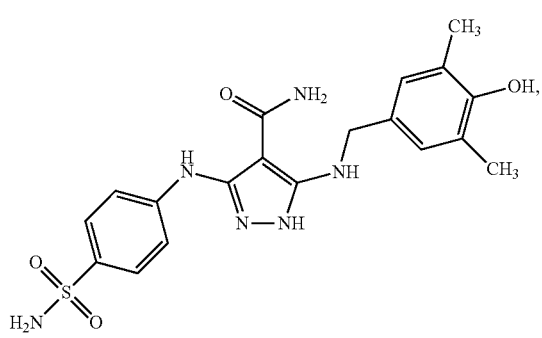
49
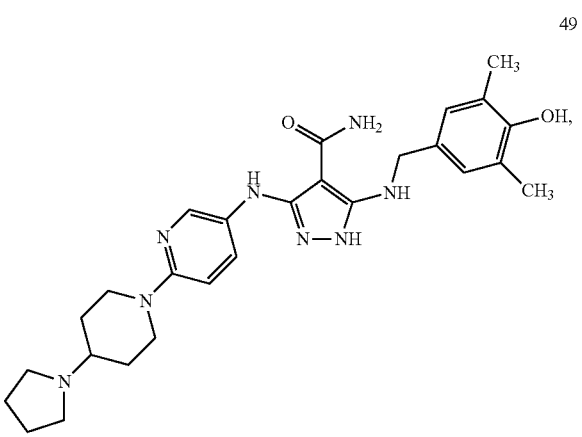
50
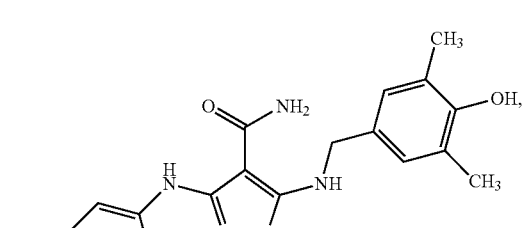
51
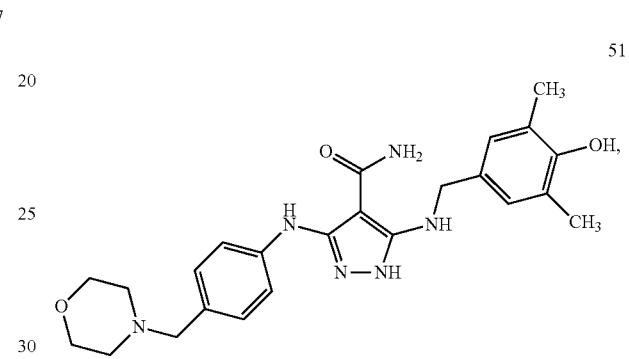
52
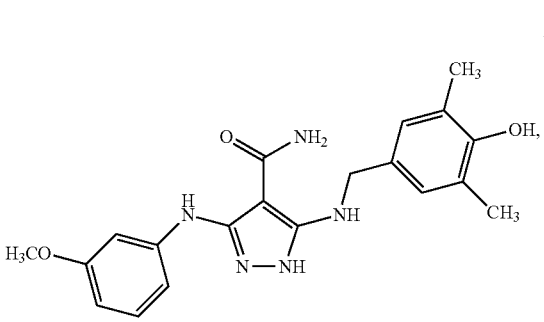
53
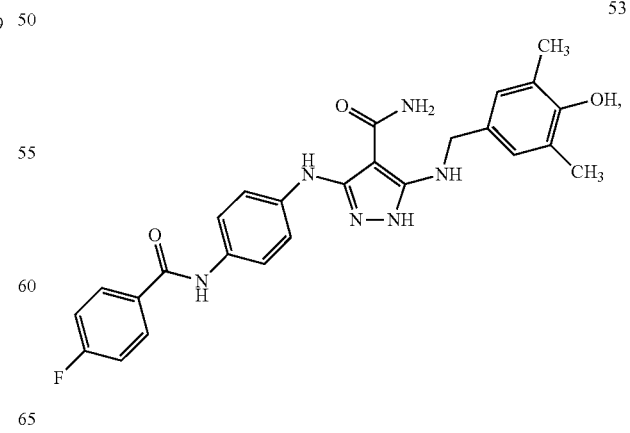

54
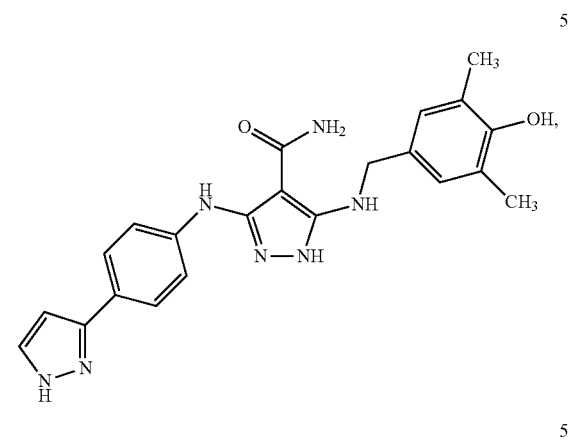
55
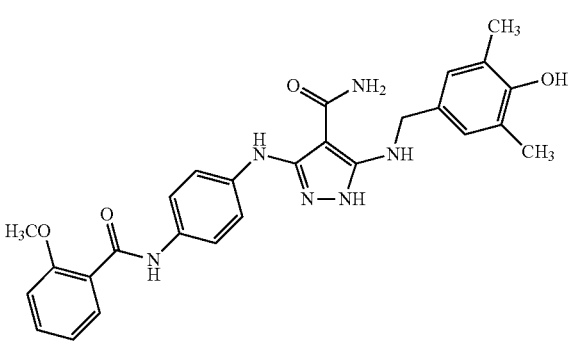
56
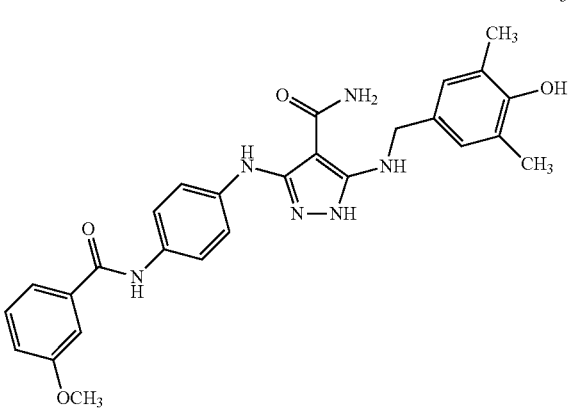
57
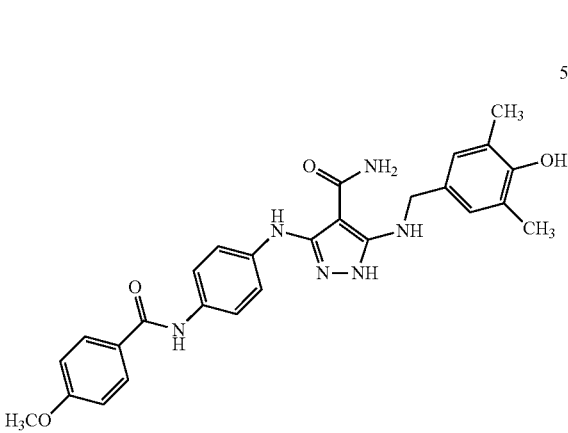
58
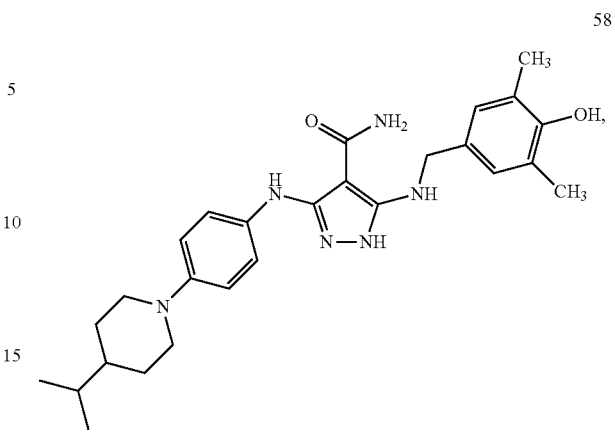
59
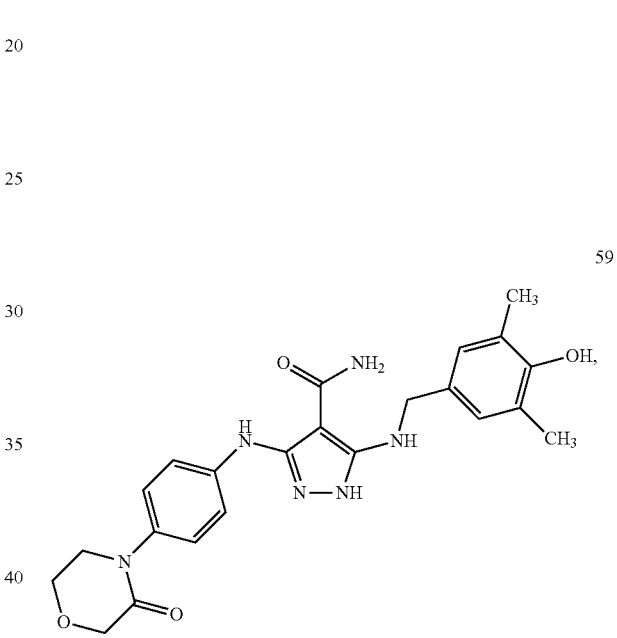
61
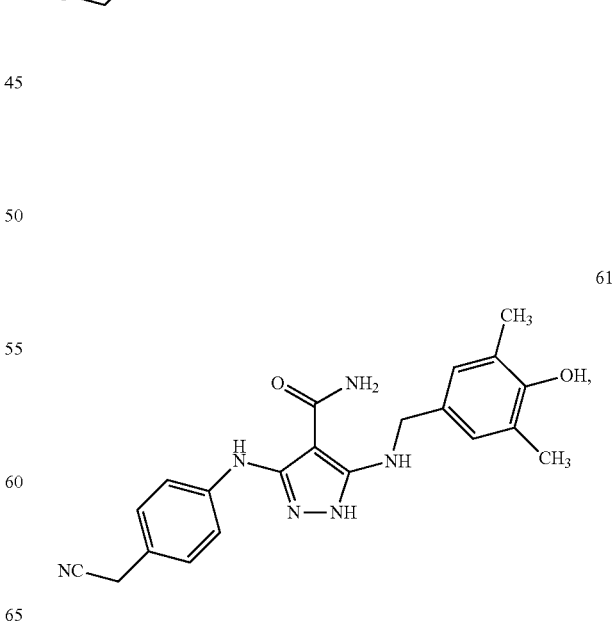

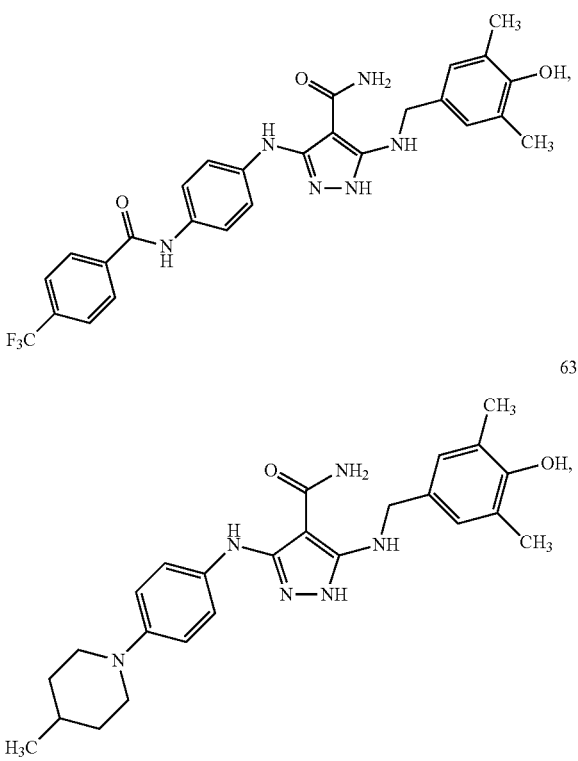

and stereoisomers, enantiomers, mixtures of enantiomers, mixtures of diastereomers, and isotopic variants thereof; and pharmaceutically acceptable salts, solvates, hydrates, and prodrugs thereof.

34. The method of claim 18, wherein the compound is administered in combination with a second therapeutic agent.

35. A method for inhibiting RC kinase activity, comprising contacting a RC kinase with a compound of Formula I:

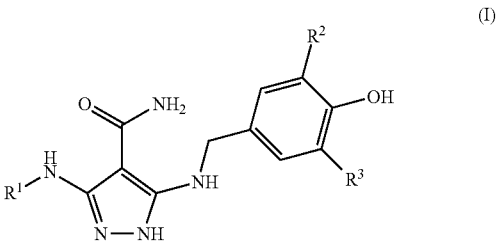

or a stereoisomer, enantiomer, mixture of enantiomers, mixture of diastereomers, or isotopic variant thereof; or a pharmaceutically acceptable salt, solvate, hydrate, or prodrug thereof; wherein:

$R^1$ is $C_{6-14}$ aryl, heteroaryl, or heterocyclyl;

$R^2$ and $R^3$ are each independently $C_{1-6}$ alkyl or $C_{3-10}$ cycloalkyl;

wherein each alkyl, cycloalkyl, aryl, heteroaryl or heterocyclyl is optionally substituted with one or more substituents q, where each q is independently selected from halo, $c_{1-6}$ alkyl, $c_{1-6}$ alkoxy, aryl, heteroaryl, and heterocyclyl, each of which is further optionally substituted with one or more $c_{1-6}$ alkyl, halo, aralkyl, dialkylamino, heterocyclyl, heterocyclylalkyl, and heterocyclylcarbonyl;

with the proviso that the compound is not 3-((3-chlorophenyl)amino)-5-((4-hydroxy-3,5-dimethylbenzyl)amino)-1H-pyrazole-4-carboxamide.

36. The method of claim 1, wherein the disorder, disease, or condition is fibrosis.

37. The method of claim 18, wherein the disorder, disease, or condition is fibrosis.

* * * * *